US010101273B2

(12) United States Patent
Ja

(10) Patent No.: US 10,101,273 B2
(45) Date of Patent: Oct. 16, 2018

(54) OPTICAL EMISSION COLLECTION AND DETECTION DEVICE AND METHOD

(71) Applicant: FLIR Detection, Inc., Wilsonville, OR (US)

(72) Inventor: Shiou-jyh Ja, Stillwater, OK (US)

(73) Assignee: FLIR Detection, Inc., Wilsonville, OR (US)

( * ) Notice: Subject to any disclaimer, the term of this patent is extended or adjusted under 35 U.S.C. 154(b) by 440 days.

(21) Appl. No.: 14/821,553

(22) Filed: Aug. 7, 2015

(65) Prior Publication Data

US 2016/0033410 A1 Feb. 4, 2016

Related U.S. Application Data

(63) Continuation-in-part of application No. 13/767,509, filed on Feb. 14, 2013, now Pat. No. 9,645,085.

(60) Provisional application No. 61/614,228, filed on Mar. 22, 2012, provisional application No. 61/600,203, filed on Feb. 17, 2012.

(51) Int. Cl.
*G01N 21/64* (2006.01)
*G01N 33/22* (2006.01)

(52) U.S. Cl.
CPC ......... *G01N 21/648* (2013.01); *G01N 21/643* (2013.01); *G01N 21/645* (2013.01); *G01N 21/6428* (2013.01); *G01N 33/227* (2013.01); *G01N 2021/6423* (2013.01)

(58) Field of Classification Search
None
See application file for complete search history.

(56) References Cited

U.S. PATENT DOCUMENTS

| 4,180,739 | A | 12/1979 | Abu-Shumays |
| 4,818,710 | A | 4/1989 | Sutherland et al. |
| 5,341,215 | A | 8/1994 | Seher |
| 5,508,809 | A | 4/1996 | Peacock et al. |
| 5,747,349 | A | 5/1998 | Van Den Engh et al. |
| 6,300,638 | B1 | 10/2001 | Groger et al. |

(Continued)

OTHER PUBLICATIONS

Lakowicz, Joseph R.—"Radioative decay engineering 3. Surface plasmon-coupled directional emission", Article, Jan. 15, 2004, p. 153-169, vol. 324, Iss. 2, Analytical Biochemistry, Baltimore, U.S.

(Continued)

*Primary Examiner* — Shawn Decenzo
(74) *Attorney, Agent, or Firm* — Haynes and Boone, LLP

(57) ABSTRACT

This invention generally relates to optical devices that can collect and detect signal emissions effectively while allowing the excitation light path and the sample flow path to coexist non-obstructively in a compact format. The device has various embodiments, such as an embodiment including a plurality of reporters disposed on a sensing surface, wherein each one of the plurality of reporters is configured to react with a least one target analyte, a hyperspectral detection module configured to capture hyperspectral image data corresponding to the plurality of reporters, and a controller. The controller is configured to receive the hyperspectral image data from the hyperspectral detection module and generate a temporal spectral signature corresponding to each one of the plurality of reporters from the received hyperspectral image data.

15 Claims, 34 Drawing Sheets

(56) References Cited

U.S. PATENT DOCUMENTS

| | | |
|---|---|---|
| 6,339,062 B1 | 1/2002 | Williams et al. |
| 6,346,376 B1 | 2/2002 | Sigrist et al. |
| 6,783,814 B2 | 8/2004 | Swager et al. |
| 7,301,642 B2 | 11/2007 | Shimizu |
| 7,443,507 B2 | 10/2008 | Ran et al. |
| 7,718,964 B2 | 5/2010 | Frey |
| 7,835,006 B2 | 11/2010 | Ja |
| 7,982,878 B1 * | 7/2011 | Ja .................. G01N 21/648 250/458.1 |
| 9,719,856 B2 * | 8/2017 | Potter ................ G01J 3/2823 |
| 2005/0053974 A1 | 3/2005 | Lakowicz et al. |
| 2006/0109472 A1 | 5/2006 | Muraishi |
| 2013/0120754 A1 * | 5/2013 | Wilson .................. G01J 3/26 356/455 |
| 2015/0153156 A1 * | 6/2015 | Shah .................... G01J 3/36 356/456 |

OTHER PUBLICATIONS

Gryczynski et al.—"Ultraviolet Surface Plasmon-Coupled Emission Using Thin Aluminum Films", Article, Jun. 8, 2004, pp. 4076-4081, 76 (14), Analytical Chemistry, Baltimore, U.S.

\* cited by examiner

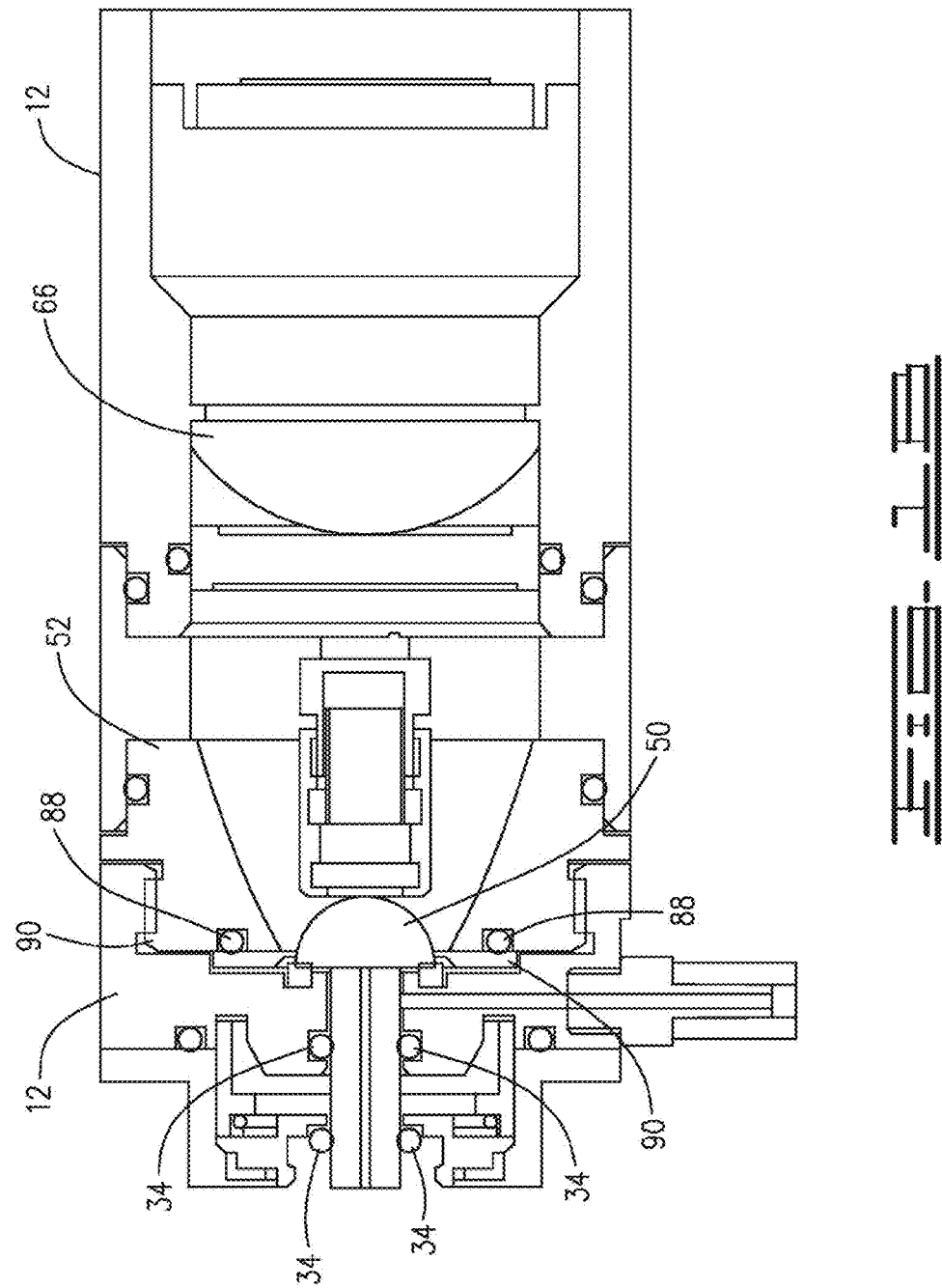

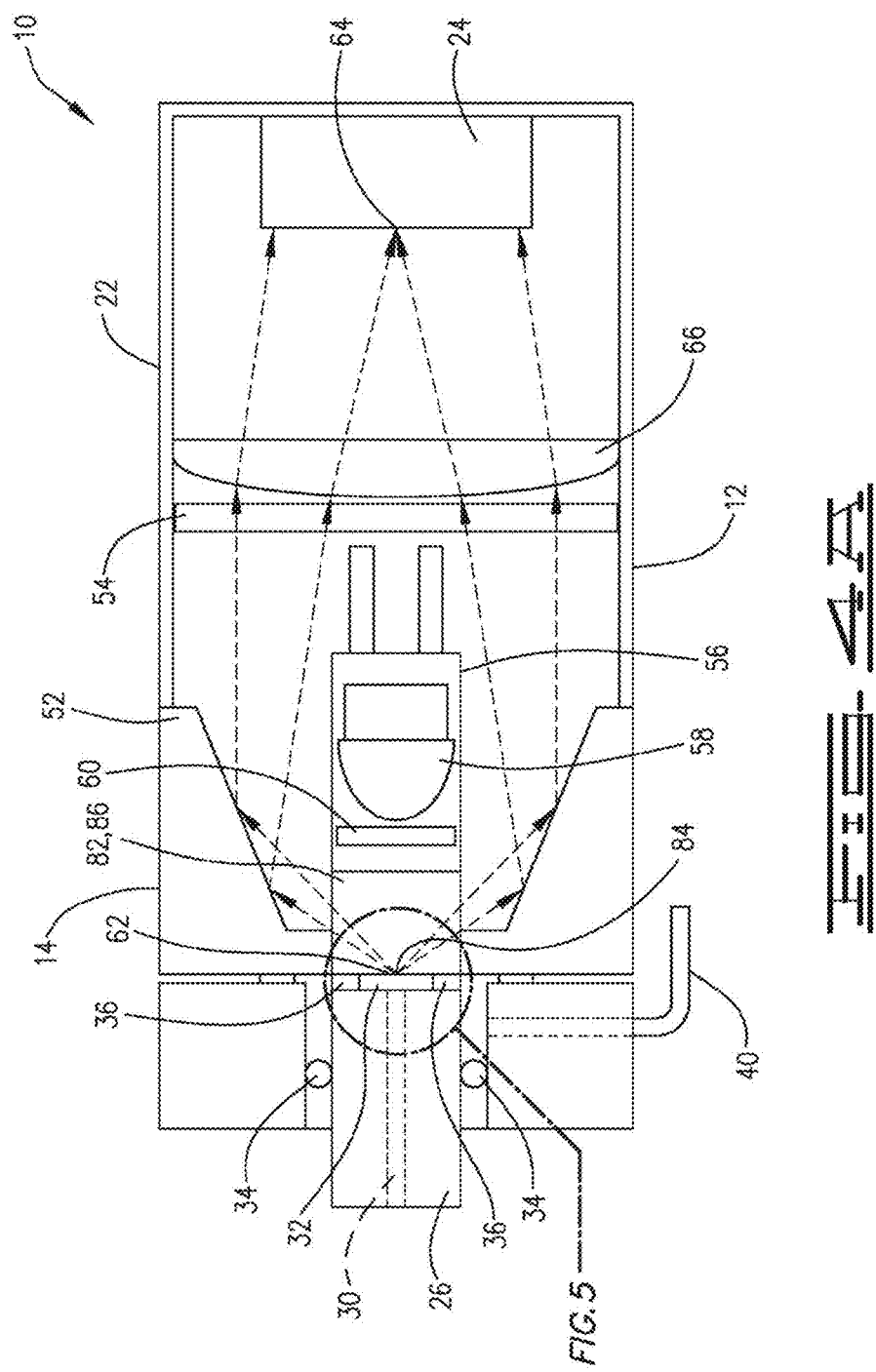

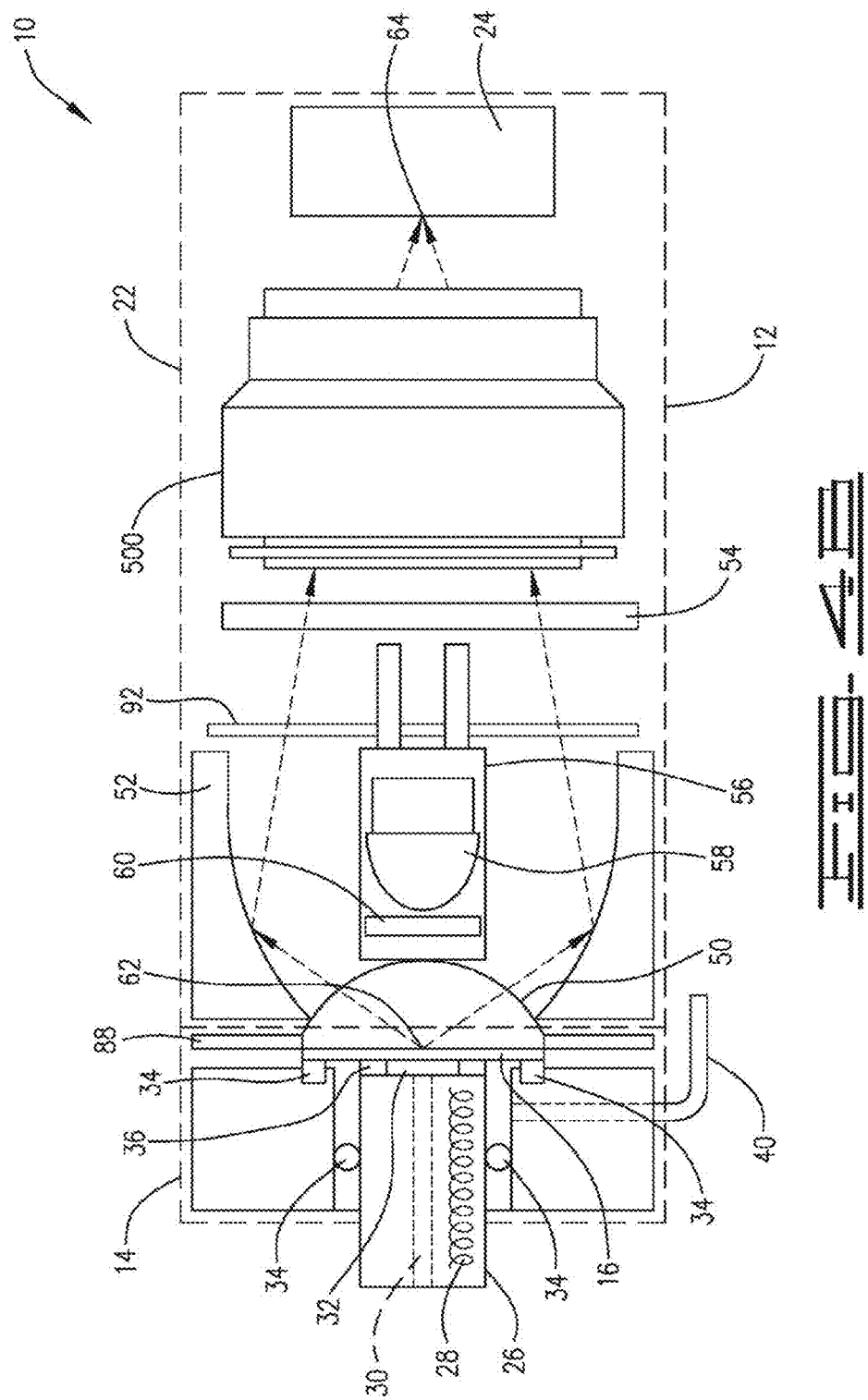

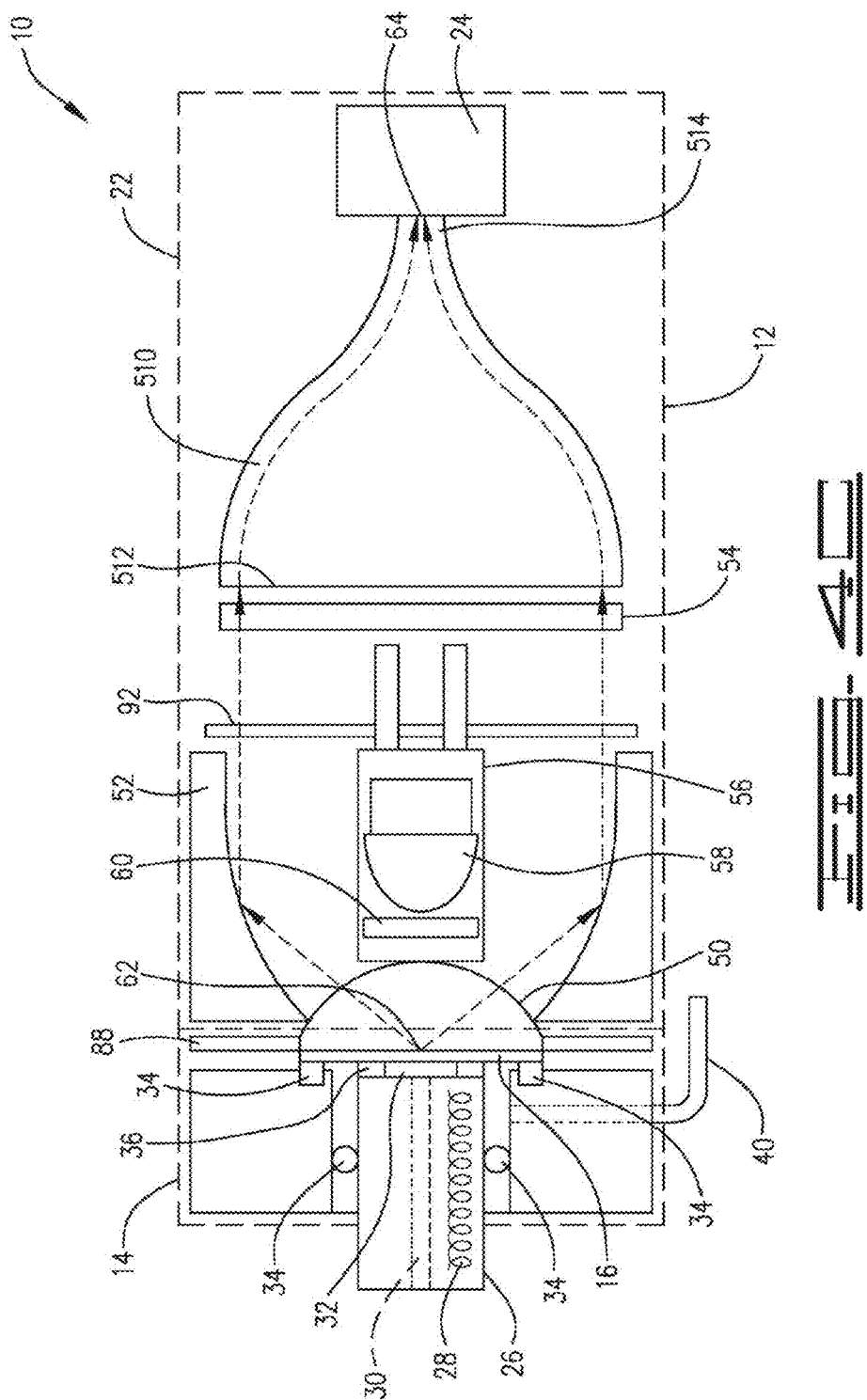

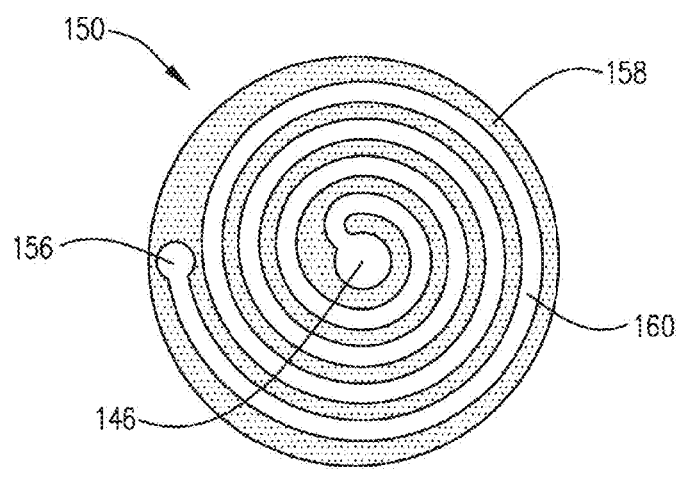
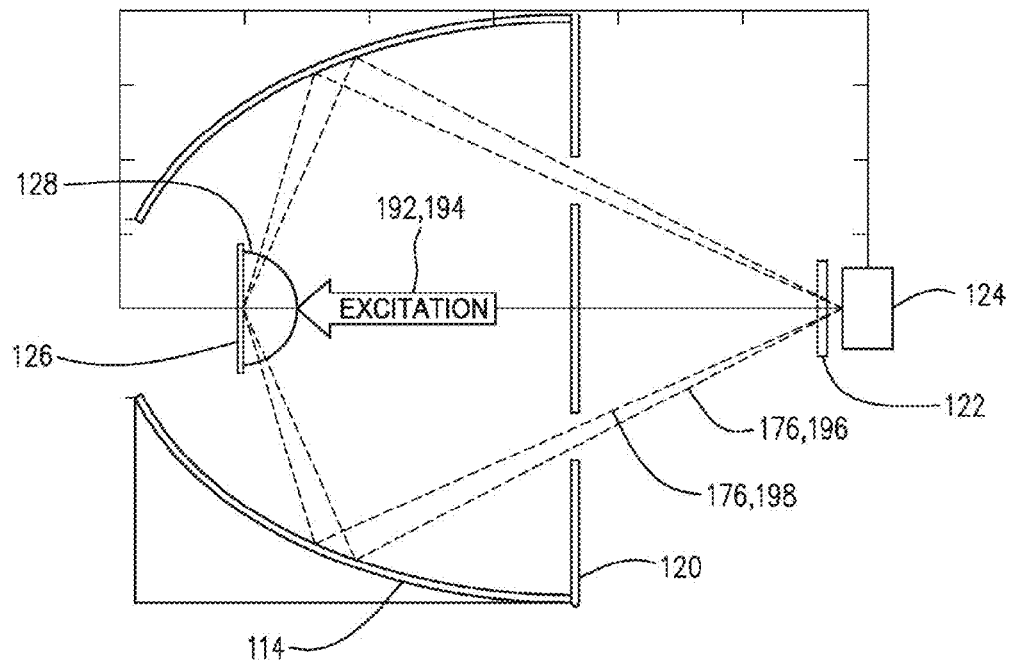

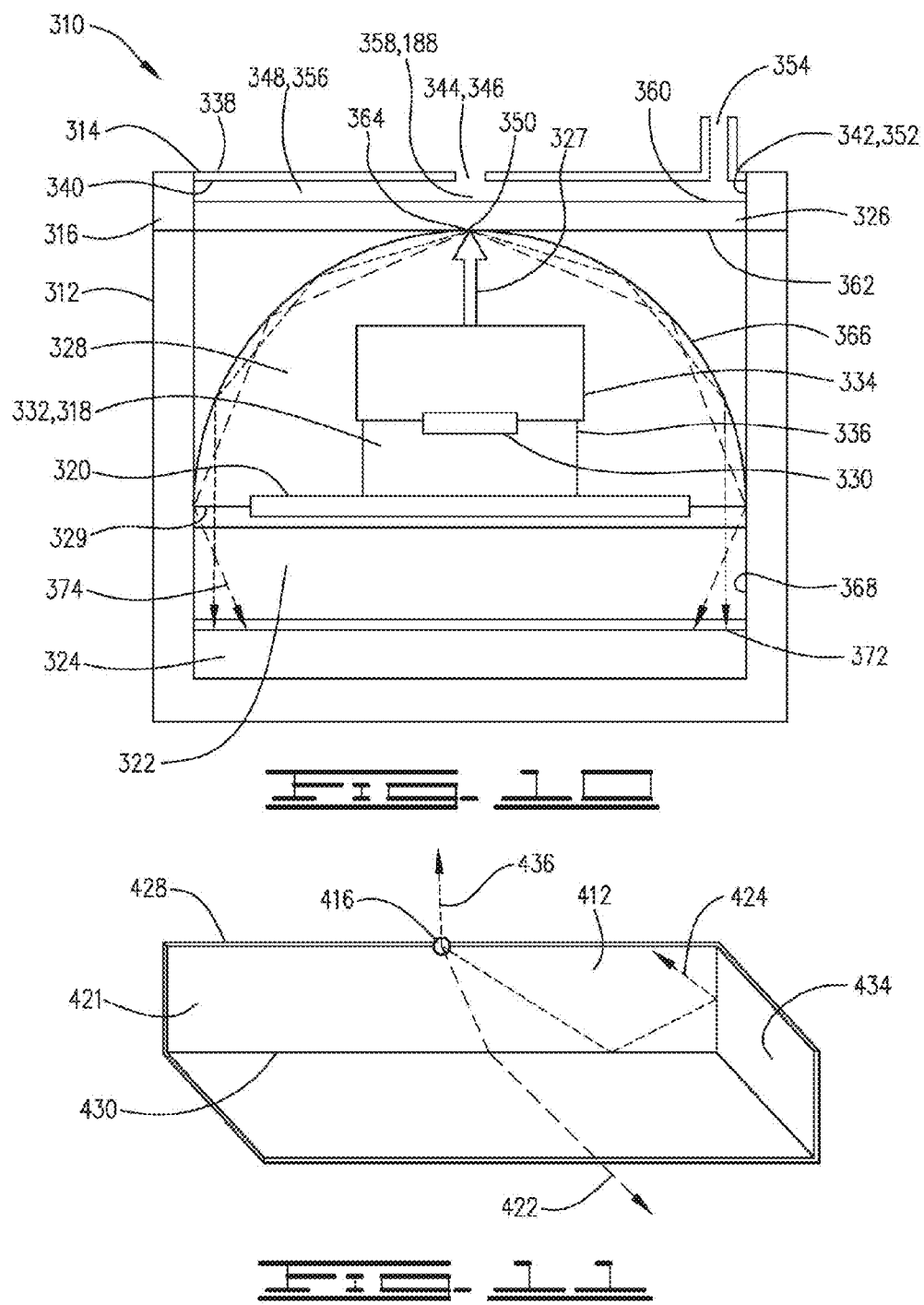

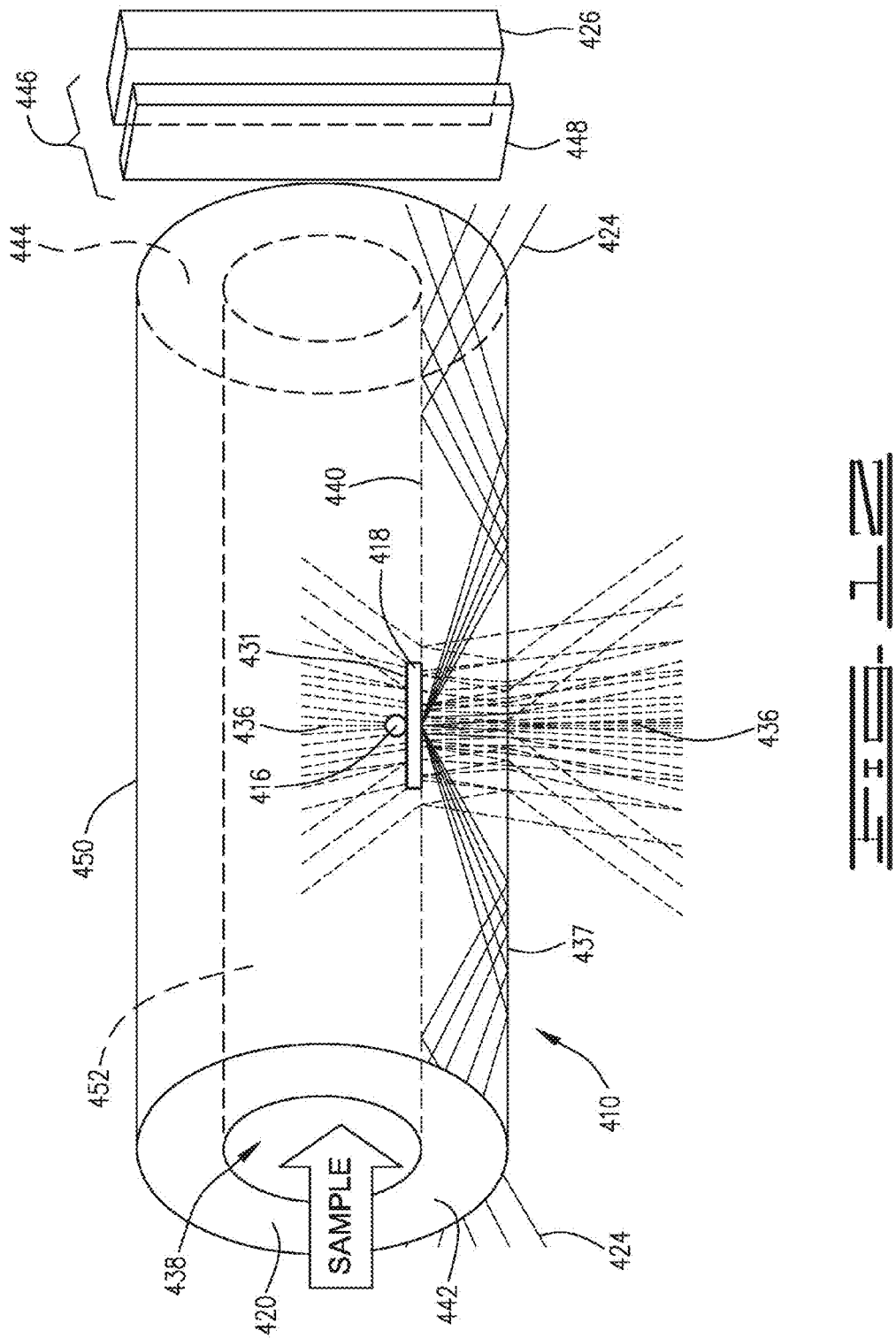

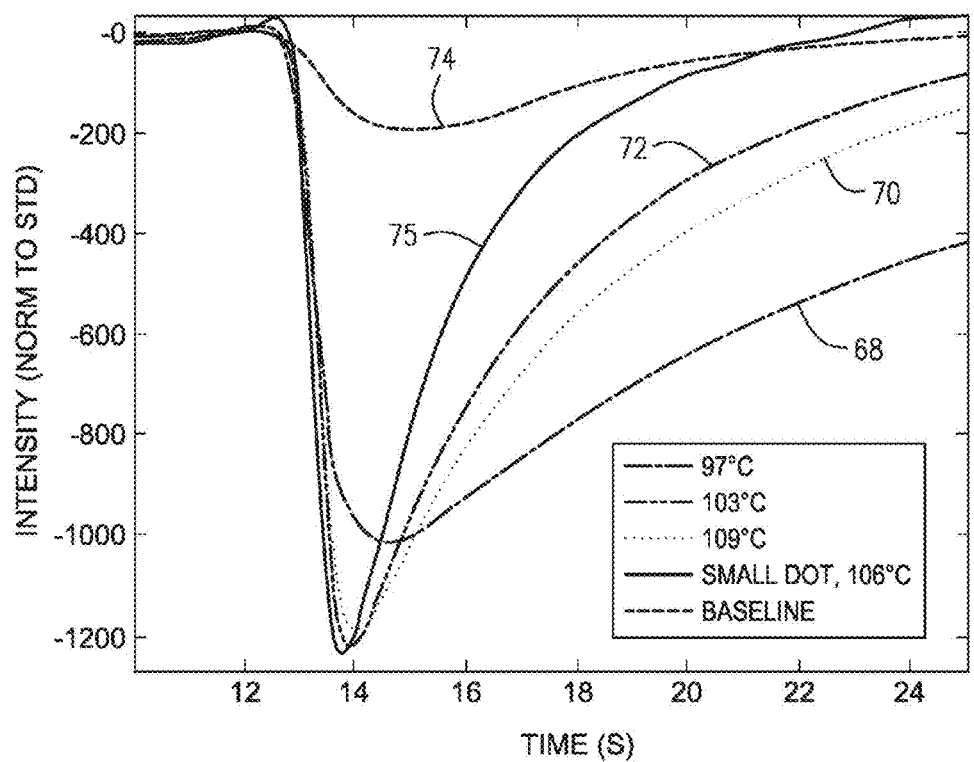
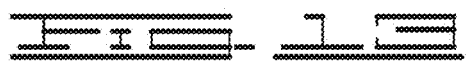

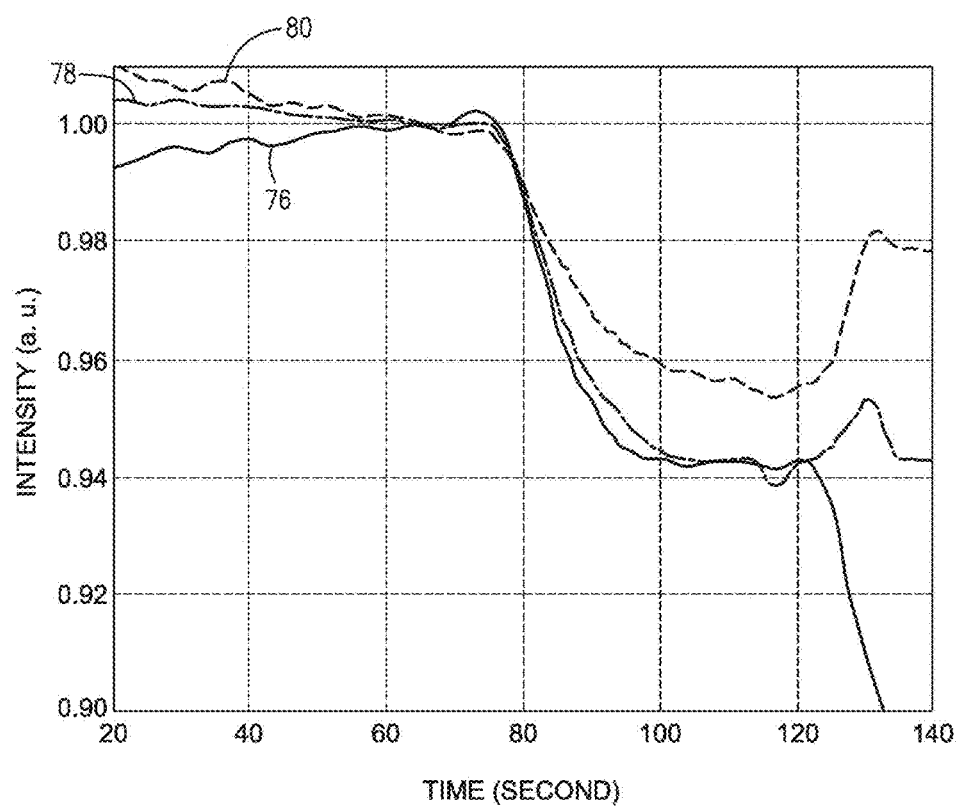
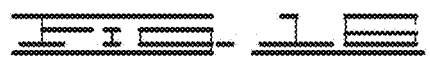

Part A : SPCE foucusing optics.

Part B : SPCE Complex Lens Assembly

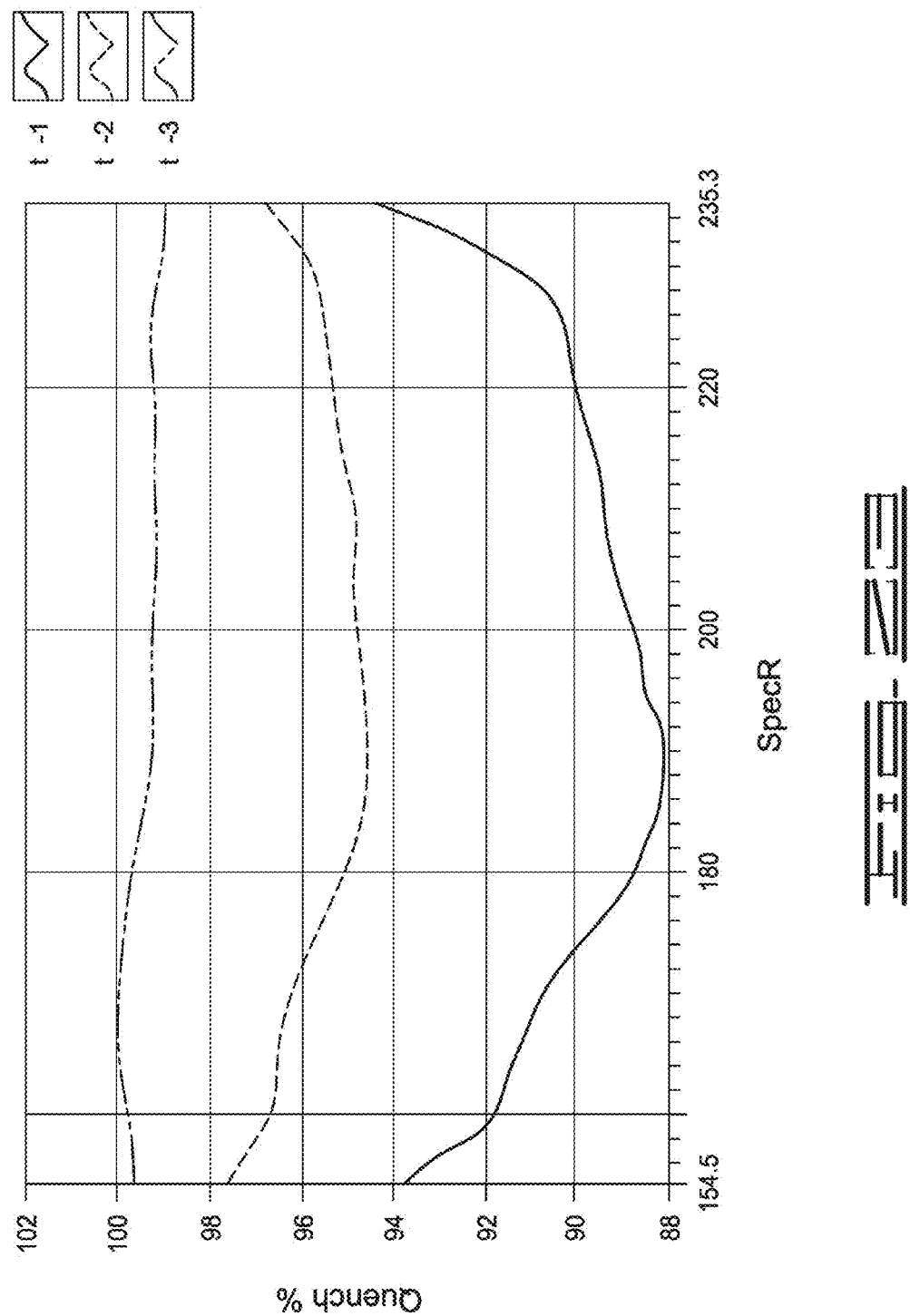

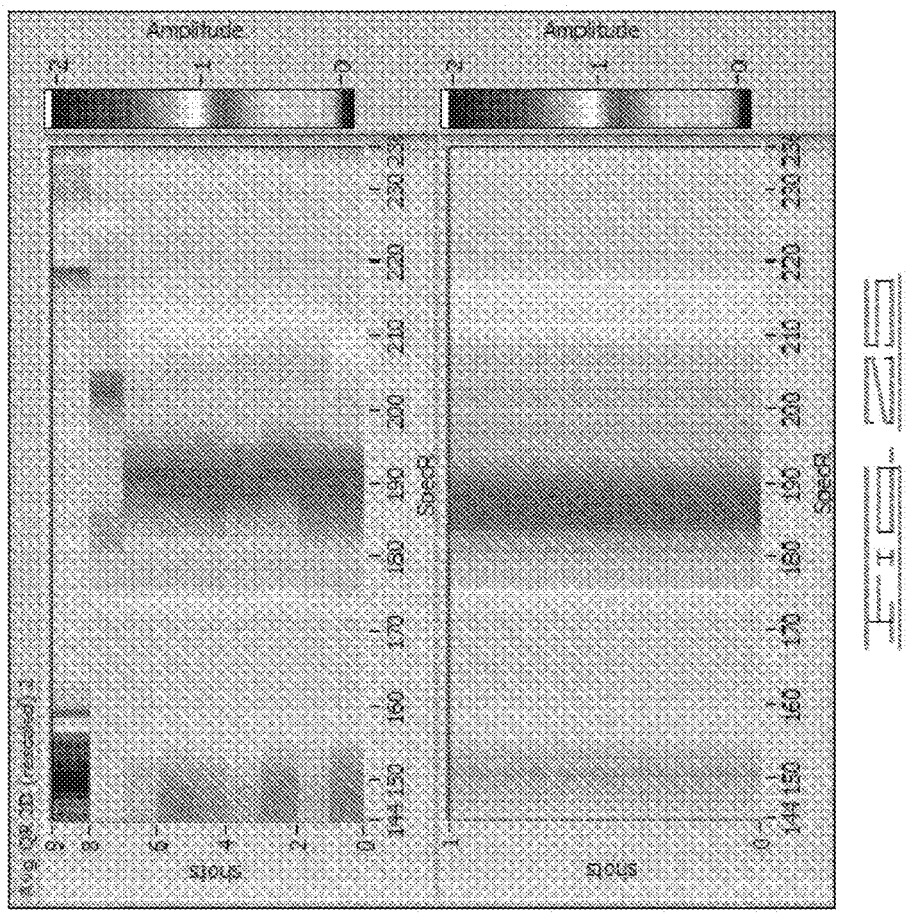

OPTICAL EMISSION COLLECTION AND DETECTION DEVICE AND METHOD

CROSS-REFERENCE TO RELATED APPLICATIONS

This application is a continuation-in-part of U.S. patent application Ser. No. 13/767,509, filed Feb. 14, 2013, which claims the benefit of U.S. Provisional Application No. 61/600,203, filed Feb. 17, 2012, and U.S. Provisional Application No. 61/614,228, filed Mar. 22, 2012, all three of which are hereby incorporated by reference herein.

STATEMENT AS TO FEDERALLY SPONSORED RESEARCH

This application was supported in part by a contract from the U.S. Army, Contract Number: W909MY-10-C-0037. The United States Government may have rights in, and to, this application by virtue of this funding.

BACKGROUND

The present invention is for a new inventive device and method to collect and detect optical fluorescent emissions from a reporter and an analyte. In particular, the present invention is an optical collection device for collecting fluorescent optical emissions at the molecular level, and a method for using the same. The molecular-based optical fluorescence emission detection system is an optical device suitable for sensing the presence of explosive, chemical or biological warfare substances using a chemical warfare indicating chromophore (CWIC) or amplifying fluorescence polymers (AFPs), such as those polymers discussed in U.S. Pat. No. 7,208,122.

Explosive, chemical and biological substances are difficult to detect. One approach for detecting these substances is to use a fluorescence detection scheme. The explosive, chemical and biological substances, called analytes, interact with an innovative fluorescent material such as a CWIC or AFP, and cause changes in the intensity, wavelength, or the duration of the fluorescence signal. The detection of explosive, chemical or biological substances can be achieved by monitoring such changes. One challenge of traditional fluorescence-based detection systems is the low signal-to-noise ratio (SNR). The low SNR may be due to the low fluorescence signal and the presence of excitation light and ubiquitous background noise in the signal collection path.

One focus of current research is to improve the detection of explosive, chemical and biological warfare substances reacting with CWIC or AFP materials by improving optical collection efficiency and noise rejection. As an alternative to traditional fluorescence-based methods, surface plasmon-coupled emission (SPCE) sensors are best suited to collect fluorescing emissions, and provide increased optical SNR and hence sensitivity. Testing has shown that a SPCE sensor arrangement enhances fluorescence signal strength by significantly improving the collection efficiency. Additionally, a SPCE sensor arrangement increases the signal-to-noise ratio via the implementation of forbidden light detection and polarization filtering. The highly p-polarized SPCE signal allows polarization filtering to be used to further improve signal-to-noise ratio. These two advantages enable high sensitivity and low detection limits for the fluorescence-based detection system. However, current optical collection devices for SPCE sensor arrangements are cumbersome and difficult to use.

The need is for a less cumbersome apparatus and method to optically detect the fluorescent emission from an explosive, chemical or biological warfare substance reacting with a CWIC or AFP while having a high signal-to-noise ratio. The requirement is to have a portable apparatus to detect the fluorescent emissions of explosive, chemical or biological warfare samples generated from the reaction of the samples with CWIC or AFP material.

SUMMARY

In one embodiment, the current invention provides an optical detection device. The optical detection device comprises a housing having an input segment suitable for receiving an analyte transport fluid. Further, an optic segment and a sensing slide are positioned within the housing. The sensing slide carries at least one reporter having the ability to react with at least one target analyte. Located between the input segment and optic segment, the sensing slide is in fluid communication with the input segment and is in optical communication with the optic segment.

The current invention can utilize a replaceable sensing device. The replaceable sensing device comprises a lens and a reflector. The lens has a sensing surface that carries a plurality of reporters.

The input segment of the current invention can be positioned within the housing and is adapted to receive and communicate a sample of analyte transport fluid carrying at least one target analyte to the sensing slide. The input segment can include a nozzle with a capillary. The capillary provides communication of the analyte transport fluid from outside the housing through the nozzle to a flow cell. The flow cell is in fluid communication with the capillary.

The sensing slide carries at least one reporter thereon, and is in fluid communication with the flow cell.

The optic segment is positioned within the housing, and is in optical communication with the sensing slide. The optic segment includes a light source adapted to generate a first wavelength, a lens, a reflector, and at least one optical excitation filter.

The first wavelength is adapted to generate a second wavelength when illuminating the reporter. The reporter is adapted to change the second wavelength when the reporter reacts with the target analyte. The lens is positioned adjacent to the sensing slide and has an index matching fluid separating it and the sensing slide. The lens is adapted to optically shift the second wavelength and the changed second wavelength to a new optical path. The optical emission filter is positioned to limit the spectral range of the second wavelength and the changed second wavelength.

The detector is in optical communication with the optic segment, and adapted to receive the second wavelength and the changed second wavelength.

An embodiment for a method of using the inventive apparatus comprises the following steps:
(a) sampling of an analyte transport fluid with a collection device, the analyte transport fluid carrying at least one target analyte;
(b) illuminating a reporter positioned in the collection device with an illuminating source at a first wavelength, whereby during illumination the reporter fluoresces as a second wavelength,
(c) detecting the second wavelength with a detector;
(d) reacting the target analyte with the reporter while continuing to illuminate the reporter at the first wavelength thereby producing a changed second wavelength; and (e) detecting the changed second wavelength.

The present invention can utilize a waveguiding capillary. The waveguiding capillary includes a first end and a second end. The capillary has a substrate applied on an inner wall. The substrate comprises a metallic layer applied to the inner wall, a dielectric layer applied to the first layer and at least one reporter layer applied to second layer. The first layer is preferably a metallic layer and the second layer is preferably a dielectric layer. The reporter is selected to react with at least one target analyte.

If a waveguide capillary is used, the input segment has a nozzle in fluid communication with first end of the capillary. The optic segment of the device is in optical communication with the waveguiding capillary. The optic segment includes a light source and an optical filter. The light source is adapted to provide optical excitation to the reporter. The light source is transversely positioned on a side of the waveguiding capillary. The light source generates a first wavelength. The illumination of the reporter with the first wavelength generates an emission at a second wavelength. The second wavelength undergoes a change during a reaction between the analyte and reporter. The optical filter is adapted to filter a portion of the second wavelength and the changed second wavelengths. Additionally, the detector of the device is adapted to longitudinally receive the second wavelength and the changed second wavelength from the waveguiding capillary.

The current invention can utilize an air-sampling nozzle of the form that has a cylindrical receptacle with an open end and a receiving end. A borehole penetrates the receiving end to allow the sampled air to flow therethrough. The borehole is in fluid communication with a flow channel. The flow channel is formed by the receiving end and a SPCE sensing slide, wherein the area between the two forms the SPCE detection zone. The flow channel has a height of about 20 micrometers to about 100 micrometers. The flow channel is in fluid communication with an evacuation port to draw the sampled air therethrough. The air-sampling nozzle is recessed within, and connected to, a reflector.

The current invention can utilize an air-sampling nozzle of the type that has a cylinder having an open end and a receiving end. The receiving end of the cylinder has a first side facing the interior of the cylinder, and a second side facing opposite of the interior of the cylinder. At least one borehole penetrates the receiving end, and is in fluid communication with at least one flow channel. The flow channel is preferably disposed and positioned transversely in a recessed area of the receiving end second side. The flow channel is created by the receiving end second side, and a sensing surface on top of a SPCE slide, wherein the area between the two forms the SPCE detection zone. The flow channel preferably has a height of about 1 micrometer to about 1 centimeter with a preferred range of about 20 micrometers to about 100 micrometers. The flow channel carries the air sample across the sensing surface positioned on a reacting surface of the SPCE slide wherein the air sample interacts with the reactive coating. The flow channel preferably has an internal structure suitable for imparting a spiraling motion to the air sample flowing through the channel. The flow channel is in fluid communication with an evacuation port. The evacuation port provides a vacuum to draw fluid through the borehole and the flow channel. The cylinder is recessed within, and adjacent to, an inner focal point of an ellipsoidal reflector. The open end of the cylinder is preferably co-aligned with a foci end of the ellipsoidal reflector's external surface. The sensing surface is positioned at the first focal point of the ellipsoidal reflector.

The current invention can use a fluorescence collection optical system of the type having an ellipsoidal reflector. An emission source is optically positioned at the first foci of the ellipsoidal reflector. The emission source preferably comprises a surface plasmon coupled emission slide and fluorescence material coated on a reacting side of the surface plasmon coupled emission slide. The surface plasmon coupled emission slide is preferably a multilayered slide that is capable of redistributing the emission from the fluorescence material. The surface plasmon coupled emission slide has multiple metallic and dielectric thin layers coated on a transparent substrate. The thickness and the refractive index of the dielectric layer specify the surface plasmon coupled emission angle. The surface plasmon coupled emission slide preferably has a reacting side and a mounting side. A reactive coating is positioned on the reacting side. The reactive coating on the reacting side of the surface plasmon coupled emission slide is comprised of fluorescence material such as CWIC or AFP. There is an emission source deposited on the reactive coating. Preferably, the emission source is a fluorescence material such as CWIC or AFP. The mounting side of the slide is attached to the flat side of a half-ball prism lens with index matching material. Preferably, the index matching material is an optical index matching fluid. The emission source has an analyte transport fluid flowing across and contacting the reacting side of the surface plasmon coupled emission slide. The emission source produces an excited emission light wave, such as the fluorescence, when stimulated. The excited emission light redistributed by the surface plasmon couple emission mechanism is hence allowed to penetrate through the substrate of the surface plasmon coupled emission slide and the index matched half-ball prism lens. The presence of the prism lens allows the excited emission light to exit the prism lens without being trapped by the total internal reflection.

In the fluorescence collection optical system, the excitation assembly contains an excitation filter and a light source. The excitation assembly is affixed to the back of the half-ball prism lens. The excitation filter is positioned between the light source and the half-ball prism lens. The light source provides the stimulus to excite the emission source through the excitation filter and is loosely focused by the half-ball prism lens. A spatial filter is inserted in the optical path to filter any light wave traveling within the ellipsoidal reflector. The spatial filter limits the angle of the reflected emission of the excited light wave, and blocks the undesired light such as the scattered excitation and ambient light. The spatial filter is configured to allow the excited emission light wave to pass through with specified transmission angles ranging from 55 degrees to about 85 degrees. The excitation assembly affixed to the back of the half-ball prism lens blocks any light wave with a transmission angle of less than 55 degrees. An emission detection sensor is positioned at the second foci of the ellipsoidal reflector. The emission detection sensor is preferably a photodetector used in conjunction with an optical filter having a band-pass matched to the emitter. The photodetector is capable of receiving the spatially filtered excited emission light wave through another emission filter. The emission filter provides additional spectral filtering, and increases the signal-to-noise ratio of the collection emission signal.

In an embodiment of the current invention, the need for the use of an index matching fluid is eliminated by using a solid reflector as the reflector. The solid reflector has a top facet and a sidewall selected from the group consisting of ellipsoids, parabola and polynomial curves. The top facet can have a cutout. In place of a sensing slide either the top facet of the solid reflector is used as the sensing slide or a sensing disk is used. If a sensing disk is used, the sensing disk has a diameter, shape, and refractive index closely matching the cut out in the top facet of the solid reflector. So that the gap between the sides of the disk and cutout is about tens to hundreds of microns. The SPCE emission that exit the sidewall of the disk enter the solid reflector and then are reflected by either reflective coating on the exterior of the solid reflector or by total internal reflection.

In yet another embodiment of this invention, light waves from the ellipsoidal, parabolic or polynomial curve reflector are received by a complex lens assembly having the capability to focus a three-dimensional (3D) volume object onto a planar detector with minimized optical aberration such as the effect of chromatic or spherical aberration to achieve specified spatial resolution. In the scope of this application, the 3D object is the real image of SPCE emission of different colors projected by the reflector. The complex lens assembly focuses the 3D distribution of the SPCE emission at the detector with minimized blurring effect. Examples of this complex lens assembly may include but are not limited to camera lens formed by multiple lenses, aspheric lens, and lenses with gradient refractive index distribution.

In yet a further embodiment of this invention, light waves from the reflector are received by an optical fiber bundle taper, which reduces the light ray spatial distribution to match the detector size.

In another embodiment, a method of correlating an intensity distribution change with at least one target analyte to identify the target analyte is provided. The correlation includes the following steps:
  obtaining the intensity distribution change produced by:
    illuminating a reporter with a first wavelength from a light source such that the reporter fluoresces at a second wavelength having an emission angle;
    exposing the reporter to the target analyte such that the analyte reacts with the reporter thereby producing a change to the second wavelength wherein the change to the second wavelength is an intensity change; and
    monitoring the intensity change to thus record the intensity distribution change;
  extracting from the intensity distribution change an intensity-time sensorgram, which comprises the total intensity of the second wavelength versus time;
  selecting one or more baseline time locus on the intensity-time sensorgram before exposing of the reporter to the target analyte and calculating an averaged baseline spectral profile;
  selecting more than one observation time loci on the intensity-time sensorgram;
  determining a static spectral signature at each thus selected observation time locus to produce a set of static spectral signatures;
  determining the target analyte from the set of static spectral signatures.

In a further embodiment of methods according to the current invention, there is provided a method to detect chemical and biological based substances comprising:
  sampling an analyte transport fluid with a collection device, the analyte transport fluid carrying at least one target analyte;
  temperature controlling the analyte transport fluid;
  illuminating at least one reporter positioned in the collection device with an illuminating source at a first wavelength, whereby during illumination the reporter fluoresces at a second wavelength having an emission angle;
  directing the second wavelength to a detector, wherein the directing utilizes a reflector and a high-resolution lens assembly to direct the second wavelength such that the second wavelength is focused into a ring having a radius dependent on the emission angle and wherein the emission angle depends on wavelength such that different wavelengths produce rings having substantially discrete radii;
  detecting the ring with a detector;
  reacting the at least one target analyte with at least one reporter while continuing to illuminate the reporter at the first wavelength thereby producing a change to the second wavelength wherein the change in the second wavelength is an intensity change;
  detecting an intensity distribution change to the ring caused by the intensity change of the second wavelength; and
  correlating the intensity distribution change with at least one target analyte to identify the target analyte wherein the correlation includes the following steps:
    determining total intensity of the second wavelength versus time to produce an intensity-time sensorgram;
    selecting one or more baseline time locus on the intensity-time sensorgram before said reacting of the target analyte to derive and averaged baseline spectral profile;
    selecting more than one observation time loci on the intensity-time sensorgram to calculate the observation spectral profiles;
    determining a static spectral signature at each time locus, wherein the determining the static spectral signature comprises;
    obtaining an intensity profile for the observation time locus along more than one ROI angle for the ring to produce a sector intensity profile, where the sector intensity profile is obtained by local averaging such that the sector intensity profile for each ROI angle represents an average intensity profile along the ROI angle based the region around the RIO angle;
    averaging the sensor or quadrant intensity profiles to obtain the spectral profile; and
    dividing the spectral profile at each observation time locus by the averaged baseline spectral profile to derive the static spectral signatures at each observation time locus;
    processing the static spectral signatures by normalizing and linear transformation and mapping;
    aggregating the thus processed static spectral signatures to generate a temporal-spectral intensity map; and
    analyzing the temporal-spectral intensity map to identify the target analyte.

The invention can be utilized in association with a miniaturized optical emission collection system. The miniaturized optical collection system is contained in a cylindrical housing. The miniaturized optical emission collection system comprises a reverse half-ball prism lens having a flattened vertex on the convex of the reverse half-ball prism lens. The flattened vertex provides optical contact and is index matched to the substrate side of the surface plasmon coupled emission slide. The surface plasmon coupled emission slide has multiple metallic and dielectric thin layers coated on a transparent substrate. The thickness and the refractive index of the dielectric layer specify the surface plasmon coupled emission angle. The surface plasmon coupled emission slide has a reacting side and a mounting side. A reactive coating is positioned on the reacting side.

The reactive coating on the reacting side of the surface plasmon coupled emission slide is an optical reporter or emission source. Preferably, the emission source is a fluorescence material such as CWIC or AFP. The mounting side of the slide is attached to the flattened vertex with index matching material. Preferably, the index matching material is an optical index matching fluid. The emission source has an analyte transport fluid flowing across and contacting the reacting side of the surface plasmon coupled emission slide.

The miniaturized optical emission collection system further comprises a miniaturized air-sampling nozzle on the first end of the cylindrical housing. The miniaturized air-sampling nozzle is comprises a thin disk having a first side exposed to the ambient air, and a second side facing the reacting side of the surface plasmon coupled emission slide. The miniaturized air-sampling nozzle is in fluid communication with a flow channel. The flow channel is formed by the void created between the thin disk and the surface plasmon coupled emission slide. The flow channel is about 20 micrometers to about 100 micrometers in height. The thin disk has a borehole proximate to the center of the thin disk. The thin disk also has an exhaust port proximately to an outer edge. A pump affixed to the exhaust port provides a sufficient pressure drop to create vacuum at the borehole. An air sample containing an analyte is pulled into the flow channel through the borehole. The air sample flows through the flow channel and across a sensing space. The sensing space is proximate to the reacting side of the surface plasmon coupled emission slide, and the flow channel. The flow of the air sample through the flow channel permits the air sample containing the analyte to flow across and react with the reacting side of the surface plasmon coupled emission slide. Preferably, the flow channel is a spiraling flow channel causing the air sample to have a spiraling motion as it flows across the reacting side of the surface plasmon coupled emission slide.

The miniaturized optical emission collection system has an excitation filter. The excitation filter has a first side affixed to the center of a substantially flat surface of a half-ball prism lens. The excitation filter is positioned between the light source and the half-ball prism lens, where the light source provides a stimulus to excite the emission source. The emission source such as the fluorescence material on the sensing surface produces an excited emission light wave when stimulated. The emission light wave penetrates through the surface plasmon coupled emission slide substrate and enters the vertex of the half-ball prism lens with a transmission angle greater than the critical angle. The incidence of the emission light onto the concaved internal surface of the half-ball prism lens results in total internal reflection, which causes the emission light to bounce around the internal surface until it reaches the substantially flat surface of the prism lens. The excited emission light is filtered through a spatial and a spectral filter. A spatial filter is affixed to a substantially flat surface of the half-ball prism lens, and has at least one notch for filtering the desired emission light wave. A spectral filter is positioned to filter the excited light prior to hitting the photodetector. A photodetector sensor that is capable of receiving the filtered emission light wave is used. The entire system is encased within an excitation assembly. The half-ball prism lens is about 10.0 millimeters or less in diameter. The spatial filter is configured to allow the emission light wave to pass through with a transmission angle of about 70 degrees to about 80 degrees.

The invention can be utilized in association with a compact optical emission collection device. The compact optical emission collection device comprises a reverse half-ball prism lens having a flattened vertex, a surface plasmon coupled emission slide, and an air-sampling nozzle. The reverse half-ball prism lens flattened vertex is positioned on the convex of the reverse half-ball prism lens. The flattened vertex provides optical contact, and is index matched to the substrate side of the surface plasmon coupled emission slide. The surface plasmon coupled emission slide has multiple metallic and dielectric thin layers coated on a transparent substrate. The thickness and the refractive index of the dielectric layer specify the surface plasmon coupled emission angle. The surface plasmon coupled emission slide has a reacting side and a mounting side. A reactive coating is positioned on the reacting side. The reactive coating on the reacting side of the surface plasmon coupled emission slide is comprised of an optical reporter or emission source. Preferably, the emission source is a fluorescence material such as CWIC or AFP. The mounting side of the slide is attached to the flattened vertex with index matching material. Preferably, the index matching material is an optical index matching fluid. The emission source has an analyte transport fluid flowing across and contacting the reacting side of the surface plasmon coupled emission slide.

The compact optical emission collection system further comprises a miniaturized air-sampling nozzle on the first end of the cylindrical housing. The miniaturized air-sampling nozzle is comprised of a thin disk having a first side exposed to the ambient air, and a second side facing the reacting side of the surface plasmon couple emission slide. The miniaturized air-sampling nozzle is in fluid communication with a flow channel. The flow channel is formed by the void created between the thin disk and the surface plasmon coupled emission slide. The flow channel is about 20 micrometers to about 100 micrometers in height. The thin disk has a borehole proximate to the center of the thin disk. The thin disk also has an exhaust port proximate to an outer edge. A pump affixed to the exhaust port provides a sufficient pressure drop to create vacuum at the borehole. An air sample containing an analyte is pulled into the flow channel through the borehole. The air sample flows through the flow channel and across a sensing space. The sensing space is proximate to the reacting side of the surface plasmon coupled emission slide, and the flow channel. The flow of the air sample through the flow channel permits the air sample containing the analyte to flow across and react with the reacting side of the surface plasmon coupled emission slide. Preferably, the flow channel is a spiraling flow channel causing the air sample to have a spiraling motion as it flows across the reacting side of the surface plasmon coupled emission slide.

Preferably, the compact optical emission collection device propagates the emission light along the concaved internal surface inside the reverse half-ball prism lens providing an emission light path, which is proximate to the air/prism lens interface. The excitation light source assembly, which includes a light source and an excitation filter, is preferably embedded in the prism lens proximate to a flattened vertex. The excitation light source is preferably positioned such that the emission light path is not obstructed by the assembly. The embedded excitation assembly allows the light receiving assembly, which includes the spatial filter, spectral filter, and the photodetector, to be proximately positioned to the substantially flat surface of the prism lens. A molded optics fabrication process may be used to encapsulate the light source and the excitation filter into a half spherical dome to realize a very compact excitation and collection optical stack.

In one embodiment, a device includes a plurality of reporters disposed on a sensing surface, wherein each one of the plurality of reporters is configured to react with a least one target analyte; a hyperspectral detection module configured to capture hyperspectral image data corresponding to the plurality of reporters; and a controller configured to receive the hyperspectral image data from the hyperspectral detection module; and generate a temporal spectral signature corresponding to each one of the plurality of reporters from the received hyperspectral image data.

In another embodiment, a method includes receiving hyperspectral image data from a hyperspectral detection module, wherein the hyperspectral detection module is configured to capture hyperspectral image data corresponding to a plurality of reporters disposed on a sensing surface, wherein each one of the plurality of reporters is configured to react with a least one target analyte; and generating a temporal spectral signature corresponding to each one of the plurality of reporters from the received hyperspectral image data.

The scope of the invention is defined by the claims, which are incorporated into this section by reference. A more complete understanding of embodiments of the invention will be afforded to those skilled in the art, as well as a realization of additional advantages thereof, by a consideration of the following detailed description of one or more embodiments. Reference will be made to the appended sheets of drawings that will first be described briefly.

BRIEF DESCRIPTION OF THE DRAWINGS

FIG. 1B is a section view of the device from the first embodiment and schematically depicted in FIG. 1A, in accordance with an embodiment of the disclosure.

FIG. 5 schematically depicts the optical layout for the inventive embodiments, in accordance with an embodiment of the disclosure.

FIG. 6 schematically depicts another embodiment of a SPCE sensor arrangement using an ellipsoidal reflector, in accordance with an embodiment of the disclosure.

FIG. 8 schematically depicts the ray tracing for the first embodiment of a SPCE sensor arrangement using an ellipsoidal reflector, in accordance with an embodiment of the disclosure.

FIG. 9 schematically depicts the diagram of a miniaturized SPCE sensor arrangement sensing head, in accordance with an embodiment of the disclosure.

FIG. 10 schematically depicts the diagram of a compact SPCE sensor arrangement sensing head with customized optics, in accordance with an embodiment of the disclosure.

FIG. 11 schematically depicts a thin substrate with reflected and ambient light traversing therethrough, in accordance with an embodiment of the disclosure.

FIG. 12 depicts the SPCE collection waveguide with a capillary, thin substrate and the associated ray tracing, in accordance with an embodiment of the disclosure.

FIG. 13 depicts the test results for the reaction time from a reaction versus the intensity for a given temperature of the analyte, in accordance with an embodiment of the disclosure.

FIG. 16 depicts a test result for Dinitrotoluene (DNT) at the 465 nanometer, 495 nanometer and 515 nanometer wavelengths using the inventive embodiments, in accordance with an embodiment of the disclosure.

FIG. 24 illustrates a screen shot for the 2D temporal-spectral mapping of TNT based on multiple static spectral signatures, in accordance with an embodiment of the disclosure.

FIG. 25 illustrates a screen shot for the 2D temporal-spectral mapping of NT based on multiple static spectral signatures, in accordance with an embodiment of the disclosure.

Embodiments of the present disclosure and their advantages are best understood by referring to the detailed description that follows. It should be appreciated that like reference numerals are used to identify like devices illustrated in one or more of the figures.

DETAILED DESCRIPTION

Figure 1A:
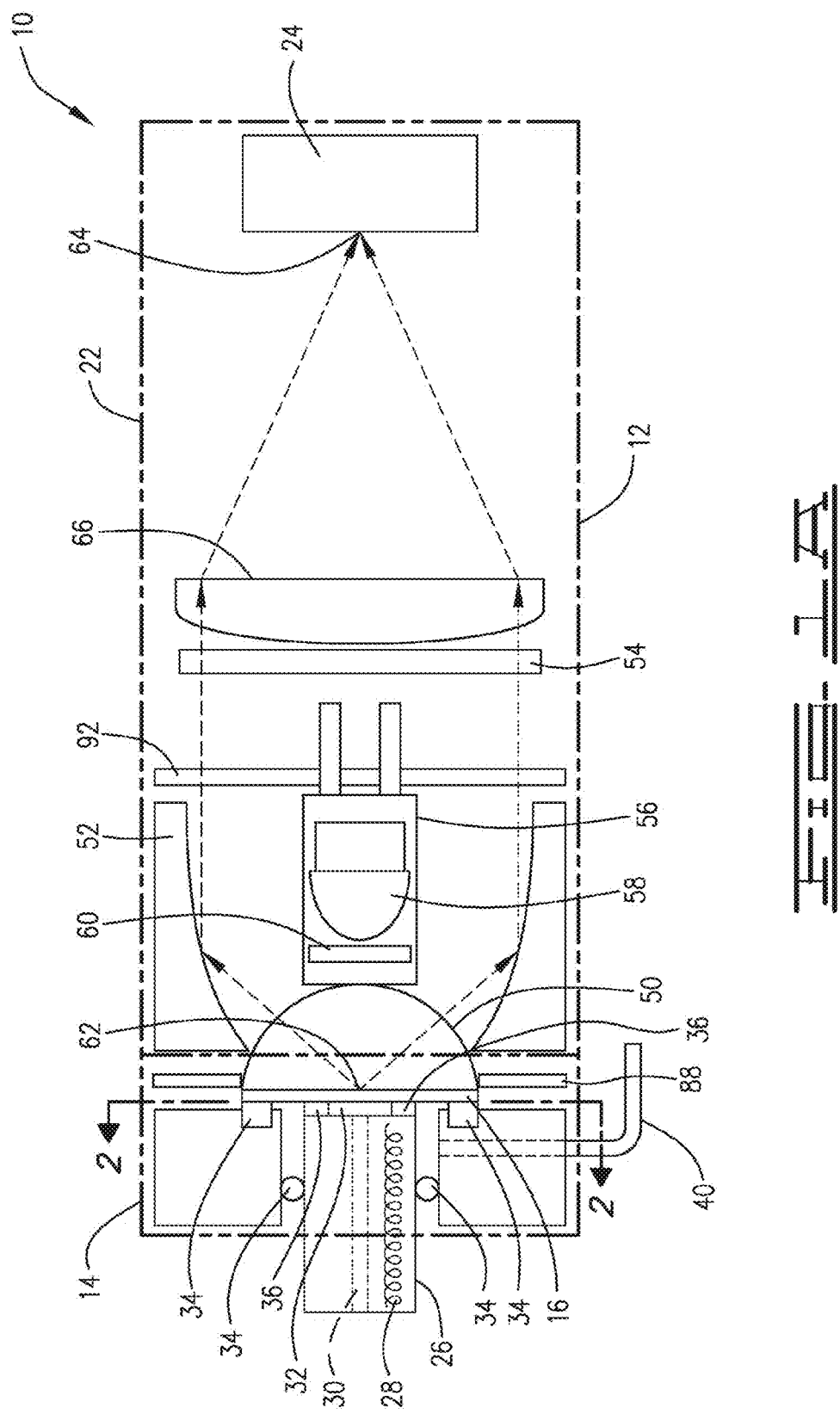
FIG. 1A schematically depicts a first embodiment of a SPCE sensor, in accordance with an embodiment of the disclosure.

This invention provides for an apparatus to optically collect and detect changes in a fluorescing emission resulting from the reaction of an explosive, chemical or biological warfare substance with a reporter material such as a chemical warfare indicating chromophore (CWIC) or amplifying fluorescence polymer (AFP) material. The apparatus comprises three main elements: an air-sampling nozzle, fluorescence collection optics, and a detector/sensor.

I. SPCE Overview

Surface plasmon resonator (SPR) sensors are frequently used as surface binding detection techniques in chemical and biological material sensing applications. Due to the presence of an SPR-capable metal surface, an emission from a CWIC or AFP is coupled into the surface plasmon wave (SPW) and then re-radiated as SPCE via the surface plasmon coupled emission phenomenon. The SPW is a surface-bonded electromagnetic wave propagation in which the free electrons in a conductor, such as coated thin films of noble metals, collectively oscillate in an excited state resulting from stimulation from an excitation light. The SPW excitation condition, such as the incident angle of an excitation light, is highly sensitive to changes in the surface conditions. The interaction of the analyte with the sensing surface is detected by tracking the change in the SPW excitation condition (e.g., SPR angle).

The commonly employed SPR sensor arrangement is the Kretschmann setup. In the Kretschmann setup, p-polarized transverse magnetic mode interrogation light, or excitation light, with wave vector $k_o$ is incident through a high refractive index prism on the thin metal film. The SPW is excited by the incident light when the following phase matching condition is met:

$$n_p k_o \sin \theta = k_{spw}, \text{ and } k_o = 2\pi/\lambda_o,$$

where $k_{spw}$, $n_p$, and $\theta$ are the SPW wave vector, refractive index of prism, and incident angle, respectively. When the excitation light with a wavenumber ($k_o$) is incident with the SPR angle ($\theta_{spr}$), the SPR occurs and reflection is minimized. The SPR angle is very sensitive to the change of the thickness or refractive index deposited on the analyte-side of the metal film.

The present invention uses SPCE as a means to extract the fluorescing emission into a high signal-to-noise zone. SPCE is characterized as the opposite process of the above mentioned SPR energy conversion process. The SPCE-capable surface typically has a transparent substrate (e.g. glass or quartz substrate), and a thin metallic coating on top of the substrate. Preferably, a thin layer of dielectric coating is deposited on top of the metallic layer, which provides a separation between the emitter and metallic surface. Additionally, the dielectric coating provides protection to the thin metallic layer. Instead of converting the incident plane wave energy to the SPW, the spontaneous emission from the spontaneous emitter on the SPCE-capable surface at the proximity of the metal surface is first coupled into the SPW, and then converted into far-field radiation that propagates through the substrate where it is subject to detection.

The SPCE coupling condition is essentially governed by the same SPR phase matching condition at the emission wavelength identified in the equation above. To determine the fluorescence distribution of SPCE, the wave vector $k_o$ is replaced by $k_{spce}$ and $\theta_{spr}$ by $\theta_{spce}$. Due to emission constraints imposed by the phase matching condition, the p-polarized radiation source, or emitter, has a specified spatial emission distribution instead of the more common isotropic emission in the homogeneous media. The specified spatial emission distribution is an emission cone with peak intensity centered at the "SPCE angle", $\theta_{spce}$. The SPCE angle is the transmission angle between the SPCE beam, and the substrate surface normal (toward the substrate).

SPCE has the characteristic of a highly confined emission distribution for p-polarized radiation. Such a focused, highly confined emission distribution allows the fluorescence emission pattern to be collected more efficiently with excellent spatial and polarization filtering options for better discrimination. Usually, free-space spontaneous emission collection efficiency is about 1% due to the isotropic emission pattern. A SPCE-type of system has a spontaneous emission collection efficiency up to 50% to about 60% within the focused SPCE emission cone.

The fluorescence distribution pattern in SPCE is essential for optimizing detection of the explosive, chemical or biological substances reacting with the CWIC or AFP material. The angular SPR reflection curves of the SPCE slides can be used to estimate the fluorescence distribution from the SPCE slide. This has been proven in the literature, and through experimentation.

By way of a non-limiting example, to collect wide-angle emissions, an ellipsoidal reflector or half-ball prism lens is used instead of high numerical aperture optics. By positioning the fluorescent emission at one of the foci of the ellipsoidal reflector, the SPCE signal is focused at the other focal point upon the photo detector sensors. Because of this arrangement, there exists a well-defined SPCE emission angle, which allows a spatial filter mask to be designed by using a ray tracing method as shown in FIG. 8. The ray tracing depicted in FIG. 8 shows the two-dimensional presentation of the example setup and ray tracing results. The spatial filter removes a substantial portion of the unwanted excited light and background noise from the emissions. The light source, or excitation light, illuminates the SPCE slide through the half-ball prism lens. The photodetector is positioned at the other focus to collect the SPCE fluorescing emission through the spatial filter mask. To increase the SNR of the captured emissions, an optional emission filter is used in front of the photodetector to further reduce unwanted light reaching the photo detection sensor.

The SPCE angle for the emission is much greater than the critical angle. The larger emission angle opens up the possibility of using the forbidden light principle to detect an explosive, chemical or biological substance with by using a high SNR technique. One reason for using SPCE is the ability to reject free-space ambient light. The ambient light is only allowed to go into the "allowed light" zone, where the transmission angle is smaller than the critical angle. Essentially, the "allowed light" transmitted is rejected by the "forbidden light" zone. Only through a near-field coupling effect, such as SPCE, can the light propagate into the "forbidden light" zone. This technique has a transmission angle greater than the critical angle. Therefore, SPCE can be detected in the "forbidden light" zone, which has very low background light. This enables sensitive fluorescence detection due to the high SNR of the signal.

II.A Apparatus Background Information

The various reporters suitable for detecting explosives have different types of fluorescent responses when reacted with an analyte. For example, a reporter may initially be non-responsive when excited by a light source, but after reacting with the analyte will fluoresce at a detectable wavelength when excited by that light source. Another reporter may fluoresce when excited by a light source and subsequently experience an increase in fluorescent emission intensity after reacting with the analyte. Such reporters are sometimes referred to as "turn-on" reporters. Another type of reporter may initially emit fluorescent light when excited by a light source, but after reacting with the analyte will then emit less intense or no fluorescent light during the continued excitement from the light source. This type of response to the analyte reaction is called "quenching." The spectrum of the fluorescent light may change after reacting with the analyte, increasing the emission at some wavelengths and/or decreasing the emission at other wavelengths. These changes may be reversible or irreversible depending upon the reporter and/or analyte.

By way of a non-limiting example the following reporters provide some of the responses identified above and herein: (a) CWIC group of reporters are a "turn-on" type of reporter and (b) AFP is a quenching type of reporter. Other types of reporters known to those skilled in the art will also provide responses as identified herein.

The terms "react" and "reacting" used herein indicates actions the reporter takes in response to the presence of an analyte. In the instance of fluorescence, the reporter may change the intensity of fluorescence or emit a different wavelength.

II.B Apparatus

The first preferred embodiment is depicted in FIGS. 1A-5 as an apparatus for an optical collection and detection device 10. Device 10 comprises housing 12 having an input segment 14, sensing slide 16 and optic segment 22 positioned within housing 12. Device 10 provides optical input to detector 24. Preferably, detector 24 is also positioned within housing 12.

Input segment 14 includes air-sampling nozzle 26, heating source 28, capillary 30, and flow cell 32. Input segment 14 samples the air and communicates an analyte transport fluid to sensing slide 16. Analyte transport fluid carries at least one analyte, which is communicated to sensing slide 16. Analyte transport fluid is commonly an air sample of interest obtained in an area of interest, such as at an airport screening location, a shipping container receiving point, or other locations where analytes might appear.

Air-sampling configurations are known in the art as illustrated by U.S. Pat. Nos. 6,558,626, 8,323,576 and WO/2011/112222, all of which are incorporated herein by reference. Suitable air-sampling configurations are described below in relation to the figures; however, other suitable air-sampling configurations will be readily apparent based on the disclosure herein and the afore referenced patent documents.

As shown in FIGS. 1A and 4A, air-sampling nozzle 26 is secured and stabilized within housing 12 by o-ring spacer 34. Spacer 34 is preferably an o-ring that does not outgas or absorb chemical substances. Furthermore, spacer 34 should not react with chemical substances.

Air-sampling nozzle 26 is separated from sensing slide 16 by c-ring 36. C-ring 36 is preferably a material that minimally absorbs analytes. One example of c-ring 36 is using a non-stick material such as Teflon®. C-ring 36 provides a standoff spacing between the end facet of capillary 30 and sensing slide 16. C-ring 36 preferably has a thickness of about 50 to about 75 micrometers. The thickness of c-ring 36 defines the height of flow cell 32. Additionally, c-ring 36 has ring slot 38 providing fluid communication of the analyte transport fluid with sensing slide 16 from capillary 30.

Capillary 30 is disposed within air-sampling nozzle 26. Preferably, capillary 30 is silanized to reduce any analyte consumption during passage of the analyte transport fluid. Capillary 30 receives the analyte transport fluid and communicates it to flow cell 32. Flow cell 32 is in fluid communication with sensing slide 16 and with fluid exit 40. Fluid exit 40 is the exhaust port for air-sampling nozzle 26. The flow of analyte transport fluid through air-sampling nozzle 26 may be assisted by a pump (not shown) attached to fluid exit 40. The preferred flow rate of the analyte transport fluid is about 30 milliliters per minute. The analyte transport fluid is temperature and flow stabilized while being communicated through capillary 30.

Preferably, analyte transport fluid is heated by a sampling unit (not shown) prior to being entering air-sampling nozzle 26. When employed, the sampling unit becomes a first stage or portion of the input segment. Capillary 30 serves as a flow stabilizer and provides a chemically buffered surface between the air sample and the interior of the housing, and a thermal gradient zone from the heated input to sensing slide 16. This approach encourages the analyte adsorption and desorption on sensing surface 18.

An alternative embodiment employs heating source 28 to heat analyte transport fluid while it is being communicated through capillary 30. When using the alternative embodiment, heating source 28 is embedded within air-sampling nozzle 26 and is adapted to heat air-sampling nozzle 26 to a desired temperature. In this alternative embodiment, heating source 28 heats the analyte transport fluid sufficiently so as to provide the analyte transport fluid at sensing slide 16 at a temperature of about 40 degrees Celsius. Preferably, the analyte transport fluid is heated between about 40 degrees Celsius and about 120 degrees Celsius.

As seen in FIGS. 1A-4A, sensing slide 16 is positioned between input segment 14 and optic segment 22. In this embodiment, sensing slide 16 is circularly shaped and has sensing surface 18 oriented towards the flow of the analyte transport fluid. Sensing slide 16 has non-sensing surface 20 oriented away from the flow of the analyte transport fluid.

Figure 2:
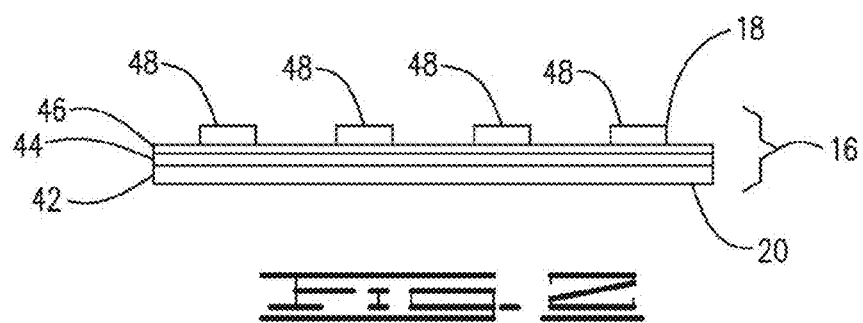
FIG. 2 is a schematic view of the sensing slide taken along line 2-2 of FIG. 1A, in accordance with an embodiment of the disclosure.
Figure 3:
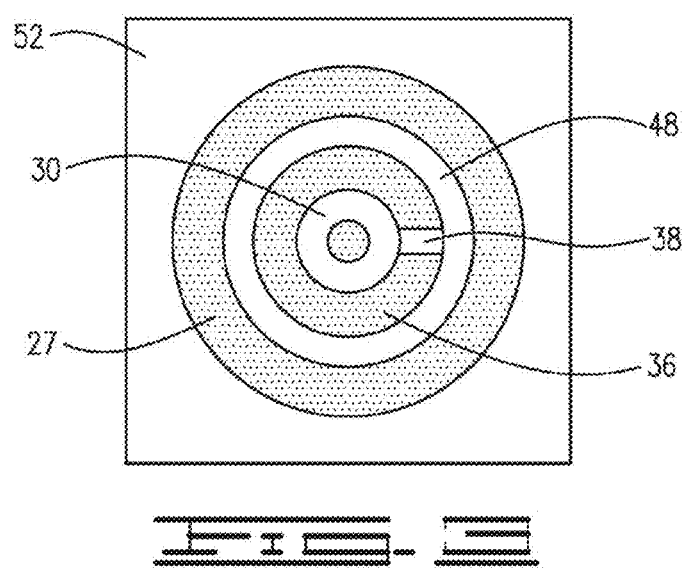
FIG. 3 is a schematic end-view of the capillary and flow cell, in accordance with an embodiment of the disclosure.

Sensing slide 16 is referred to as a "slide"; however, it should be understood that "slide" as used herein includes slides, discs, capillaries and other suitable substrates. Sensing slide 16, shown in FIG. 2, is preferably a glass substrate 42 coated with a plurality of substrate layers on sensing surface 18. First layer 44 is preferably a metallic layer of a film made of a metal or a metal alloy. Examples of metals include silver, gold, platinum, or aluminum. First layer 44 is applied directly to glass substrate 42. Second layer 46 is applied to first layer 44. Second layer 46 is preferably a dielectric overcoat layer. Reporter 48 is applied to the second layer, thereby forming a third layer. Preferably, reporter 48 is a CWIC or AFP and is adapted to react with the analyte carried by the analyte transport fluid.

Preferably, reporter 48 is applied to second layer 46 to form a deposition spot size of about several hundred micrometers in diameter. Reporter 48 may be applied in an array of a plurality of reporters 48 as shown in FIG. 5. When applied in an array of a plurality of reporters 48, each reporter 48 reacts to a different analyte carried in the analyte transport fluid when there is a plurality of analytes present. Preferably, the array of a plurality of reporters 48 is positioned on sensing slide 16. The array is preferably a single array having a total area of about 10 millimeters squared to about 1 millimeter squared or smaller.

As shown in FIGS. 1A and 4A, optic segment includes lens 50, reflector 52, excitation assembly 56 and optical emission filter 54. Excitation assembly 56 further includes light source 58 and optical excitation filter 60. Optical segment 22 is in optical communication with sensing slide 16. Optical segment 22 is also in optical communication with detector 24. As shown in FIGS. 1 and 4A, the optical path flows from light source 58 through excitation filter 60 to reporter 48. The emission from reporter 48 flows through lens 50 to mirror 52 and through emission filter 54 before reaching detector 24.

Lens 50 is attached to sensing slide 16 by an index matching fluid. The index matching fluid eliminates air between lens 50 and sensing slide 16. Lens 50 is shown in FIGS. 1 and 4A. Preferably, lens 50 is a half-ball lens as described herein. When assembled, lens 50 is pressed against sensing slide 16 and c-ring 36 by a lens holder (not shown) formed in housing 12 and held in place by lens mount 88, as shown in FIG. 1A.

In FIG. 1A, reflector 52 is a mirror; however, in general the reflector used in the invention can be reflective grating, transmission grating, prism, substrate with gradient refractive index (GRIN) material, solid reflector, or mirror. The reflector should have a shape or reflecting surface that is an ellipsoidal, parabolic or polynomial curve. Returning, now to FIG. 1A, mirror 52 may be an ellipsoidal, conical or parabolic mirror. When mirror 52 is shaped as an ellipsoid or a parabola, reporter 48 on sensing slide 16 is optically positioned at first foci 62 of mirror 52. When mirror 52 is shaped as a conical mirror, sensing slide 16 is positioned relative to the cone reflector so that any resulting emission (wavelength) is directed toward the receiving area 64 of detector 24. Mirror 52 is aligned with respect to lens 50. Lens 50 is immobilized by lens mount 88 and mirror mounting structure 90, as shown in FIG. 1B.

Referring to FIG. 1B, structural member 92 is shown supporting excitation assembly 56. However, any mounting assembly capable of holding excitation assembly in housing 12 and not block light transmission may be used in this invention.

Excitation assembly 56 is positioned to illuminate reporter 48 with a light wave having a first wavelength from light source 58. As used herein, "light" means both visible and nonvisible electromagnetic radiation capable of producing SPCE. As referred to herein, "wavelength" is understood to refer to both the light wave and the associated wavelength of that light wave. Preferably, light source 58 is a light emitting diode (LED) emitting a light. First wavelength from light source 58 may produce a plurality of wavelengths based upon the type of light source 58 employed. Light source 58 may be any light source 58 that produces a light having a wavelength band capable of producing a response in reporter 48. A non-limiting example of acceptable light sources 58 includes LEDs and lasers. The first wavelength emitting from light source 58 is filtered by excitation filter 60 prior to the first wavelength reaching reporter 48. Excitation filter 60 may be a short band pass filter or a band pass filter. The plurality of wavelengths are also filtered by first optical filter 60 to allow the desired wavelengths to reach reporter 48.

The first wavelength generates fluorescing by reporter 48. The fluorescing reporter 48 emits a second wavelength that is different from the first wavelength emitted from light source 58. When reporter 48 reacts with the analyte, the fluorescing changes and a third, or changed, wavelength is emitted there from. Both the second and third wavelengths are refracted through sensing slide 16 to mirror 52. In practice there may be multiple wavelengths emitted by reporter 48 in response to the first wavelength and when reacting with the analyte.

Mirror 52 reflects the second and third wavelengths towards detector 24. Preferably, prior to the second and third wavelengths reaching detector 24, they are filtered by second optical filter 54. Additionally, an optional focusing lens 66 may be utilized to shorten the optical path length of optical segment 22 by focusing the second and third wavelengths on receiving area 64 of detector 24.

An alternative embodiment is shown in FIG. 4A. For this alternative, sensing slide 16 and lens 50 are replaced with sensing segment 82. Sensing segment 82 has facet surface 84 upon which first layer 44, second layer 46, and reporter 48 are applied. Preferably, first layer 44 is a metallic layer and second layer 46 is a dielectric layer. Reporter 48 is the third layer and is applied to second dielectric layer 46. Sensing segment 82 is preferably a transparent dielectric cylinder. Some non-limiting examples of materials for dielectric cylinder are glass, fused silica, or quartz. In this alternative embodiment, mirror 52 is a conical mirror 52. Sensing segment 82 serves as a cylindrical lens and the emission exits from its side surface 86.

Sensing segment 82 preferably carries at least one reporter 48. If a plurality of reporters 48 are used, reporters 48 are distributed within 3 millimeters from the center of facet surface 84. The shifted reporters 48 provide a shift in reflection of the reacting analyte and reporter 48.

Sensing segment 82 is adapted to be easily removed from the device in a field environment and replaced in the same environment. The field is anywhere the device is employed. For example, sensing segment 82 is adapted to fit within a cartridge (not shown) that locks into housing 12. Alternatively, sensing segment is directly inserted and removed from housing 12 without requiring cartridge. Upon depletion of reporter 48, the cartridge or sensing segment 82 is removed from housing 12 and a new cartridge or sensing segment 82 is inserted into housing 12.

Referring now to FIG. 4B, another embodiment is illustrated. The embodiment of FIG. 4B has some similarity to the arrangement illustrated in FIG. 1A and like components have been designated with like numerals; however, FIG. 4B utilizes imaging optics instead on the non-imaging optics of FIGS. 1A and 4A. Optical segment 22 in FIG. 4B utilizes a high-resolution lens assembly. Generally as used herein a high-resolution lens assembly will be an assembly acting as a lens or series of lens and which result in a high-resolution and more specifically in a spectral resolution of better than (less than) 1 nanometer or an angular resolution of better than (less than) 0.5 degrees. As shown in FIG. 4B, the high-resolution lens assembly is a complex lens assembly 500, such as is utilized in cameras. The complex lens assembly 500 can comprise two or more lens designed to minimize chromatic and/or spherical aberrations. Preferably, the complex lens assembly will comprise a series of lens designed to minimize chromatic and spherical aberration and the blurring effect while focusing at the detector with high-resolution. The complex lens assembly can have the following properties. First, it should be capable of focusing all the points within the field of view and the field of depth on to the planar detector with minimized blurring effect. Minimizing blurring effect is based on the focusing capability and should provide a spectral resolution better than 2 nanometers or an angular resolution better than 0.5 degree. The field of view can have a maximum radius of 50 mm and the field of depth can have a maximum of 20 mm, which are defined by the real image of SPCE distribution projected by the reflector. Secondly, short working distance of the lens assembly is preferred to reduce the size and weight. The preferred working distance is less than 50 mm.

Figure 18:
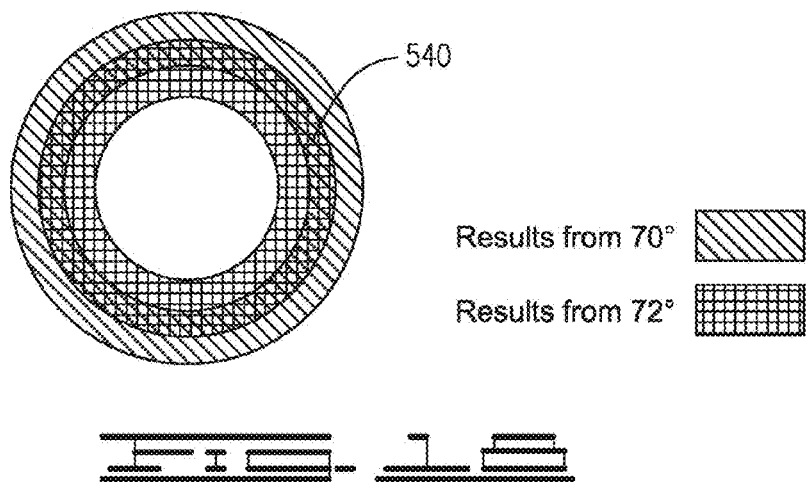
FIG. 18 depicts the overlapping of dispersion patterns for a focusing lens utilized in an SPCE sensor, in accordance with an embodiment of the disclosure.
Figure 19:
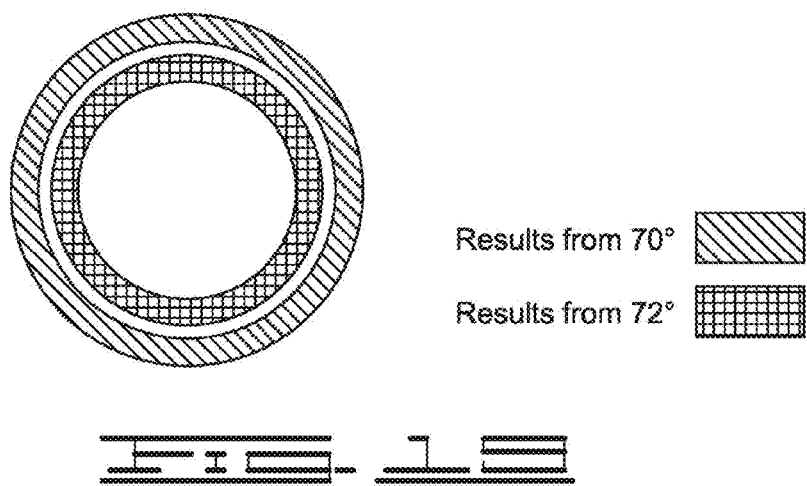
FIG. 19 depicts the separation of dispersion patterns for a complex lens utilized in an SPCE sensor in accordance with the current invention, in accordance with an embodiment of the disclosure.

For the embodiments of FIGS. 1A and 4A, the singular or array emitter size and the angular resolvability of the SPCE light from sensing slide 16 commonly have an angular resolution of about 4 degrees with an emitter size less than 100 µm based on simulation data using 1-inch diameter optics. The resolution degrades as the emitter or array size increases. Accordingly, use of a simple optical focusing lens limits the array size. The complex lens assembly 500 represents an improvement over the simple focusing lens of FIGS. 1A and 4A because the complex lens assembly can be used with multiple emitters in an array format for multiple reporter interrogation with less degrading of resolution. Allowing for multiple reporter interrogation is ideal for identification of target materials. FIG. 18 shows an example shows an example of focusing using parabolic reflector and a simple focusing lens. FIG. 19 shows an example of focusing using a parabolic reflector and a complex lens assembly. The complex lens assembly used an Edmund Optics NT59-870 camera lens and an additional modifying lens in front of the camera lens to capture all the SPCE beams.

As can be seen from a comparison of FIG. 18 and FIG. 19, the complex lens assembly allows an "angular-oriented" focusing effect. As indicated, above the spatial emission distribution for the fluorescing material is cone shaped. Accordingly, the emission pattern detected by detector 24 is a ring shaped patter. FIGS. 18 and 19 illustrate the spatial ring patterns for emissions having wavelengths with SPCE angles of 70° and 72°. The simple focusing lens in FIG. 18 provides a spatial ring with indistinct separation of the different angular emissions or wavelengths resulting in over lapping area 540. With the complex lens assembly in FIG. 19, all emissions with the same emission wavelength from any emitters in the reporter array will all be sorted and focused onto the same ring; thus, the spatial ring can then be translated into spectral ring, and the spectral intensity changes of all reporters in the sensing array can be interrogated simultaneously. The spectral information can be used for detection target classification application.

A high-resolution lens assembly images an object according to its spatial location with great resolution. A simple focusing lens cannot be used to determine the suitable emission angle information due to its limited focusing capability at the off-axis region. The embodiment of FIG. 4B uses a complex lens assembly in an unconventional way allowing it to image the emission angles with excellent resolution without the spatial information of the emission origin(s) itself. With this desired effect, the exact location of the emission origin, even within the array, is now disregarded but the wavelength-specific emission can always be differentiate by the emission angles (or the emission wavelength) as long as there is no significant spectral overlapping or interference by other emission angles. This allows for relaxation of the requirement on the consistent positioning of sensing element with respect to the reflector.

Figure 20:
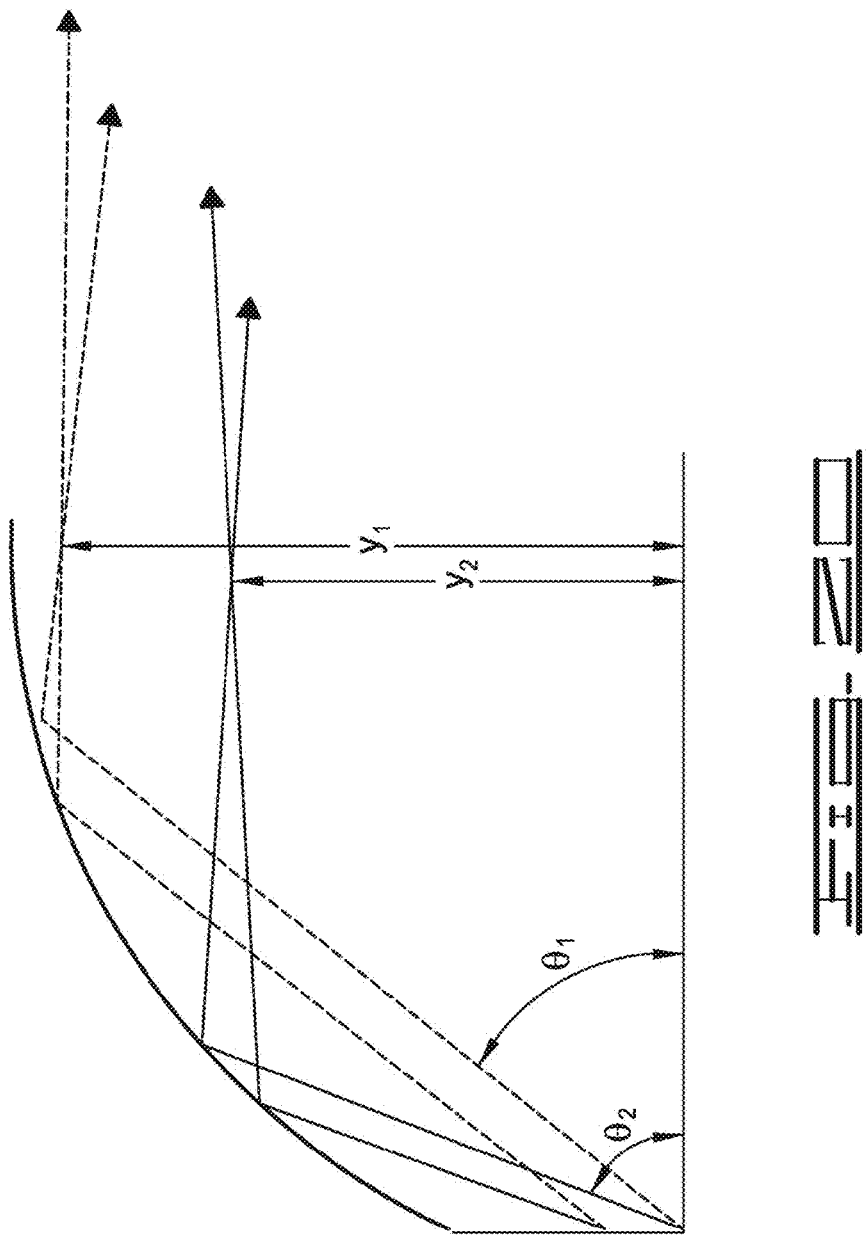
FIG. 20 depicts ray paths of reflection from an ellipsoidal or parabolic reflector, in accordance with an embodiment of the disclosure.

Optically, this "angular-oriented" focusing effect is created by the parabolic reflector 52 or by an elliptical reflector or a reflector with polynomial curved shape. Parabolic reflector 52 translates the angular information into the spatial information so that angular information can now be imaged by complex lens assembly 500. The complex lens assembly does not focus on the origin of the emission but the crossing point created by the parabolic reflector, see FIG. 20.

The parabolic reflector gathers common emission angles and focuses them at different height from the optical axis that the complex lens assembly focuses on. This happens when emissions exit the sensing surface at their angle of emission (SPCE angle) from each point of emission origin along the length of the sample. The beams of the same angle of emission will run parallel to each other. A parabolic reflector 'gathers' the parallel angles of emission and redirects them to a measure of height from the optical axis, thus changing angular information into spatial information. As it is shown in the FIG. 20, the emissions with same emission angle such angle $\theta_1$ and $\theta_2$ will have a crossing point at a height such as $y_1$ and $y_2$ after reflection. The initial angular information ($\theta_1$ and $\theta_2$) is then translated into spatial information ($y_1$ and $y_2$), which then can be recorded using an appropriate optics and an arrayed detector. The translation relation is a one-to-one mapping for both directions. Therefore, the original fine spatial resolution provided by a complex lens assembly is translated into excellent angular/spectral resolution by the parabolic reflector.

An additional advantage of the use of a complex lens assembly includes almost 100% collection of SPCE light and relaxed tolerances on the positioning of the sensing slide.

Referring now to FIG. 4C, yet another embodiment is illustrated. The embodiment of FIG. 4C has some similarity to the arrangement illustrated in FIG. 1A and like components have been designated with like numerals. In optic segment 22, FIG. 4C utilizes a high-resolution lens assembly, which in this is case is a fiber optic taper assembly 510, also called an optical fiber bundle taper. Fiber optic taper assembly 510 is composed of optical fibers with each optical fiber having a taper such that end 512 of the fiber optic taper assembly as a cross-sectional size suitable to capture targeted incoming emissions from sensing slide 16 and the other end 514 of the fiber optic taper assembly has a smaller tapered cross-sectional area suitable to be interrogated by detector 24. The fiber optic taper assembly 510 can be one having a circular aperture with spatial resolution at the tapered end matching to the detector pixel size. The larger end may have radius from 2 to 50 mm and the tapered end has a radius approximately the smaller dimension of the detector. A suitable fiber optical taper is NT55-140 from Edmund Optics. The taper can reduce the object image to a small sized image detectably by high-quality image sensors; accordingly, for this embodiment, detector 24 can be an image sensor allowing for receiving high-quality image data, such as a charge-coupled device (CCD) array.

The embodiment of FIG. 4C is an improvement on that of FIGS. 1A and 4A. The taper allows for greater relaxation in the optical alignment tolerance. The angular/spectral resolution will not be severely restricted or deteriorated by the SPCE focusing optics. Additionally, the physical size of the optical system can also be reduced and the final optical system can be more robust due to less discreet components of the optical system.

Figure 4:
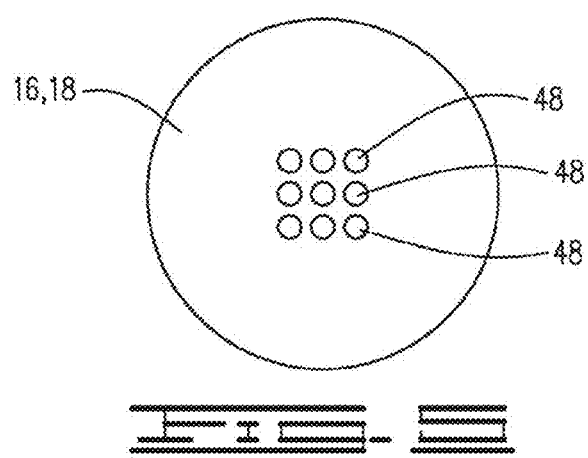
FIG. 4A is a schematic view of a second embodiment of a SPCE sensor, in accordance with an embodiment of the disclosure.
FIG. 4B is a schematic view of another embodiment of a SPCE sensor utilizing a complex lens assembly, in accordance with an embodiment of the disclosure.
FIG. 4C is a schematic view of yet another embodiment of a SPCE sensor utilizing an optical taper, in accordance with an embodiment of the disclosure.
FIG. 4D is a schematic view of still another embodiment of a SPCE sensor utilizing a solid reflector, in accordance with an embodiment of the disclosure.
Figure 4D:
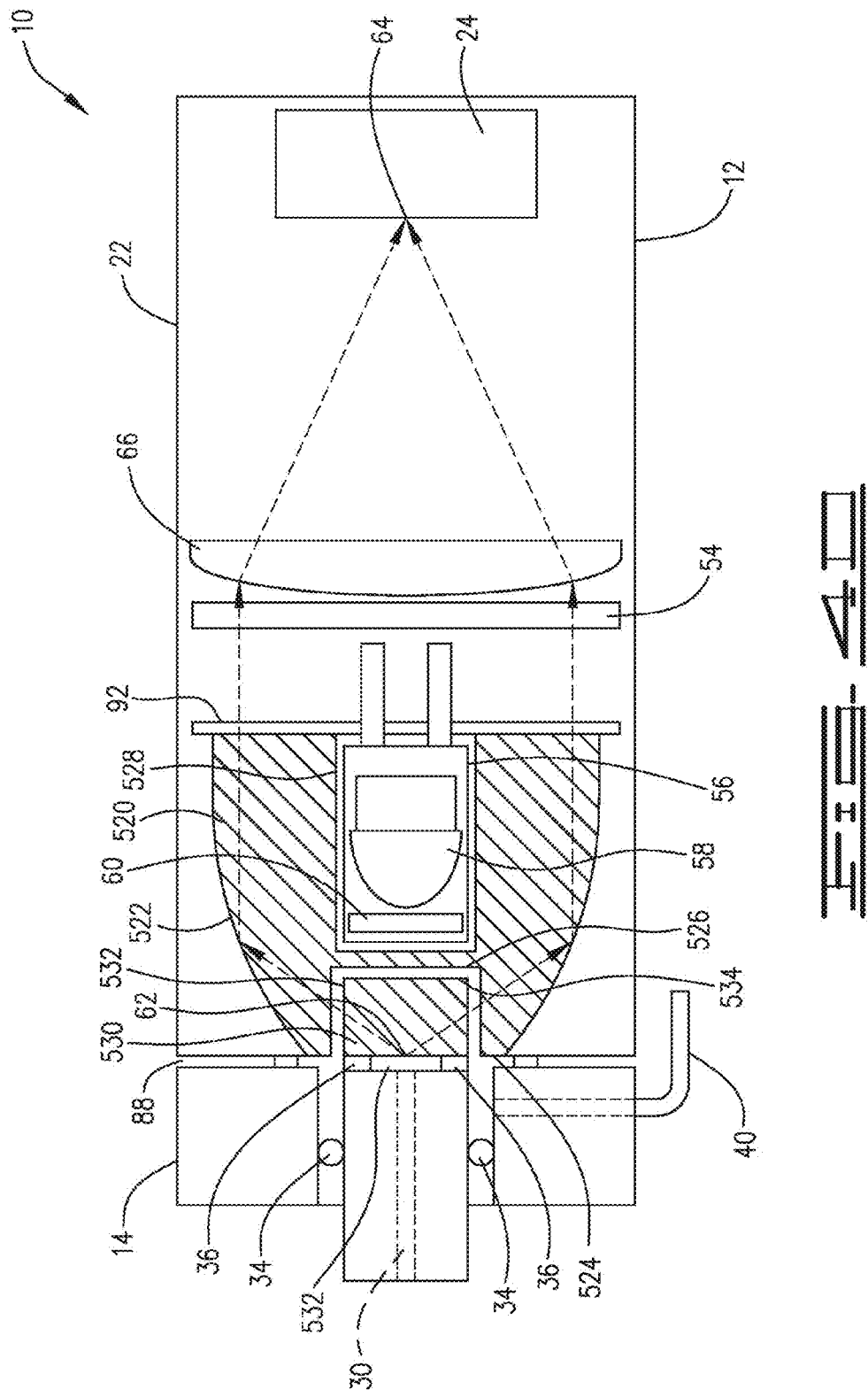

Referring now to FIG. 4D, still another embodiment of the invention is illustrated. This embodiment uses solid reflector 520 for directing emissions from the reporters to the detector. As used herein, a solid reflector refers to a reflector wherein made up of an optically transparent material wherein the light travels through the material from a viewing area and reflects at the sidewall by either total internal reflection or by a reflective coating on the outside of the sidewall. Solid reflector 520 is made of optically transparent material and has a top facet 524. The solid reflector has a shape selected from the group consisting of ellipsoids, parabola and polynomial curves. In a preferred embodiment the solid reflector has the aforementioned shape because it has a sidewall 522 selected from the group consisting of ellipsoids, parabola and polynomial curves. The top facet 524 has a cutout 526. Reporters are applied to a sensing disk 530, similarly to the description for applying the reporters on sensing slide 16. The sensing disk 530 and cut-out 526 have closely matching diameters and shapes, preferably substantially the same diameter and shape so that the gap between the sides of the disk and cut-out is in the tens to hundreds of microns, preferably from 10 microns to 500 microns, more preferably 25 microns to about 100 microns. The sensing disk 530 is positioned in cutout 526 such that the reporters applied to disk 530 are substantially located at viewing area for the solid reflector, which is located at first foci 62. The SPCE emission that exit the sidewall 532 of disk 530 enter solid reflector 520 and then are reflected by either a reflective coating on the exterior of sidewall 522 of the solid reflector or by total internal reflection. The semi-collimated SPCE rays will then be collected by the focusing optics 66 and detector 24. The internal bottom face 534 of the sensing disk and the sidewall 532 of the sensing disk may be treated to reduce surface partial reflections, which cause stray light interference. While the solid reflector 520 and the sensing disk 530 can be made of the same or different material, it is preferable that the solid reflector 520 and the sensing disk 530 be made of materials with similar or closely matched refractive index, such as glass or optical grade polymeric materials. In one embodiment the refractive indexes of the solid reflector and sensing disk will be substantially the same or they will have the same refractive index. In a further embodiment the solid reflector and sensing disk will be the same material and have the same refractive index.

It is a current advantage that the sensing disk be separate and not an integral part of the solid reflector. This allows for the replacement of the sensing disk without the need to replace the solid reflector. However, it is within the scope of the invention that the sensing disk 530 could form an integral part of the solid reflector 520 with the reporters being position on the top facet 524 such that they are substantially located at the foci.

Additionally, while the solid reflector 520 is illustrated in FIG. 4D with lens 66, it should be understood that it could be used with a complex lens assembly such as described in relation to FIG. 4B or with a fiber optic taper as described in relation to FIG. 4C.

It is an advantage of this embodiment that it alleviates the need for the use of an index matching fluid. In this embodiment, the SPCE rays exiting from the sidewall 532 of sensing disk 530 immediately enter solid reflector 520, which has a similar refractive index to sensing disk 530. Accordingly, the SPCE rays will maintain their original propagation direction (i.e. direction cosine) with only a small lateral shift. The shifting amount is related to the transmission angle and the air gap. With a very small gap, the shift can be negligible.

Figure 7:
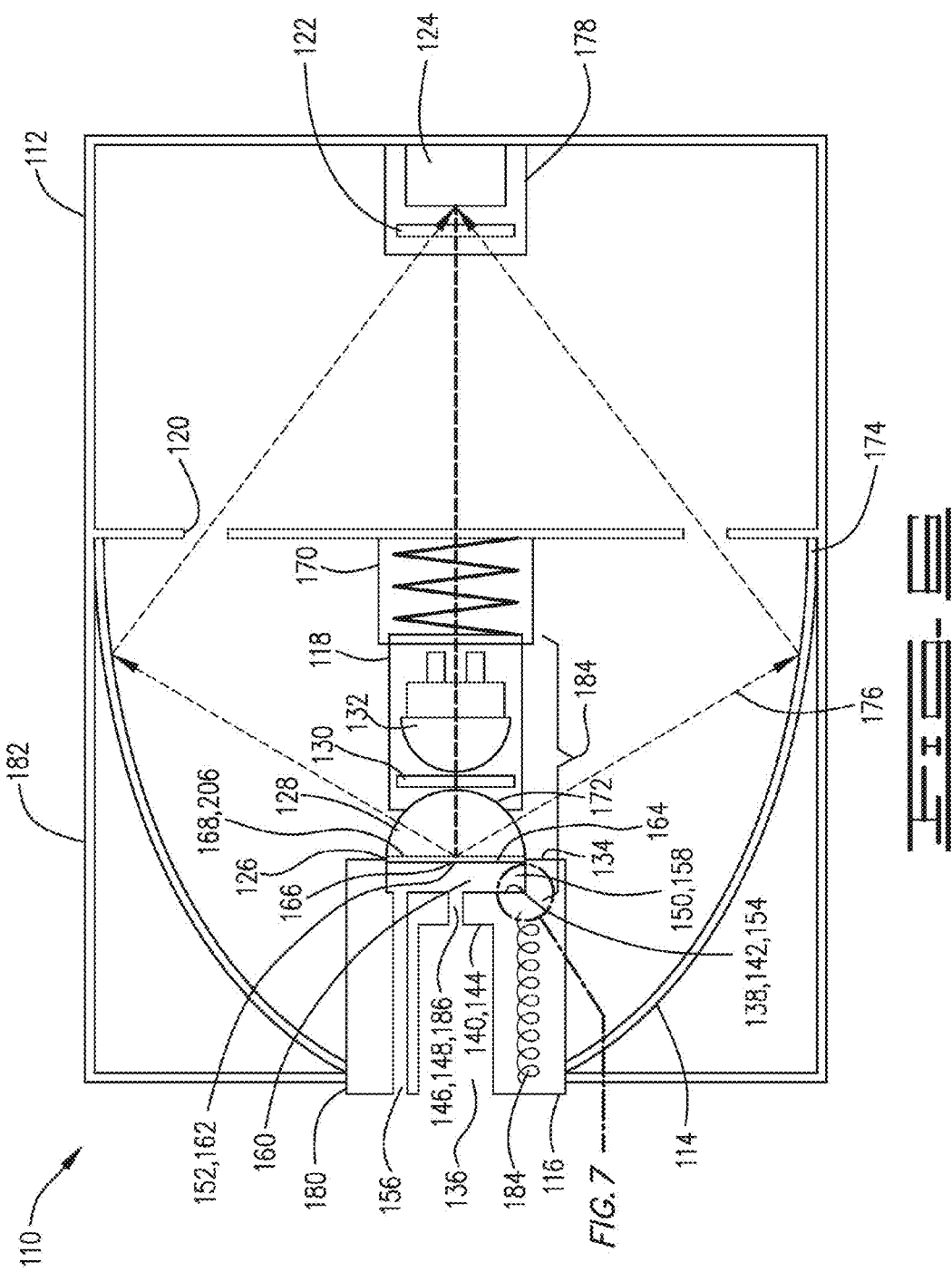
FIG. 7 schematically depicts a spiraling flow channel used in the first, second and third embodiments, in accordance with an embodiment of the disclosure.
Figure 3:
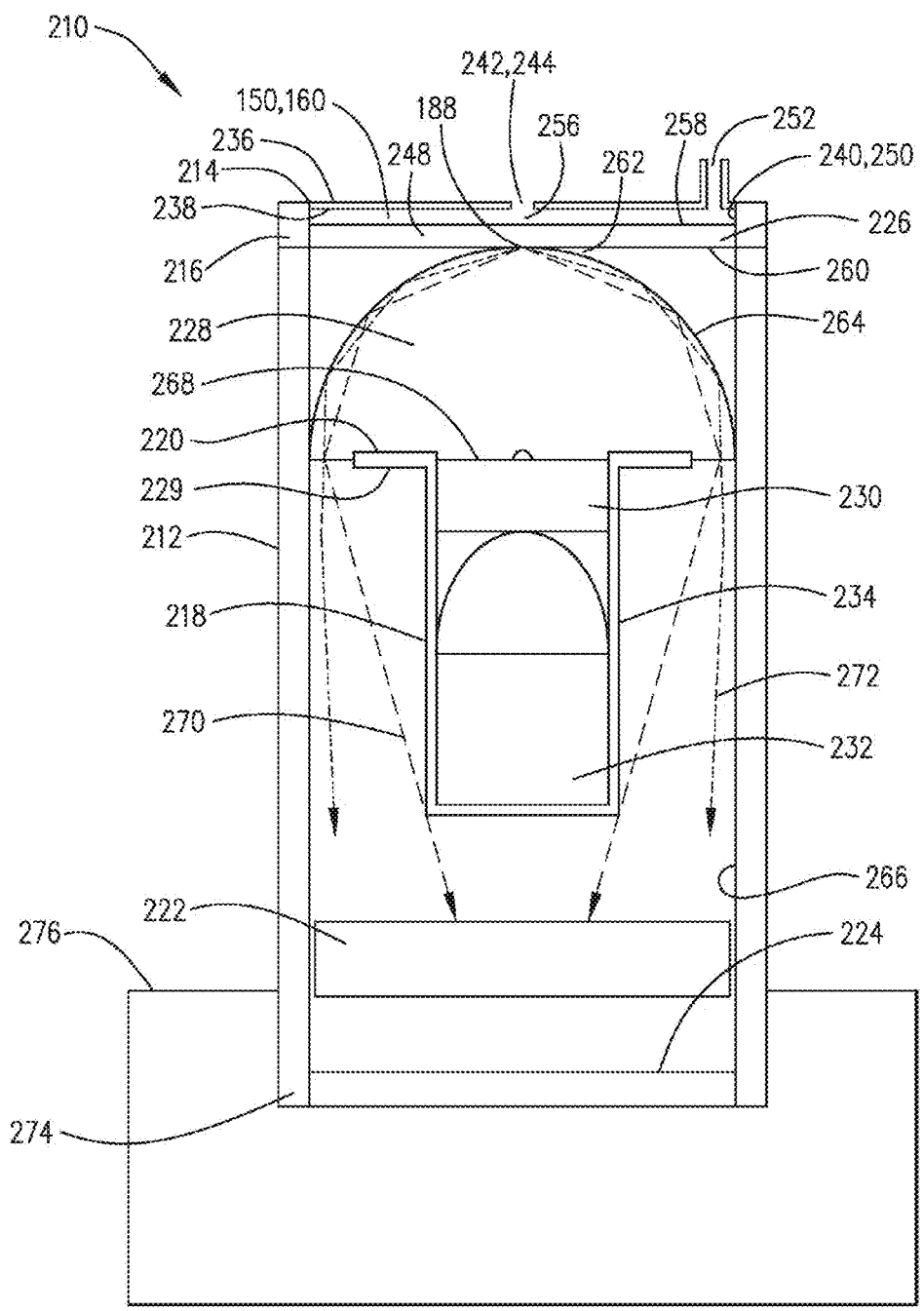

Referring to FIGS. 6-8, in another embodiment, optical collection and detection device 110 includes housing 112 having an input segment 180, sensing slide 126 and optic segment 182 positioned therein. Input segment 180 includes air-sampling nozzle 116, heating source 184, borehole 146, and flow cell or channel 150. Input segment 180 is in fluid communication with sensing slide 126. Optical segment 182 includes mirror 114, excitation assembly 118, spatial optical filter 120 and emission optical spectral filter 122. Optical segment 182 is in optical communication with sensing slide 126. Photodetector 124 is in optical communication with optical segment 182.

Sensing slide 126 and half-ball prism lens 128 are held in place by air-sampling nozzle 116 and excitation assembly 118. Excitation assembly 118 includes an excitation filter 130 and a light source 132, which is preferably a light emitting diode (LED). However, light source 132 may be any light source cable of generating fluorescence in the reaction of an analyte with CWICs or AFPs, collectively referred to as reporters 48. For example, light source 132 may include LEDs and solid-state lasers.

Using air-sampling nozzle 116, input segment 180 samples an air mixture and provides device 110 with the analyte transport fluid containing an analyte. Air-sampling nozzle 116 communicates the analyte transport fluid through borehole 146. There may be a plurality of analytes in the analyte transport fluid. FIG. 6 depicts air sample nozzle 116 positioned within housing 112 and part of ellipsoidal mirror 114.

In this embodiment, air-sampling nozzle 116 includes cylinder 134, cavity 136, open end 138, receiving end 140, first borehole 146, flow channel 150 and exhaust port, or evacuation port 156. Receiving end 140 of cylinder 134 has first side 144 facing receiving end 140 and second side 142 oppositely positioned. Cylinder 134 has first borehole 146 penetrating center 148 of receiving end 140, and providing fluid communication between cavity 136 and flow channel 150.

Flow channel 150 is formed by open end 138 of air-sampling nozzle 116, and the sensing surface 152 of sensing slide 126. Flow channel 150 is preferably disposed and positioned in recessed area 154 of second side 142. Flow channel 150 preferably has a height of about 20 micrometers to about 100 micrometers. Flow channel 150 preferably has an internal structure 158 suitable for imparting a spiraling motion to fluid flowing through flow channel 150 such that the fluid flows through sensing space 160, and across sensing slide 126 with an extended, or elongated, interaction path length between the air sample and sensing slide 126. Internal structure 158, which is used to form the flow channel 150, may be machined onto the surface of second side 142.

In operation, cavity 136 is an initial air sample collection zone. Borehole 146 provides fluid communication between sensing space 160, as defined herein, and cavity 136. Evacuation port 156 provides fluid communication between sensing space 160 and the atmosphere or a suitable small pump (not shown). Evacuation port 156 provides a conduit for a vacuum to draw fluid through first borehole 146 and flow channel 150. In the embodiment depicted in FIG. 6, the small pump creates a vacuum, and draws the sampled air through first borehole 146 and across sensing slide 126.

SPCE detection zone, or sensing space 160, is located in flow channel 150 between second side 142 and sensing surface 152 of sensing slide 126. Sensing surface 152 is the location where an analyte reacts with reporter 48. Upon sensing surface 152, reporter 48 is illuminated with first light wave 192 propagating first wavelength 194 from light source 132. First wavelength 194 causes reporter 48 to fluoresce. Reporter 48 emits a fluorescing, or second, wavelength 196. The reacting analyte and reporter 48 create a change in second wavelength 196 and emit a changed, or third, wavelength 198.

Sensing slide 126 is also referred to as a "SPCE slide," and is preferably a glass or quartz substrate coated with a plurality of layers of substrate. In the preferred embodiment, sensing slide 126 is similar to sensing slide 16 depicted in FIG. 2. Sensing slide 126 carries first layer 44 and second layer 46. Preferably, first layer 44 is a metallic layer and second layer 46 is a dielectric layer. Reporter 48 is a third layer applied on top of second layer 46. Sensing slide 126 is preferably adapted to provide a SPCE angle between about 55 to about 85 degrees.

First layer 44 is about 20 nanometers to about 70 nanometers. If silver is employed, it is preferably about 50 nanometers. However, first layer 44 may be other SPR-capable metals such as aluminum, gold, or platinum. The choice depends upon the desired fluorescence wavelengths.

Second layer 46 in one specific implementation is silicon dioxide ($SiO_2$) with a thickness of about 5 nanometers to about 30 nanometers. Poly-vinyl alcohol (PVA) has also been successfully tested as the dielectric layer. The SPCE emission angle is dictated by the dielectric thickness. Thus, the thickness of second layer 46 is dependent on the desired application.

Sensing slide 126 has a reacting side 162 and a mounting side 164. Reacting side 162 is sensitized with reporter 48 and fluoresces when illuminated. Sensing space 160 is positionally located immediately above sensing slide 126 on reacting side 162. Reacting side 162 is also positioned to be at first focal point 166 of ellipsoidal mirror 114. Mounting side 164 is affixed to flat portion 168 of a half-ball prism lens 128 with an optical index matching fluid 206. Optical index matching fluid 206 is required to remove any unintended air gap between half-ball prism lens 128 and sensing slide 126. Half-ball prism lens 128 is extended into area 154, and is retained by excitation assembly 118. Half-ball prism lens 128 may also be another shape of a prism having a cylindrical symmetry.

Spring loaded cylinder 170 exerts a force that presses excitation assembly 118 against half-ball prism lens 128 curved side 172. Spring loaded cylinder 170 also exerts a force that presses against spatial filter 120. As indicated, excitation assembly 118 also carries excitation filter 130 and light source 132. Excitation filter 130 is positioned between half-ball prism lens 128 and light source 132 to block light of undesired wavelength. Excitation assembly 118 also functions as a part of spatial filter 120 and blocks emissions from the sensing surface 152 of sensing slide 126, which transmits through half-ball prism lens 128 with a transmission angle smaller than 55 degrees.

Optional spatial filter 120 is transversely affixed across open end 174 of ellipsoidal mirror 114, as shown in FIGS. 6 and 8. Spatial filter 120 blocks transmitted light emissions 176, and removes a substantial portion of the unwanted fluorescing emission and background noise. Spatial filter 120 is adapted to provide transmission angles within a tunable range. The tunable range is typically between about 55 degrees to about 85 degrees. Ellipsoidal mirror 114 focuses transmitted light emissions 176 to a detection assembly 178. Detection assembly 178 carries emission spectral filter 122 and photodetector 124. Emission spectral filter 122 is a spectral band-pass or long-pass filter used to further improve the SNR of the detection signal by blocking the undesired noise or out-of-band fluorescence signal. Optical collection device 110 operates with and without emission spectral filter 122. However, emission spectral filter 122 is employed when a higher SNR is desired.

The combination of the foregoing components of optical collection device 110 is preferably sized to provide a portable device. In this embodiment, the current size of the combination of components is about 3.5 inches (8.9 centimeters) wide, by about 5 inches (12.7 centimeters) tall.

Another embodiment illustrated in FIG. 9, provides a miniaturized optical collection device 210. In this embodiment, miniaturized optical collection device 210 comprises a housing 212. Housing 212 carries air-sampling segment 216 as part of the structure. Housing 212 further carries thin disk 214, excitation assembly 218, spatial filter 220, emission spectral filter 222, and photodetector 224. Sensing slide 226 and half-ball prism lens 228 are suspended by the air-sampling segment 216 and excitation assembly 218. Lens 228 may also be a half-ellipsoidal shaped prism (not shown). Excitation assembly 218 carries excitation filter 230 and light source 232, which is preferably a light emitting diode (LED). However, light source 232 may be any light source cable of generating fluorescence to include LEDs and solid-state lasers. Excitation assembly 218 is preferably contained in excitation housing 234.

Referencing FIGS. 7 and 9, air-sampling segment 216 of housing 212 further comprises thin disk 214, which has first side 236 and second side 238. Thin disk 214 is preferably affixed to inner wall 240. Thin disk 214 is a thin rigid structure and has a borehole 242 in the middle 244 and an exhaust port 252 near inner wall 240. Thin disk 214 and sensing slide 226 define flow channel 150. Flow channel 150 is preferably positioned across recessed area 250 of second side 238. Flow channel 150 preferably has a height of about 20 micrometers to about 100 micrometers. Flow channel 150 is in fluid communication with the first borehole 242 and exhaust port 252. Exhaust port 252 is in fluid communication with first borehole 242 and flow channel 150. In the embodiment, a small pump (not shown) creates a vacuum and draws the sampled air through first borehole 242, into flow channel 150, across sensing surface 248, and out through exhaust port 252. Flow channel 150 preferably has internal structure 158 suitable for imparting a spiraling motion to fluid flowing through flow channel 150 such that the fluid flows through sensing space 256, and across sensing slide 226 with an extended, or elongated interaction path length between the air sample and sensing slide 226. Internal structure 158, which is used to form flow channel 150, may be machined onto the surface of second side 238.

Sensing slide 226 has reacting side 258 and mounting side 260. Sensing slide 226 is affixed to half-ball prism lens 228 flattened tip 262 with an index matching fluid. By flattening the tip of half-ball prism lens 228, proper contact is made with sensing slide 226 on mounting side 260. This allows the emission from reacting side 258, on top of sensing slide 226, to be coupled into half-ball prism lens 228 with a large transmission angle due to the large SPCE angle. The emission enters into half-ball prism lens 228, and is guided by curved prism surface 264 through the "total internal reflection" and exits half-ball prism lens 228 when it reaches the cut-off facet 229 of half-ball prism lens 228. Fluorescing emission ray 270 in half-ball prism lens 228 is guided along curved prism surface 264 through a series of total internal reflections. Fluorescing emission ray 270 is then further reflected by polished reflective inner surface 266, and finally received by a photodetector 224 through an emission spectral filter 222. Preferably, half-ball prism lens 228 has an optical quality surface finish to keep the optical losses low. The surface profile does not need to be perfectly spherical as long as the local incident angle exceeds the critical angle.

Half-ball prism lens 228 is transversely positioned across housing 212, and in contact with inner wall 240. Excitation assembly 218 is held by set screws (not shown) affixed to housing 212, and pressed against the substantially flat surface 268 of the half-ball prism lens 228. Excitation housing 234 is preferably opaque, and prevents light from light source 232 to leak onto photodetector 224. Light source 232 is optically in communication with the reacting side 258 sensitized with fluorescence material on top of sensing slide 226. Light source 232 is the excitation light source that generates the optical stimulation of the fluorescence material.

Spatial filter 220 is transversely affixed to the substantially flat surface 268 of half-ball prism lens 228. Spatial filter 220 blocks a substantial portion of the remaining excitation light 272 and background light. Spatial filter 220 is configured to allow the fluorescing emission ray 270 with the desired SPCE angle to pass through with an angle of transmission (i.e. the SPCE angle) of about 70 degrees to about 85 degrees. The angle of transmission, or SPCE angle, is tuned to a range between about 70 degrees to about 85 degrees by adjusting the thickness of the second layer 46 of sensing slide 226, which is the dielectric coating layer. With such a large emission angle, the total internal reflection on the internal curved prism surface 264 of half-ball prism lens 228 is useable to guide the fluorescing emission ray 270 to photodetector 224. Spatial filter 220 is a ring shape spatial filter with an inner diameter matching the diameter of the excitation filter 230 so that excitation light 272 from excitation source 232 can penetrate through it. The outer diameter of the spatial filter 220 is smaller than the diameter of half-ball prism lens 228, so that the desired fluorescing emission ray 270, propagating along curved prism surface 264, may also penetrate it and reach the photodetector 224.

Inner wall 240 of housing 212 has reflective surface 266 sufficient to propagate fluorescing emission ray 270 to photodetector 224. Optional emission spectral filter 222 is positioned between spatial filter 220 and photodetector 224. Optional emission spectral filter 222 is used to further improve the SNR of the detection signal by blocking the undesired excitation light or the background light.

In the embodiment shown in FIG. 9, second end 274 of housing 212 is positioned in detector base 276 with a photodetector 224 positioned within inner wall 240. Housing 212 preferably has external dimensions of about 1.0 centimeter wide and about 2.5 centimeters tall.

Another embodiment provides a compact optical collection device as depicted in FIG. 10. The compact optical collection device 310 is contained within housing 312. Housing 312 incorporates air-sampling segment 316 as part of the structure. Housing 312 also carries thin disk 314, excitation assembly 318, spatial filter 320, emission spectral filter 322, and photodetector 324. Sensing slide 326 and molded half-ball prism lens 328 are held in place by the air-sampling segment 316 and excitation assembly 318. Molded half-ball prism lens 328 also carries excitation filter 330 and light source 332, which is preferably a light emitting diode (LED). However, light source 332 may be any light source cable of generating fluorescence to include LEDs and solid-state lasers. Molded half-ball prism lens 328 may also be a half-ellipsoidal shaped prism (not shown).

Referencing FIG. 10, air-sampling segment 316 portion of housing 312 further comprises thin disk 314, which has first side 338 and second side 340. Thin disk 314 is preferably affixed to inner wall 342. Thin disk 314 is a thin rigid structure and has borehole 344 in middle 346 and an exhaust port 354 near inner wall 342. Thin disk 314 and sensing slide 326 define flow channel 348. Flow channel 348 is preferably disposed and positioned across recessed area 352 of second side 340. Flow channel 348 preferably has a height of about 20 micrometers to about 100 micrometers. In the embodiment, a small pump (not shown) creates a vacuum and draws the sampled air through first borehole 344, into flow channel 348, across sensing surface 350, and out through exhaust port 354. Flow channel 348 preferably has internal structure 356 suitable for imparting a spiraling motion to fluid flowing through flow channel 348 such that the fluid flows through sensing space 358, and across sensing slide 326 with an extended, or elongated, interaction path length between the air sample and sensing slide 326. Internal structure 356, which is used to form flow channel 348, may be machined onto the surface of second side 340.

In the compact optical collection device, sensing slide 326 has reacting side 360 and mounting side 362. Sensing slide 326 is affixed to molded half-ball prism lens 328 flattened tip 364 with an index matching fluid. By flattening the flatten tip 364 of molded half-ball prism lens 328, proper contact is made with sensing slide 326 on mounting side 362. This allows the emission from reacting side 360 on top of sensing slide 326, to be coupled into molded half-ball prism lens 328 with a large transmission angle due to the large SPCE angle. The emission enters in molded half-ball prism lens 328 and is guided by curved prism surface 366 through the "total internal reflection" and exits molded half-ball prism lens 328 when it reaches the cut-off facet 329 of molded half-ball prism lens 328. Fluorescing emission ray 372 in molded half-ball prism lens 328 is guided along curved prism surface 366 through a series of total internal reflections, and then further reflected by the polished inner surface 368, and finally received by a photodetector 324 through an emission spectral filter 322. Preferably, molded half-ball prism lens 328 has an optical quality surface finish to keep the optical losses low. The surface profile does not need to be perfectly spherical as long as the local incident angle exceeds the critical angle.

Molded half-ball prism lens 328 is transversely positioned across housing 312, and in contact with inner wall 342. Molded half-ball prism lens 328 is held by set screws (not shown) affixed to housing 312. Excitation filter 330, and light source 332 are preferably embedded and encapsulated within molded section 334 of molded half-ball prism lens 328. This combination may be fabricated by using customized glass for molded half-ball prism lens 328 to accommodate excitation filter 330, and light source 332, or by using customized light source 332 encapsulation process with embedded excitation filter 330 and molded half-ball prism lens 328. Light source 332 preferably has opaque substrate 336 which will prevent the light from leaking to photodetector 324. Light source 332 is optically in communication with the reacting side 360 sensitized with reporters 48 on top of sensing slide 326. Light source 332 is the excitation light source to generate the optical stimulation of the reporters 48.

Light source 332 provides first wavelength 327 to reporter 48. Reporter 48 emits a fluorescing second wavelength 372. 374. Reporter 48 is adapted to react with the analyte and create a changed second wavelength 374.

Spatial filter 320 is transversely affixed to the substantially flat surface 370 of molded half-ball prism lens 328. Spatial filter 320 blocks a substantial portion of the remaining excitation light 327 and background noise. Spatial filter 320 is configured to allow the second wavelength 372 and changed second wavelength 374 with desired SPCE angle to pass through with an angle of transmission (i.e. the SPCE angle) of about 70 degrees to about 85 degrees. The angle of transmission, or SPCE angle, is tuned to a range between about 70 degrees to about 85 degrees by adjusting the thickness of the dielectric coating layer, which is the second layer 46 of the sensing slide 326. Sensing slide 326 is similar to the sensing slide shown in FIG. 2. With such a large emission angle, the total internal reflection on the internal curved prism surface 366 of molded half-ball prism lens 328 is useable to guide the fluorescing emission ray 372 to the photodetector 324. Spatial filter 320 is a disk shaped spatial filter with its outer diameter slightly smaller than the diameter of molded half-ball prism lens 328, so that emission lights 372 and 374 from reporter 48 propagating along curved prism surface 366 may penetrate it and reach photodetector 324.

Inner wall 342 of the housing 312 has a polished inner surface 368 sufficient to propagate fluorescing emission ray 372 to photodetector 324. Optional emission spectral filter 322 is positioned between spatial filter 320 and photodetector 324. Optional emission spectral filter 322 is used to further improve the SNR of the detection signal by blocking the undesired excitation light or background light. Housing 312 preferably has external dimensions of about 1.0 centimeter wide and about 1.0 centimeter tall.

In yet another embodiment, illustrated in FIG. 12, waveguiding device 410 has SPCE multilayer structure 418 coupled with waveguiding capillary structure 420. Waveguiding capillary structure 420 is a high refractive index substrate. Most of the fluorescence emitting from a thin layer of reporter 416 coated on a high refractive index substrate 420, penetrates therein and propagates within the capillary wall 437. Emission 424 is coupled through the SPCE multilayer structure 418 and propagates into capillary wall 437 as rays, or emission 424, and to detector 426.

FIG. 11 depicts an example of optical reporter 416 coated on a dielectric substrate without SPCE multilayer structure 418. In FIG. 11, reporter 416 is coated on transparent dielectric substrate 421. Most of emission 422 penetrates first surface 428 of substrate 421 with transmission angles distributed from zero degrees to the critical angle ($\theta_C$). Emission 422 entering substrate 421 with a transmission angle less than the critical angle $\theta_C$, further penetrates second surface 430 of substrate 421 if first surface 428 and second surface 430 are parallel. Therefore, such an emission will not be detected by the emission detector at the end facet 434 of substrate 421.

However, some of emission 424 entering substrate 421 with a transmission angle equal to or greater than critical angle $\theta_C$ will be bounced between first surface 428 and second surface 430 due to total internal reflection until it reaches end facet 434 of substrate 421, which is usually perpendicular to first surface 428 and second surface 430 of substrate 421. The local incident angle of emission 424 at end facet 434 is $90°-\theta_C$, which will still be greater than the critical angle $\theta_C$, if the critical angle $\theta_C$ is less than 45 degrees. This is usually the case if substrate 421 is made of a glass or an even higher refractive index material in the gaseous environment. In this case, emission 424 at end facet 434 will experience another total internal reflection and is therefore completely trapped inside substrate 421.

Referring back to FIG. 12 and as discussed herein, the SPCE fluorescing emissions have an emission peak at the deep "forbidden light" zone. The transmission angle $\theta_T$, or the SPCE angle, propagating into substrate 420 under SPCE multilayer structure 418, is greater than 45°, and hence exits end 444 towards detector 426. Since SPCE signal is a deep forbidden light, and the ambient light 436 will be rejected out of the forbidden light zone, a high SNR SPCE signal can be acquired with this configuration.

As such, an addition of waveguiding capillary structure 420 optically coupled to the aforementioned SPCE multilayer structures 418 on inner surface 440 will form a highly selective fluorescence collection device. Waveguiding capillary structure 420 is preferably an optically transparent glass capillary having a borehole 438. Waveguiding capillary structure 420 has a multilayer sensing surface 431 deposited on the inner surface 440. The first end 442 of waveguiding capillary structure 420 is facing the ambient environment, and second end 444, opposite of first end 442, is facing light detection assembly 446. Light detection assembly 446 preferably comprises spectral filter 448 and detector 426.

An excited light wave is produced when an excitation source (not shown) simulated a fluorescence material on the sensing surface. The light detection assembly 446 is at the second end 444 of waveguiding capillary structure 420 to detect the emissions. To provide airflow, a pump (not shown) is preferably connected to the borehole 438 and is adapted to pull a sufficient air sample through the borehole 438. The air sample, and/or an analyte in the air sample, interacts with reporter 416 on the multilayer sensing surface 431 of capillary structure 420.

Preferably, multilayered sensing surface 431 is a transparent substrate and a metallic thin layer capable of supporting surface plasmon resonance at the emission wavelength. Additionally, the multilayered sensing surface is a dielectric thin layer to protect the metallic layer and to position the emitter away from the metallic layer. Preferably, a fluorescence emitting material is applied to the dielectric layer. The fluorescence emitting material is reporter 416, which is preferably a reporter material for a CWIC or AFP type of material.

FIG. 12 shows the ray tracing of ambient light 436 (in dashed beams) and SPCE light emission 424 (in a solid beam) emitted by reporter 416 on top of multilayer sensing surface 431 within waveguiding capillary 420. Only the SPCE signal emission 424 can be reflected and guided effectively by capillary inner surface 440 and capillary outer surface 450, and propagated to detector assembly 446 at the second end 444 by waveguiding capillary structure 420. The ambient light 436, which is rejected out of the forbidden zone, will not be guided effectively through capillary structure 420. Therefore, as an alternative propagator for SPCE signal emission 424, waveguiding capillary structure 420 is used to achieve a very good signal-to-noise ratio.

Inner surface 440 of waveguiding capillary structure 420 is coated partially or completely with SPCE multilayer structures 418, which are thin metallic and dielectric coatings. The reactive side, or multilayer sensing surface 431, is further sensitized with a fluorescence reporter 416, which generates the SPCE signal emission 424. Borehole 438 of capillary 420 is used as flow channel 452 to deliver a gaseous sample to the sensitized reactive side, or multilayer sensing surface 431. Waveguiding capillary 420 is simultaneously used for both sample delivery and optical signal waveguiding.

III. Method for Collecting Optical Emissions

With continued reference to the drawings and the descriptions of apparatuses 10, 110, 210, 310, and 410, the current invention also provides an improved method for collecting optical emissions from reactions with explosive, chemical or biological substances. In particular, the collection method of the current invention is not limited to a laboratory, but may be carried out in a field environment such as a field of combat, airport/seaport security, sporting events, border control, and any other security point or checkpoint.

By way of example, only one of the embodiments is used to define the method for collecting optical emissions. The same method is applicable for the other embodiments. In the method of use, optical collection device 110 is assembled and prepared for use. After optical collection device 110 is prepared for use, and prior to operation of photodetector 124, the pump is turned on and tested to ensure operation within desired parameters. In general, small field portable pumps, which may be battery powered, are used to provide an airflow rate of about 30 $cm^3$/min to about 1000 $cm^3$/min. In operation, an air sample is drawn in through air-sampling nozzle 116, by the pump connected to optical collection device 110 via tubing. The pump permits adjustment of the flow rate to accommodate operational conditions. Preferably, an in-line flow meter (not shown) monitors air flow through air-sampling nozzle 116 and communicates with a microprocessor or other suitable device to maintain a consistent flow of air through air-sampling nozzle 116 by controlling operation of the pump. During operation, the pump draws the air sample over a heated surface (like the surface of nozzle 26, capillary 30, or nozzle 116) thus heating air sample to a temperature of about 80 degrees Celsius to about 102 degrees Celsius.

When used in the field, optical collection device 110 is operated by placing air-sampling nozzle 116 in an air stream or in the vicinity of an object of interest. With the pump operating, an air sample enters air-sampling nozzle 116. Based upon the field requirements, the operator adjusts the pump to control the sample flow rate to accommodate operational conditions.

The air sample is drawn in through first borehole 146, and subsequently passes over sensing slide 126. The flow channel 150 directs the air sample through internal structure 158 in a swirling method across sensing slide 126. The air sample traverses sensing slide 126 for an extended time and path length, while the explosive, chemical or biological substance, or analyte in the air sample, reacts with the fluorescence material positioned on the reactive side of sensing slide 126. Preferably, the flow rate is adjusted to allow the explosive, chemical or biological substance to interact with the fluorescence material with sufficient time, i.e. within less than 3 seconds. Additionally, the fluorescence material preferably returns to the non-reactive state in less than 60 seconds after the exposure to an explosive, chemical or biological substance has ceased.

Light source 132 emits an excitation light that optically interrogates the fluorescence material. As the fluorescing material interacts with an explosive, chemical or biological substance, the fluorescing material undergoes a change in intensity, emission spectrum, or SPCE angle of the transmitted light emission 176. As recognized by those skilled in the art, this reaction, which could be physisorption, chemisorption, or a change in chemical structure changes the emission characteristics.

Transmitted light emission 176 propagates through ellipsoidal reflector 114, or half-ball prism lens 228 or 328, for the other embodiments. The resulting change in the light emission is detected by photodetector 124, which transmits an electrical signal to a data acquisition device (not shown) associated with or incorporated into apparatus 110.

Optional spatial filter 120, and emission spectral filter 122, eliminates unwanted light in the "forbidden light" zone as transmitted light emission 176, the fluorescing emission, propagates to photodetector 124. Detection of the change of transmitted light emission 176 by photodetector 124 positioned within optical collection device 110 signals a positive test for explosive, chemical or biological substances. In one embodiment, the transmitted light emission 176 is transmitted through a high-resolution lens assembly to photodetector 124. The intensity distribution change is detected by the photodetector 124 and can be correlated to the analyte as described below.

Thus, the method of the current invention does not require prior processing of an air sample to detect explosive, chemical or biological substances. Rather, the current invention permits immediate processing of air samples suspected of containing explosive, chemical or biological substances. The current invention also provides an improved and effective means to collect the optical emission from the reactive side of a SPCE slide with enhanced SNR by taking advantage of the forbidden light detection principle, spatial filtering, and spectral filtering. Accordingly, the methods and apparatus of the current invention are well suited to a field environment where rapid testing of suspected samples for trace amounts of explosive, chemical or biological substances is critical. In an alternative embodiment, sensing slide 16 is removable and replaceable in the field.

The current invention also provides a method for detecting chemical based substances within an analyte transport fluid such as air. A sample of the analyte transport fluid is taken using optical collection and detection device 10. The analyte transport fluid carries at least one target analyte.

In the preferred embodiment, light source 58 illuminates reporter 48. Light source 58 produces a wide spectrum. The wide spectrum is filtered to a first wavelength that illuminates reporter 48, thereby creating fluorescence emitting from reporter 48. The emitted fluorescence is at a second wavelength. The reporter may emit a plurality of wavelengths, each with a distinct wavelength. The plurality of wavelengths is referred to as wavelength bins. The second wavelength or second wavelength bins are detected by detector 24.

Reporter 48 is reacted with the target analyte. The reaction occurs while reporter 48 is continuously illuminated with the first wavelength. The reaction produces a changed second wavelength, or third wavelength, that is different from the second wavelength. The reacting target analyte and reporter 48 may also emit a number of wavelength bins, each with a distinct wavelength. The changed second wavelength or changed second wavelength bins are detected by detector 24.

Alternatively, the reaction of reporter 48 with the target analyte produces a change in the intensity of the second wavelength. Since the type of fluorescence change is known for each reporter analyte pairing, detector 24 is adapted to measure the change in intensity of second wavelength or second wavelength bins, or to detect the resulting changed second wavelength or changed second wavelength bins.

Preferably, the first wavelength is filtered by first optical filter 60 and the second and changed second wavelengths are filtered by second optical filter 54. The filtering process by excitation optical filter 60 and emission optical filter 54 removes a portion of the wavelength before further propagation occurs. In operation, first optical filter 60 filters out the bandwidth from first wavelength to allow only the desired wavelength to illuminate reporter 48. Second optical filter 54 filters out all of the other bandwidths except the designed bandwidth for the particular reporter 48 and a particular analyte.

In one embodiment of the method, it may be desirable to heat the analyte transport fluid. A non-limiting example of a range of temperatures for heating is about 40 degrees Celsius to about 120 degrees Celsius. Heating beyond about 120 degrees Celsius will also provide increased benefits. The heating may occur outside of air-sampling nozzle 26 or a heating element may be embedded within or attached to air-sampling nozzle 26. The step of heating the analyte transport fluid to a set temperature is determined by the particular reporter 48 and the particular analyte.

IV. Alternative Deployment Methods

One alternative method for determining a single analyte uses the first embodiment device 10 with a single reporter 48 and a single detector 24. This alternative provides for an increase in the performance in sensitivity of about five (5) to about eight (8) times over existing technologies. Additionally, this alternative provides for a faster response time of about two (2) times over existing technologies.

Figure 17:
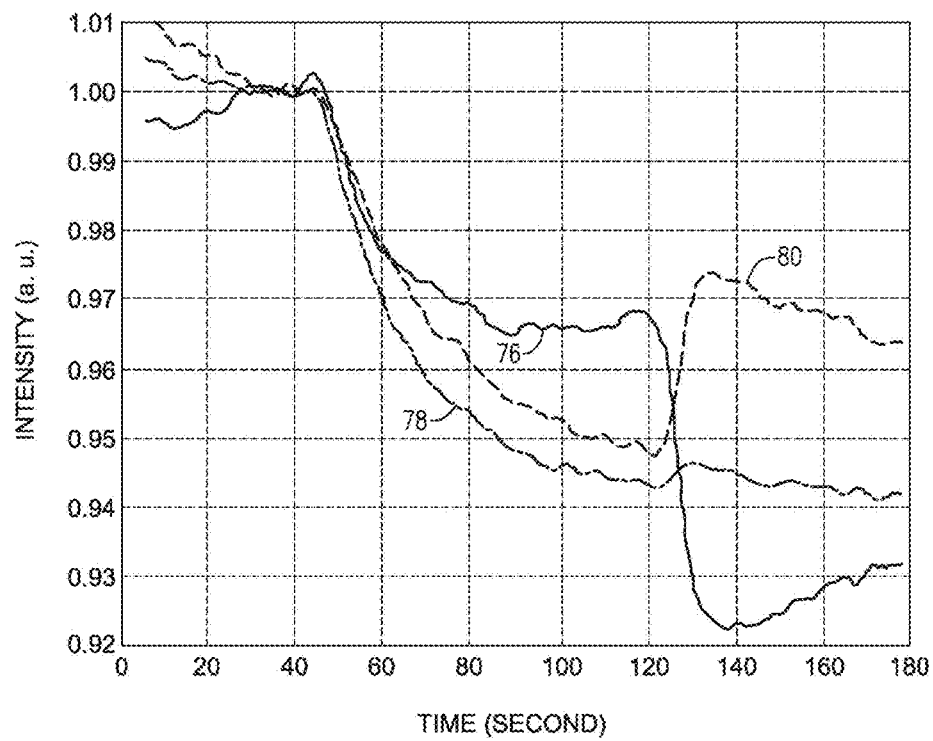
FIG. 17 depicts a test result for Nitroglycerin (NG) at the 465 nanometer, 495 nanometer and 515 nanometer wavelengths using the inventive embodiments, in accordance with an embodiment of the disclosure.

Another embodiment for discriminating analytes against a fluorescence spectrum uses the first embodiment with a single reporter 48 and an array detector 24. Using array detector 24 provides for the detection of the second and changed second wavelength bins. Comparing the intensity change between the wavelength bins, the type of target analyte can be determined, as depicted in FIGS. 17 and 18, and described below. The intensity changes among wavelength bins are correlated with a particular target analyte. It is known to those skilled in the art that fluorescence will fluctuate due to ambient temperature changes and generate unwanted optical interference.

By comparing the intensity changes among the wavelength bins, the ambient temperature effect is determined and produces at least one data point of optical interference information. The ambient temperature induced optical interference information allows for adjusting detection software to remove unwanted optical interference information.

Yet another embodiment for discriminating a plurality of analytes uses the first embodiment with a plurality of reporters 48 and an array detector 24. Using array detector 24 provides for the detection of the second and changed second wavelength bins. Comparing the intensity change between the wavelength bins, the type of target analytes can be determined by correlating the intensity changes with a particular target analyte. The addition of multiple reporters provides for the detection of multiple target analytes in a single sampling process.

V. Method of Correlating Intensity Distribution Change

With continued reference to the FIGS. 4B, 4C and 4D and the descriptions of those apparatuses, the current invention also provides an improved method for correlating an intensity distribution change with at least one target analyte to identify the target analyte.

In accordance with the method, an intensity distribution change is obtained for the emissions from a reporter. Broadly, the intensity distribution change is produced by illuminating a reporter with a first wavelength from a light source such that the report fluoresces at a second wavelength and recording the resulting intensity distribution of the second wavelength and any changes to it over a period of time. When the reporter is exposed to a target analyte, the analyte reacts with the reporter thereby producing an intensity change to the second wavelength. The intensity of the second wavelength is monitor and recorded, which generally will be on computer readable media.

More specifically, the intensity distribution can be obtained by the apparatuses described in relation to FIGS. 4B and 4C. Accordingly, an analyte transport fluid within a collection device is sampled. As described above, the analyte transport fluid can be temperature controlled, generally by heating, such that it is at an appropriate temperature for sampling and interaction with the reporter, as described below. The collection device has at least one reporter positioned therein. The reporter is illuminated with a first wavelength, which results in the reporter fluorescing at a second wavelength. That is, the reporter will fluoresce at a second wavelength in response to the illumination at the first wavelength. Generally, the second wavelength will be a narrow band of wavelengths peaking at a specific wavelength.

The second wavelength emissions from the reporter are directed to a detector. As described above for FIGS. 4B and 4C, the directing can be accomplished by use of a reflector and a high-resolution lens assembly. This combination provides an "angular-oriented" emission having a high angular resolution, which is advantageous for the analysis and target analyte detection. Accordingly, the second wavelength is focused into a ring having a radius dependent on its emission angle. As discussed above, the emissions from the reporter are conical in shape. This conical emission is redirected by the reflector and the high-resolution lens to the detector such that the cross-sectional ring of the conical emission is detected and recorded, similar to the illustration in FIG. 19, which shows a simplified emission distribution for two wavelength bands. The radius of the ring depends on the emission angle for the conical emission. The emission angle depends intern on the emission wavelength such that different wavelengths produce rings having substantially discrete radii. The apparatus should be arranged so that at least a portion of the ring can be detected by the detector, Generally, it is preferable that substantially the entire ring is detected with the detector and the method herein will be described in accordance with substantially the entire ring being detected.

When the transport fluid contains at least one target analyte, the target analyte reacts with at least one of the reporters thus producing a change to the second wavelength. The change is an intensity change and generally will represent a quenching or reduction in the intensity of the second wavelength. The data from the detector is recorded to produce the intensity distribution change over a time period of time. The period of time preferably begins, at latest, just prior to the introduction of the target analyte to the reporter and preferably is sufficient to include all the changes in the second wavelength caused by the target analyte.

Figure 21:
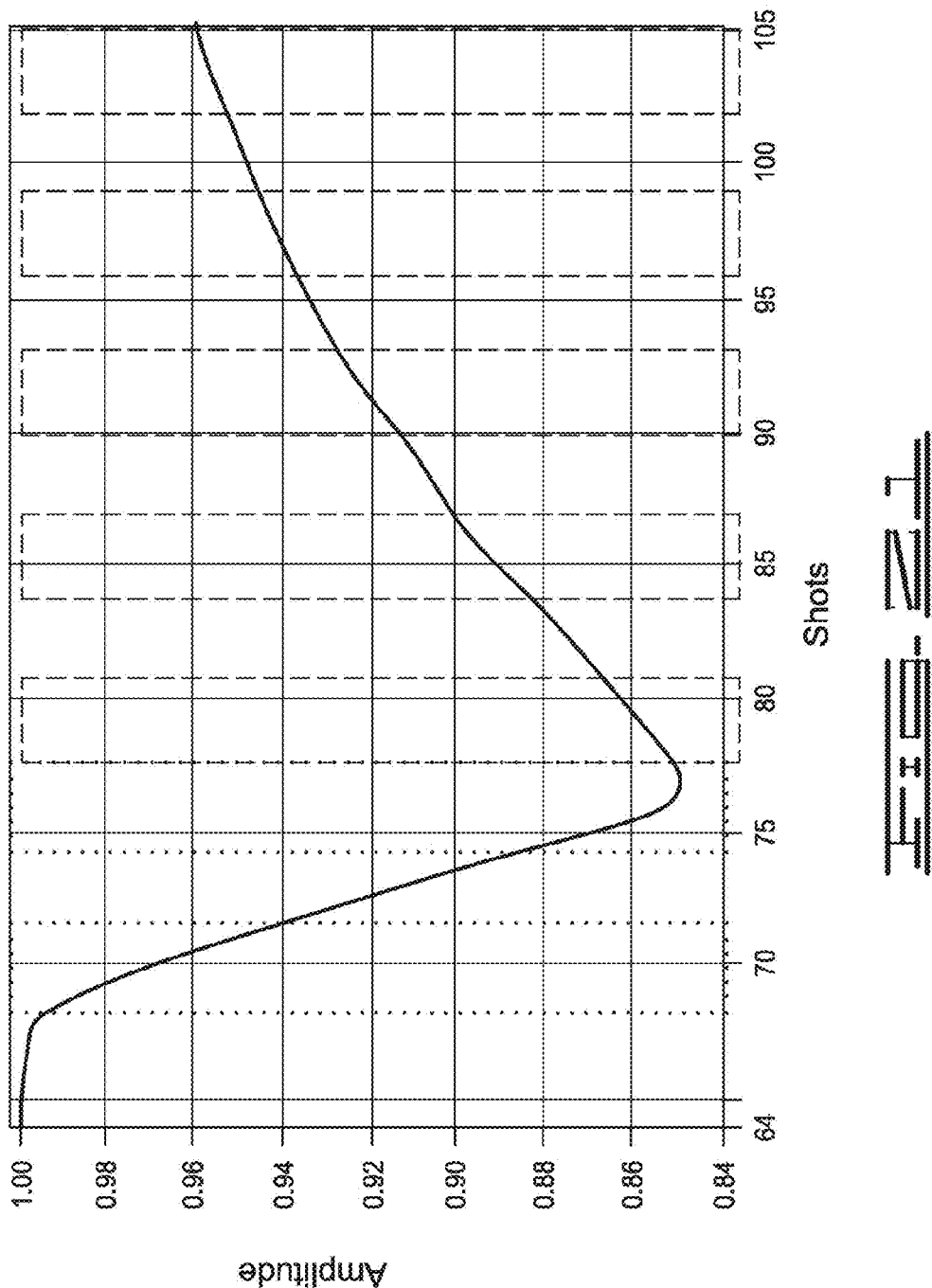
FIG. 21 illustrates an exemplary intensity-time sensorgram, in accordance with an embodiment of the disclosure.

From the intensity distribution change data an intensity-time sensorgram is extracted. The intensity-time sensorgram comprises the total intensity of the second wavelength, i.e. the total intensity of the emission ring, versus time. An example of the intensity-time sensorgram can be seen in FIG. 21 where the total fluorescence intensity within the annulus region or ring is plotted. In FIG. 21 the dotted and dashed lines represent selected time stamps or time locus. The dotted lines mark the time locus during the first stage or onset of the sensing event and the dashed lines mark the second stage or recovering stage of the sensing event. The separation of the stages is usually chosen at the moment where an intensity slope changes its sign. For rather monotonic sensorgrams with no apparent deflection point, the half point is chosen. It should be noted that each locus on the intensity-time sensorgram illustrated in FIG. 21 represents a total intensity reflective of the annulus or ring of florescence intensity at a discrete point in time.

From the intensity-time sensorgram, one or more baseline time locus is selected. The baseline time loci are selected from before the introduction of analyte to calculate the average baseline spectral profile. Additionally, more than one observation time loci are selected from the intensity-time sensorgram. The observation time loci are selected from during the sensing event, such as the dotted and dashed lines illustrated in FIG. 21.

Next a static spectral signature is determined at each observation time locus to produce a set of static spectral signatures. Generally, the static spectral signature can be obtained for an observation time locus by first obtaining an intensity spectral profile for the observation time locus and then dividing the spectral profile by the spectral profile at the baseline time locus to derive the static spectral signature, which is then used to generate the normalized spectral profile.

A spectral profile for a baseline time locus or an observation locus can be obtained by taking the intensity profile along any fixed azimuthal angle of the ring, called the Region of Interest (ROI). In theory the intensity profiles among the ROI angles are redundant because of the ring symmetry. Thus, the ROI can be averaged to increase the spectrum signal-to-noise ratio. In practice, due to the inevitable optical misalignment and asymmetry in the optical system, the intensity profiles among the ROI angles will have variations. Accordingly, it is preferred that local averaging is used within the neighboring ROI angles. For example, four ROI angle groups could be used from 80° to 140°, 140° to 200°, 200° to 260° and 260° to 320°. The intensity across the annulus region for the ROI angle groups can be averaged to arrive at a four composite sector intensity profiles representing an average intensity profile along the ROI angles 80°, 140°, 200° and 260°. These sector intensity profiles are then averaged to arrive at the spectral profile. The spectral profiles of each of the observation time locus are then normalized as described above to arrive at the static spectral signature. While the above example for local averaging uses four ROI angles, it should be understood that it is within the scope of the invention to use a greater or lesser number of ROI angles to arrive at the spectral profile.

Figure 22:
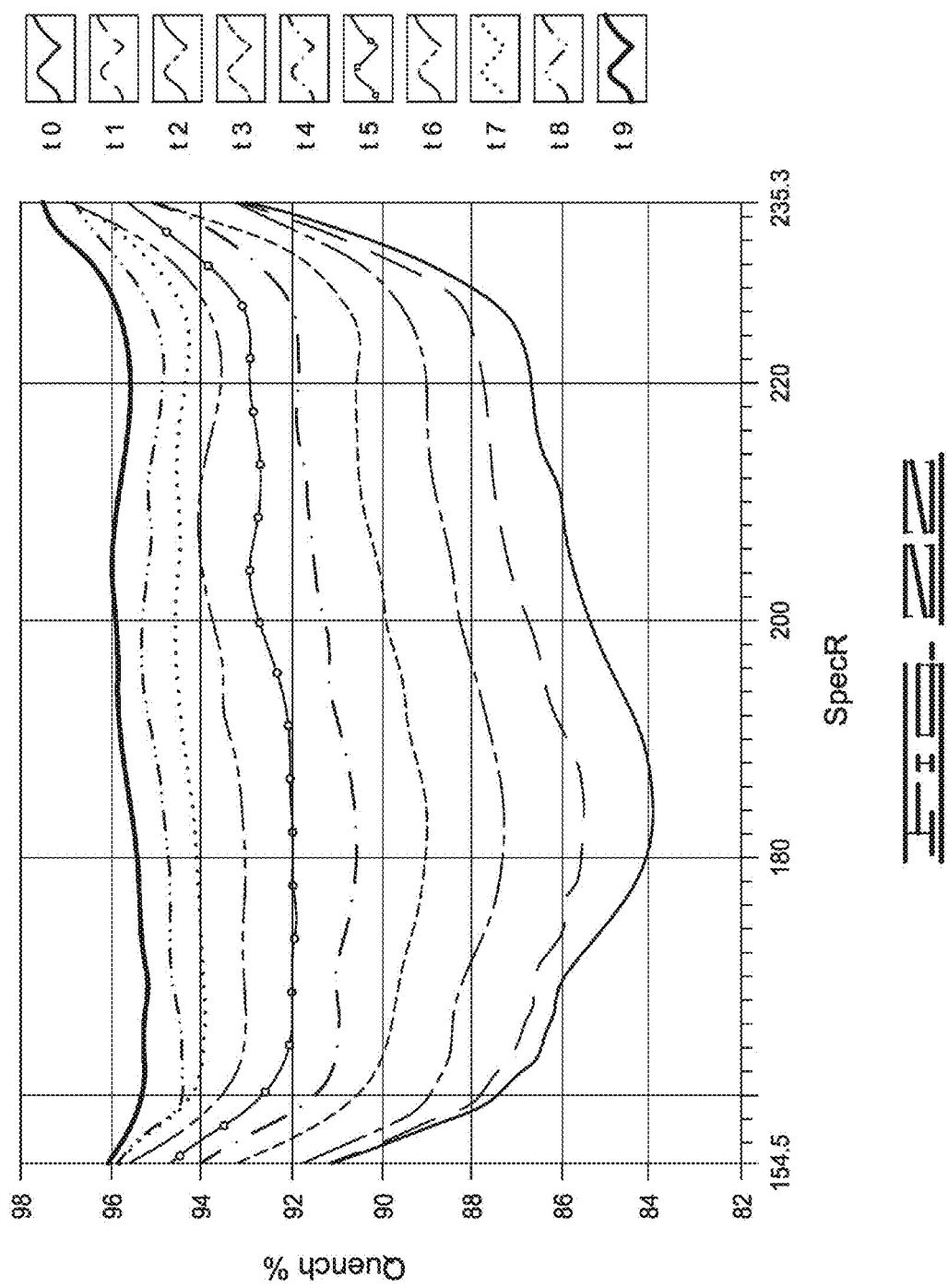
FIG. 22 illustrates examples of the stacked plots of multiple static spectral signatures for a first stage of a sensing event, in accordance with an embodiment of the disclosure.
Figure 23A:
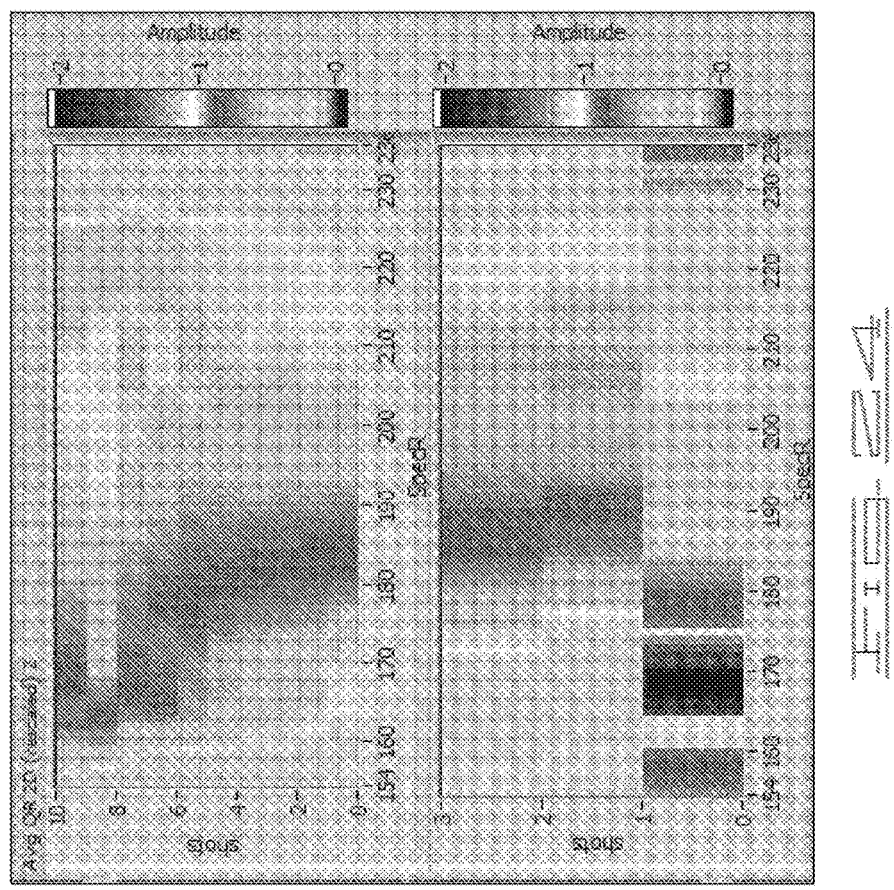
FIG. 23 illustrates examples of the stacked plots of multiple static spectral signatures for the second stage of a sensing event, in accordance with an embodiment of the disclosure.

FIGS. 22 and 23 illustrate examples of the stacked plots of multiple static spectral signatures. The stacked signatures from the first and second stages of FIG. 21 are plotted in FIGS. 22 and 23, respectively. FIG. 22 illustrates the three signatures acquired in the first stage in FIG. 21 and illustrates deeper quenching with the progression of time. FIG. 23 illustrates the ten traces of the second stage, which show the recovering process with less quenching with the progression of time.

While the stacked plots of FIGS. 22 and 23 show all the information in one plot, the details of each static spectral signature are covered up by the large dynamic range of the absolute quench level so that the major dip locations at early or later time with shallow absolute depth are difficult to be appreciated. In order to address this issue, each spectral signature can be normalized by its own distribution and linearly transformed so that the maximum quench ratio is set to zero, the baseline value to unity, and flare response to have a greater-than-one value. Then such transformed data was aggregated to generate a temporal-spectral intensity map, shown as a 2D false color map in FIGS. 24 and 25 and termed "temporal-spectral map". Such 2D temporal-spectral map can be used to easily track the variation of the intensity dip location in the time history.

FIG. 24 illustrates a temporal-spectral map for the explosive trinitrotoluene (TNT) and FIG. 25 illustrates a temporal-spectral map for the explosive Nitro-toluene (NT). As illustrated, the color designation of the temporal-spectral map was to highlight the deepest intensity dip location with red color and any flare event with white to black color depending on the strength. Accordingly, FIG. 24 shows that there was a flare event right at the beginning of the sensing event for a brief moment, which was not identified in previous sensing data utilizing prior intensity-based systems. Such flare only occurred at SpecR=170 region and the intensities at other wavelengths were still reduced, and hence it would be hidden by the dominating quench response in the prior intensity-based systems. Note that the x-axis is labeled SpecR instead of wavelength because the system is not calibrated to give actual wavelength.

Also as can be seen by FIG. 24, the maximum quenching ratio for a TNT analyte is initially established at SpecR=190. However, as more analyte molecules interacted with the sensing material and partially accumulated, the maximum quenching point is shifted to a shorter (bluer) wavelength. At the ending of sensing event, the maximum quenching occurs at a wavelength region where SpecR=160~180. It has been found that such "shifting of quenching dip" behavior is unique and reproducible to TNT samples. Accordingly, it provides critical information to robustly distinguish a TNT temporal-spectral map from a NT temporal-spectral map; thus, illustrating that the inventive optical detection device and method is suitable for the detection and identification of analytes.

VI. Test Results

A test to assess the impact of temperature of the analyte transport fluid on the intensity of the reaction of the analyte and reporter was conducted using the first preferred embodiment. A TNT vapor generator (Vgen by FUR), based on the acoustic means to dispel a fixed amount of a sample, was used as the analyte for the analyte transport fluid. The Vgen sample was in vapor form and roughly in the low picogram range. The analyte transport fluid was pre-heated to a temperature between 90 degrees Celsius and 120 degrees Celsius prior to entering capillary 28. The temperature of the analyte transport fluid at sensing slide 16 was about 40 degrees Celsius due to cooling loss in capillary 28. The flow rate of the analyte transport fluid was set to about 30 milliliters per minute. C-ring 36 was made of Teflon® and about 50-75 nanometers thick. Sensing slide 16 was coated with AFP material as the reporter. The results of the test are shown in FIGS. 13-17.

The sensorgram, which is the time history of the acquired fluorescence signal, is plotted in FIG. 13. The results acquired with several different temperature settings of the air-sampling nozzle are compared. In FIG. 13, first trace 68 has a temperature of 97 degrees Celsius, second trace 70 has a temperature of 103 degree Celsius, and third trace 72 has a temperature of 109 degrees Celsius. Baseline trace 74 is shown and had a temperature of 90 degrees Celsius. The full width at half minimum (FWHM) were about 9.6 seconds for first trace 68, 4.6 seconds for second trace 70, and 3.6 seconds for third trace 72 compared to 5.0 seconds for baseline trace 74. A 109 degrees Celsius setting is about 30% sharper, and the SNR of the data is about six (6) times better than the baseline data.

Additionally, the data of the test suggests that reducing the size of reporter 48 will increase performance. As shown in FIG. 13, when using AFP as reporter 48, an excessively large area of reporter 48, AFP in this test, not only reduced the SNR of the sensorgram, but also produced a very slow baseline return. The smallest AFP deposition used in our test was 20 nanoliters. The results for the 20 nanoliter sample show that the FWHM of the quenching curve was about 2.2 seconds, which is more than two times faster than the baseline response. The results are shown on FIG. 13 as trace 75.

A key point of using this invention is to capture a larger number of photons from the emitted wavelengths for improved signal to noise ratio. A first test used a band-pass (BP) optical filter in the first embodiment. However, emissions from the AFP through the first embodiment extended into wavelengths greater than 500 nm. A long-pass (LP) filter allows the harvesting of more photons. Using a LP filter, the total SNR is improved with a greater signal and only slightly elevated noise. The improvement by using the LP filter confirms that the SNR advantage of using this invention comes from the higher photon collection efficiency.

Figure 14:
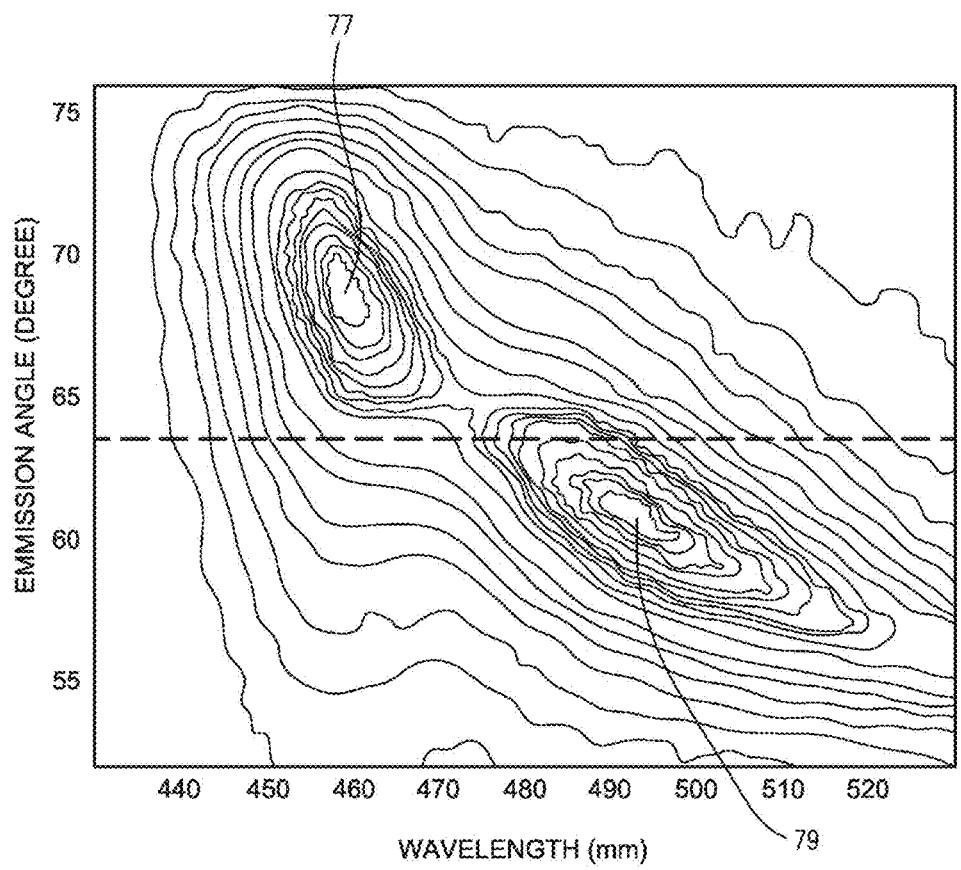
FIG. 14 depicts the fluorescence test results of the resulting wavelength from a reaction versus the angle of the emission for given temperature of the analyte showing the angular and spectral distribution of the AFP emission, in accordance with an embodiment of the disclosure.

Testing for target discrimination using spectral analysis shows the SPCE approach is improved over standard testing. The SPCE is a highly dispersive phenomenon, which means that the emissions from different reporters at different wavelengths will be distributed at different emission angles. Therefore, SPCE emission data contains a significant amount of spectral and spatial information. FIG. 14 shows a typical AFP SPCE map with a 30 nanometer SiO2 layer between an AFP and metal layer. This map shows the angular and spectral distribution of the AFP emission. In the spectral (horizontal) axis, the two major emission peaks located at 460 and 490 nanometers can be easily identified, peak 77 and 79 respectively. The AFP SPCE has significant spectral content beyond 500 nanometers, which was not observed in non-SPCE testing. On the emission angle (vertical) axis, the 460 nanometers fluorescence peaks at about 68 degrees, and 490 nanometers at 60 degrees. With a thinner SiO2 layer, the dispersion (angular separation of different emission peaks) would be smaller.

Figure 15:
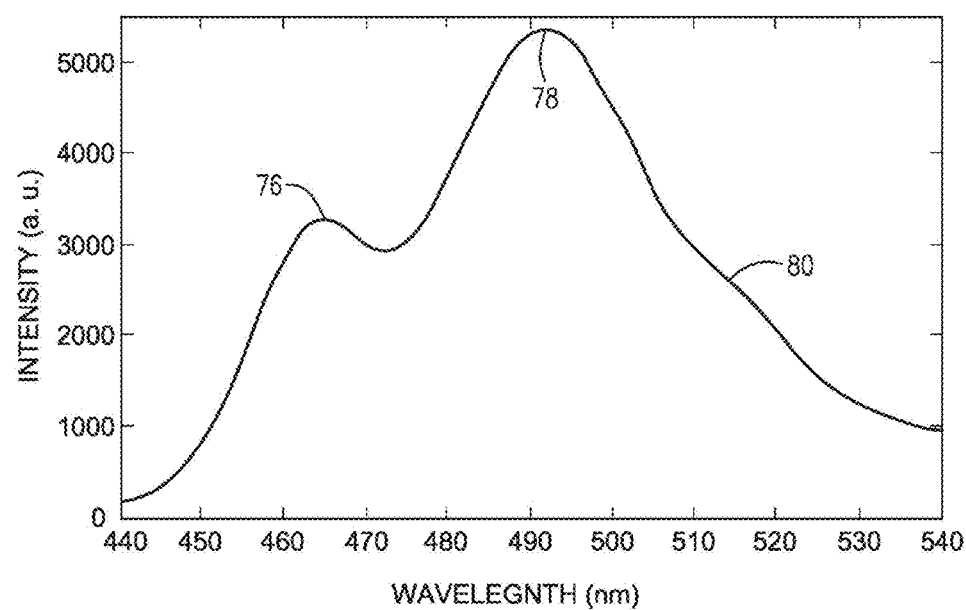
FIG. 15 depicts the spectrum of the fluorescence test results taken at an angle of about 64 degrees, in accordance with an embodiment of the disclosure.

Testing for the different quenching ratios of different explosive related analytes was also accomplished at different wavelengths. Three separate monitored emission band wavelengths are depicted in FIG. 15. First monitored emission band 76 was 465 nanometers. Second monitored emission band 78 was 495 nanometers. Third monitored emission band 80 was 515 nanometers. The tool to monitor these emission bands was the SPCE system above in conjunction with a fiber optic spectrometer. The time history plots of AFP/SPCE fluorescence signals observed at about 64 degrees emission angle at three different wavelengths are shown in FIGS. 16 and 17. The SNR of these curves were low compared to FIG. 13 because a fiber-based spectrometer was used for data collection, which can only collect very small portions of SPCE into the spectrometer.

For dinitrotoluene (DNT) tests shown in FIG. 16, both emission band 76 at 465 nanometers and emission band 78 at 495 nanometers have a similar quench ratio and emission band 80 at 515 nanometers has less quenching after the DNT vapor being introduced at about the $75^{th}$ second. However, both emission band 78 and emission band 80 in FIG. 17 have similar response for nitroglycerin (NG), and emission band 76 was observed to have less quenching after the NG vapor reached the sensing surface at about the $40^{th}$ second. This trend is reproducible, thereby providing explosive identification data.

It is also known that sample temperature will change the fluorescence intensity. Similar temperature induced fluorescence signal changes can be observed in both FIGS. 16 and 17. For a slow rising temperature before the $70^{th}$ second, emission band 76 at 465 nanometers showed slowly increasing intensity, emission band 80 at 515 nanometers had a reduced intensity, and emission band 78 at 495 nanometers had a similar response to emission band 80. The intensity responses were reversed to the quickly dropping temperature. Such temperature effect can be well observed after about the $120^{th}$ second when the gas chromatograph (GC) oven rapidly reduced its temperature at the end of the GC run. The temperature effect has much larger amplitude due to larger temperature changes. This time, a much large, but opposite effect on emission band 76 and emission band 80 can be seen. Emission band 78 again has the same rising response to emission band 80, but has less temperature sensitivity.

Computer modeling shows that multiple target discrimination using a plurality of reporters 48 in an array is easily achievable with the inventive embodiments. An array of reporters 48, such as AFP, deposited on sensing slide 16 can be less than about 1 millimeter in diameter with manual deposition. With a mechanized deposition, each reporter 48 will be as small as several hundred microns in diameter, and the total array will be less than about 1×1 millimeter squared, as shown in FIG. 4A. Multiple reporters 48 such as AFP, phenyl quinoline, or other similar class of material, can be deposit in a tight array format within the common sample flow path to detect various explosives simultaneously. By selecting reporters 48 with different emission wavelengths, this invention can separate the emission from reporters 48 spectrally and spatially, and detect them individually with an array detector 24. Reporter 48 emissions will maintain their spatial and spectral information while propagating through device 10 to be collected by a 2D CCD array detector 24. The spectral information can then be collected and differentiated by the 2D CCD array detector 24 for target discrimination and simultaneous detections.

Other embodiments of the current invention will be apparent to those skilled in the art from a consideration of this specification or practice of the invention disclosed herein. Thus, the foregoing specification is considered merely exemplary of the current invention with the true scope thereof being defined by the claims.

In fluorescence interrogation methods utilizing the SPCE-based techniques described above, some spatial domain information is effectively exchanged for additional spectral domain information in order to increase an overall signal to noise ratio and/or other performance measures of the detector. In particular, with respect to relatively inexpensive hand held detectors, SPCE-based techniques often lack enough spatial information to distinguish emissions from different reporters placed on the same sensing slide. For example, in some relatively compact SPCE-based embodiments, fluorescence spectra from multiple reporters on the same sensing slide may be superimposed onto one another. While emission peaks from different reporters can be programmatically segregated from one another, since they are typically located at different wavelengths, the signal to noise ratio of the individual signatures in the summed or superimposed spectral profile can degrade as the number of different reporters (e.g., also referred to as "spatial channels" or "reporter channels") of the system is increased.

Embodiments of the present disclosure provide systems and methods using the spectral features described in relation to various SPCE-related techniques while retaining enough spatial information and/or resolution to spatially segregate optical signals provided by multiple different reporter channels disposed on a single sensing slide. To provide for simultaneous analysis of spectral and spatial features produced by a reporter array, embodiments replace selected SPCE-based detector elements, as described herein, with various elements of hyperspectral imaging techniques. Such hyperspectral imaging techniques employ a detection platform configured to acquire optical spectral, temporal, and spatial information using a hyperspectral detection module implemented using (1) a dielectric wedge interferometer structure, (2) a coded aperture spectrometer structure, and/or (3) a one dimensional (1D) stepped Fabry-Perot interferometer structure.

In various embodiments, such hyperspectral detection modules may be configured to image the spectrums of multiple different reporters at substantially the same time with a non-scanning (i.e. snapshot) imaging device, thereby providing detection systems that can detect and identify multiple chemicals and explosives simultaneously. For example, a hyperspectral detector module may be configured to acquire the spectral responses of multiple spatially separated reporters without cross-channel interference among reporters. Hence, complete and clean information from all reporters may be acquired in order to provide a maximum system detection sensitivity and identification capability.

Figure 26:
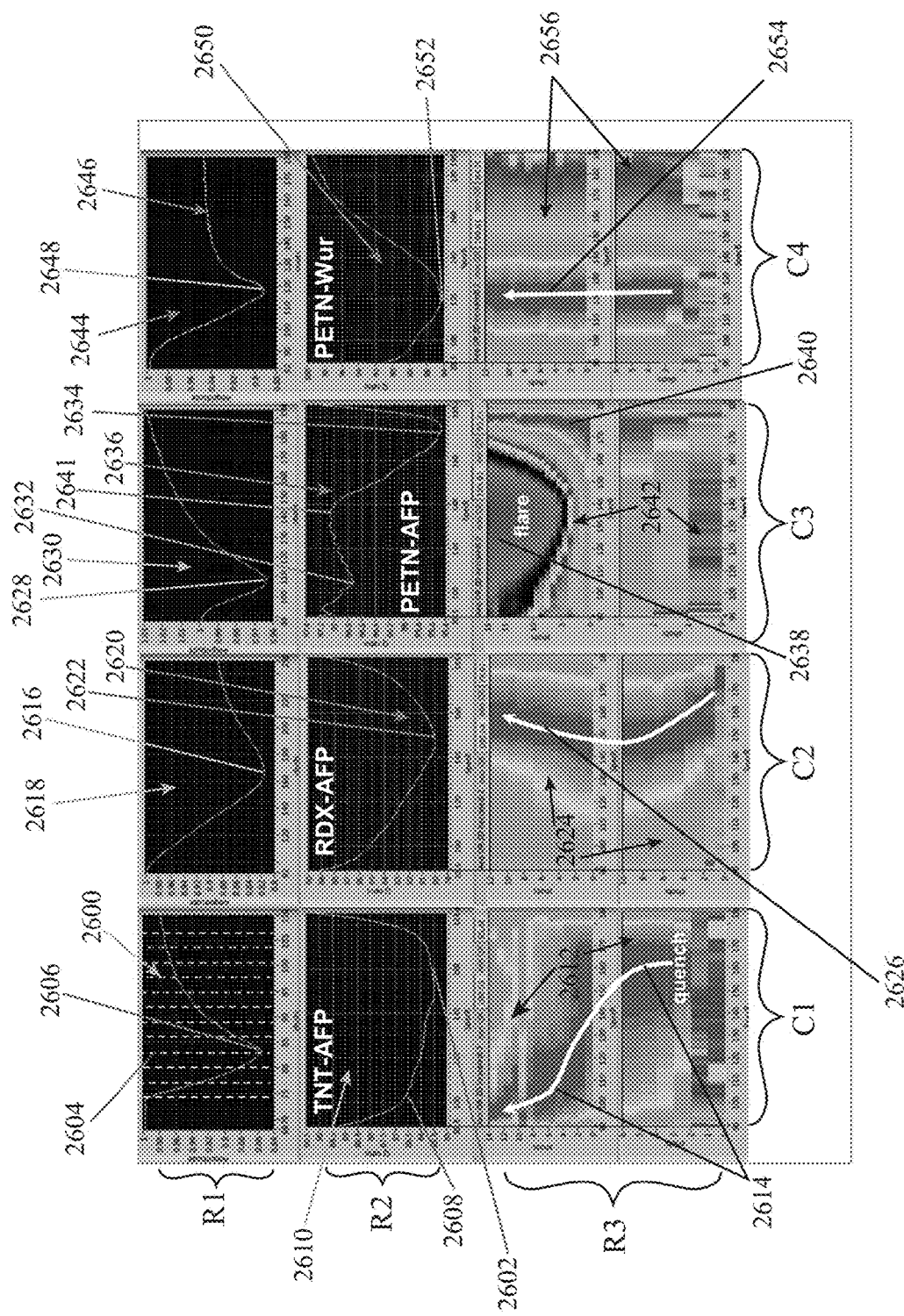
FIG. 26 illustrates detection data provided by an optical collection and detection device, in accordance with an embodiment of the disclosure.

FIG. 26 shows experimental detection data (i.e., intensity-time sensorgrams—row R1, static spectral signatures—row R2, and temporal spectral signatures—row R3) collected for several explosives using an AFP reporter (AFP, columns C1, C2, C3) or Wurster material (Wur, column C4). FIG. 26 is provided to illustrate at least some of the various benefits of using an intensity-time sensorgram, a static spectral signature, and/or a temporal spectral signature to identify a particular chemical or explosive. A temporal spectral signature may also be referred to as a temporal-spectral intensity map or a temporal-spectral map, as discussed with respect to FIGS. 24 and 25, for example, and may also be understood to refer to a specific trend, pattern, or feature within a temporal-spectral intensity map or a temporal-spectral map, such as a temporal spectral signature that may be used to identify a particular analyte. In some embodiments, a temporal spectral signature may be a stacked plot of multiple static spectral signatures, as discussed with respect to FIGS. 22 and 23.

Row R1 includes intensity-time sensorgrams 2600, 2618, 2630, and 2644 corresponding to columns C1-C4. For each sensorgram, after a substantially flat intensity baseline was established (e.g., normalized to "one" on the vertical scale), explosive vapors of trinitrotoluene (TNT, shown in column C1), cyclotrimethylenetrinitramine (RDX, shown in column C2), and pentaerythritol tetranitrate (PETN, shown in columns C3 and C4) were introduced to their respective reporters (e.g., AFP and/or Wur, as indicated). As shown in the embodiment presented by FIG. 26, each reporter provided a quench event (e.g., a reduction in intensity) in response to the introduction of a vapor. Each quench event can be characterized by various parameters, such as a time to reach a deepest quench or minimum intensity, the recovery slope from the deepest quench/minim intensity towards or to the baseline, and/or other parameters. For example, the TNT quench event may be characterized by the time and/or spectral value of minimum 2606. Similarly, the RDX intensity-time sensorgram 2618 shows a quench event that may be characterized by the time and/or spectral value of minimum 2616, and PETN intensity-time sensorgrams 2630 and 2644 shows quench events that may be characterized by the time and/or spectral values of minimums 2628 and 2648, respectively. In various embodiments, such quench characteristics (e.g., the time required to reach the deepest quench relative to the baseline, and/or the recovery slope to the baseline, and/or other quench characteristics) may be used to identify a type of chemical or explosive and/or the presence of the chemical or explosive. Other characteristics, such as those related to flares or increases in intensity (e.g., a maximum intensity, a time to maximum intensity, a recovery time and/or slope towards baseline), may also be used to identify a presence and/or type of chemical or explosive.

However, intensity-time sensorgrams are typically sensitive to the sample presentation process and may change substantially depending on the stability of the device and/or environment, the exposure duration, and the available amount of analyte. As a result, it can be difficult to provide dependable and accurate explosive recognition relying solely on intensity-time sensorgrams and the more common variations in the patterns they present.

By contrast, the spectral change (e.g., the spectral profile of the intensity change) in each reporter's emitted spectrum, presented as static spectral signatures 2610, 2620, 2636, and 2650 in row R2, can include relatively reliable information with which to identify each explosive species. In various embodiments, each static spectral signature 2610, 2620, 2636, and 2650 may correspond to a static spectral quenching ratio, which may be determined by comparing, for each reporter and detection sequence, the emission spectrum at the deepest quench to the emission spectrum of the reporter's baseline.

For example, TNT-AFP static spectral signature 2610 includes a broad deepest quench 2602 at a relatively long wavelength (e.g., indicated by a relative spectral index approximately SpecR=160), and a minor intermediate quench or dip 2608 at a relatively short wavelength (approximately SpecR=100). RDX-AFP static spectral signature 2620 includes a relatively sharp deepest quench 2622 at approximately SpecR=150, PETN-AFP static spectral signature 2636 includes a relatively shallow local quench 2632 at a short wavelength (e.g., SpecR=105) and a relatively sharp and deep deepest quench 2634 at SpecR=175, and PETN-Wur static spectral signature 2650, which shows a different signature than PETN-AFP, includes a deepest quench 2652 at SpecR=120. Unlike intensity-time sensorgrams, static spectral signatures may be relatively consistent and reliable regardless of variations in the sample introduction process.

While RDX-AFP intensity-time sensorgram 2618 may exhibit a shape and deepest quench location similar to that of TNT-AFP static spectral signature 2610, corresponding dynamic temporal spectral signatures, shown in row R3, provide additional information to further assist in differentiation and/or identification. As shown in FIG. 26, the temporal spectral signatures in row R3 are plotted as 2D false color maps, where each top map and bottom map in each column form a connected and continuous map for that column; the separation is used to help indicate the timing of deepest quench. One possible procedure to obtain the dynamic temporal spectral signatures is as follows.

First, multiple spectra of a detection operation are acquired. For example, vertical dashed lines 2604 in TNT intensity-time sensorgram 2600 indicate the times when multiple spectra of the presented detection operation are acquired. Each acquired spectrum is compared to a corresponding baseline spectrum, and the ratios are then plotted as 2D temporal spectral signatures (e.g., temporal spectral signatures 2612, 2624, 2642, and 2656). In the embodiment shown in FIG. 26, each temporal spectral signature 2612, 2624, 2642, and 2656 begins at the bottom of its lower map (e.g., at zero time) and ends at the top of the upper map (e.g., after a period of time has passed). Each temporal spectral signature is split into its upper and lower map at the time of deepest quench, and the cross section cut of the 2D data at the split corresponds to the static spectral signature shown in row R2.

In various embodiments, a false color scheme may be used to indicate the ratio magnitude, as shown in row R3. In row R3, the red shades indicate quenches, and the darkest reds at a particular time indicate the deepest quench at that time, and the deepest quenches over a period of time can be strung together to form temporal quench signatures, shown in row R3 as temporal quench signatures 2614, 2624, 2640, and 2654 (e.g., major dip locations along the temporal data set including the absolute quench level, all referenced by spectral content). The black to brown shades indicate a flare (e.g., intensity increase) such as, for example, flare 2638 of temporal spectral signature 2642. These and other characteristics can be used to identify/determine a particular chemical and/or explosive and/or a presence of the chemical and/or explosive.

In particular, the TNT temporal quench signature 2614 is shown to shift from a longer wavelength (SpecR=160) to a shorter wavelength (SpecR=100), which is a unique feature to recognize TNT. By contrast, RDX temporal quench signature 2626 starts out similar to TNT temporal quench signature 2614 but bends toward longer wavelengths after reaching its deepest quench. In another example, PETN-AFP temporal quench signature 2640 shows an initial quench at a relatively long wavelength (SpecR=175), corresponding to deepest quench 2634 of static spectral signature 2636, but then reveals a delayed broad flare 2638 (e.g., after the deepest quench), which corresponds to peak 2641 of static spectral signature 2636. By contrast, PETN-Wur temporal spectral signature 2656 includes no flare and shows a relatively broad temporal quench signature 2654, which corresponds to deepest quench 2652 of static spectral signature 2650, at a relatively continuous and short wavelength (SpecR=120).

Column C4 helps illustrate a benefit to using spectral signatures. In the PETN-Wur data set in column C4, the deepest quench 2648 in intensity-time sensorgram 2644 corresponds to a reduction of only approximately 11% in intensity from baseline. By contrast, the spectral signatures show a deeper quench of approximately 16% from baseline (shown as 84% as "min QR" in static spectral signature 2650). The lower (and potentially more difficult to identify) value in intensity-time sensorgram 2644 is the result of how the sensorgrams are formed, which is by averaging all spectral responses across the time of the detection process. Thus, in embodiments utilizing sensorgrams, quenching or flare or other spectral signature features that occur over relatively short time periods and/or over relatively narrow wavelengths can be significantly blurred or averaged out of the presented data, which can make it more difficult to detect, identify, and/or differentiate chemicals and/or explosives.

The aforementioned examples help demonstrate that temporal spectral signatures provide relatively consistent detection information and may be used to identify a variety of explosives reliably. For example, a database of temporal spectral signatures cross referenced to known analytes and reporters may be generated (e.g., using a controlled calibration process similar to the processes described herein to determine and/or detect presence and/or type of analyte), and newly acquired temporal spectral signatures may be compared to that database to determine a presence and/or type of a known analyte from the temporal spectral signatures, or to infer presence of an unknown analyte (e.g., through chemical similarity). Furthermore, the multiple distinguishable temporal spectral signatures, corresponding to the multiple different explosives and/or analytes, further show that desirable detection information may be obtained when using multiple reporter channels interrogated individually. In addition, as shown in column C4, overall sensitivity may be improved, and detection limits enhanced, by interrogating spectral signatures and accurately identifying spectral features at various wavelengths rather than relying on intensity-time sensorgrams alone.

Several different types of hyperspectral imaging techniques are presented herein configured to take advantage of the benefit of spectral interrogation of light emitting reporters with sufficient spatial separation that emissions from different reporters disposed on the same sensing slide and/or used within a handheld detector system may be interrogated at substantially the same time in order to improve overall performance of chemical, biological, and/or explosive material detection.

Figure 27:
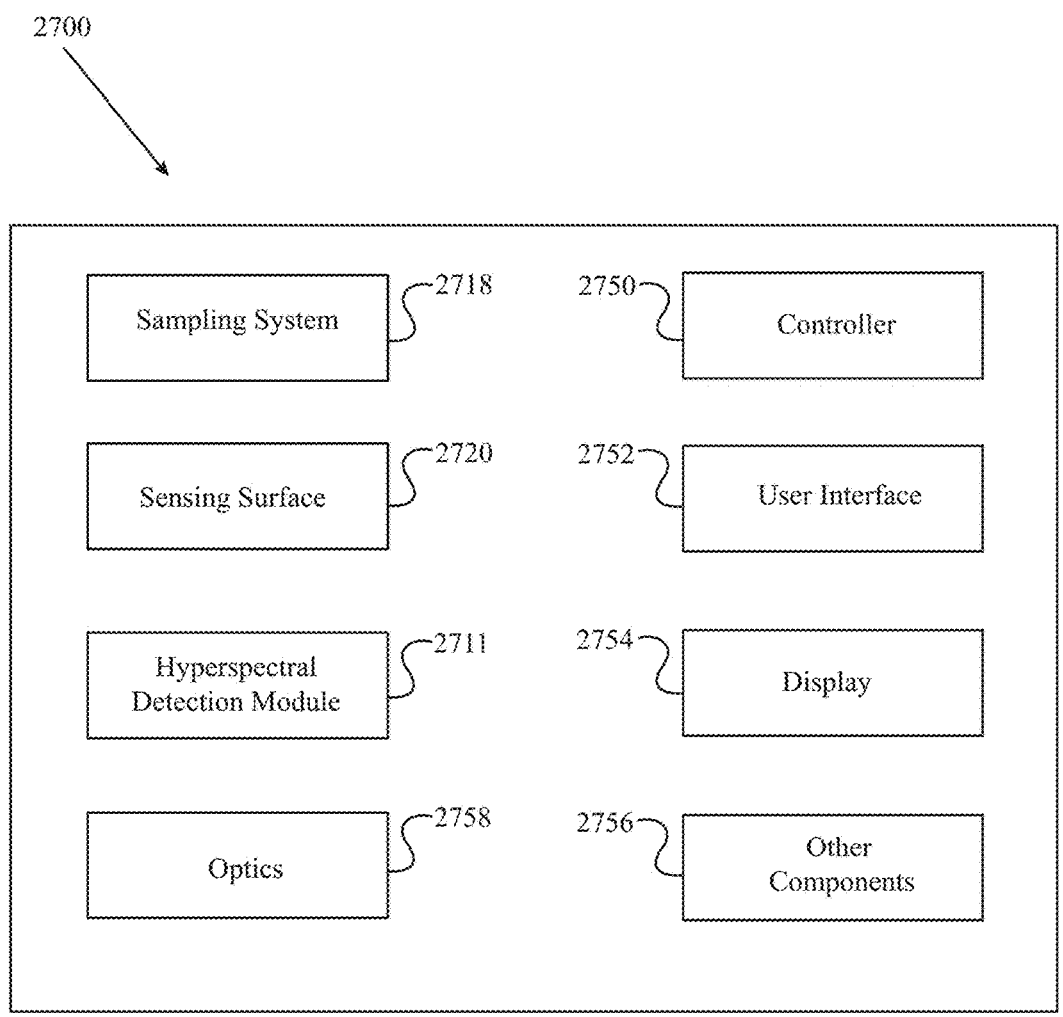
FIG. 27 illustrates a block diagram of an optical collection and detection device, in accordance with an embodiment of the disclosure.

FIG. 27 illustrates a block diagram of optical collection and detection device 2700 in accordance with an embodiment of the disclosure. Optical collection and detection device 2700 may include one or more of the following components: a sampling system 2718 (e.g., an air sampling system), a sensing surface 2720, a hyperspectral detection module 2711, and a controller 2750, which may be implemented as a data acquisition (DAQ) and/or signal processing (SP) system. Detection device 2700 may also include optics 2758, a user interface 2752, a display 2754, and/or other components 2756 (e.g., such as a camera implemented with a charge coupled device (CCD) and/or more generally a focal plane array (FPA) image capture device).

Sampling system 2718 (e.g., an air sampling system) may include an input segment, various air-sampling configurations, a heating source, a capillary, a flow cell, and/or other elements as previously discussed herein with respect to input segment 14 of FIGS. 1A-5, for example. More generally, sampling system 2718 may be implemented with any arrangement of tubing, fan, and/or air pump configured to suction an analyte transport fluid from the environment and deliver it to sensing surface 2720.

Sensing surface/sensing slide/side 2720 may be implemented with a transparent substrate (e.g., a quartz or glass substrate) that may be coated with a plurality of substrate layers and/or reporters. In some embodiments, sensing surface 2720 may be implemented according to an SPCE sensing slide or portion of an SPCE sensing slide, as described herein. In other embodiments, sensing surface 2720 may be implemented as any optically substantially transparent substrate, including glass, quartz, various films, and/or other surfaces configured to support one or more reporters 2706 and transmit light generated by the reporters to hyperspectral detector module 2711. For example, reporters 2706 may be placed on one surface of sensing surface 2720 accessible to analyte flow 2710, and the opposing surface of sensing surface 2720 may be sealed against reporters 2706 and/or analyte flow 2710 to protect elements of hyperspectral detector module 2711 from exposure to analytes 2704 and/or reporter 2706. In some embodiments, sensing surface 2720 may be configured to allow easy replacement of sensing surface 2720 with a new sensing surface, such as when reporters 2706 are too stale to react with analytes 2704. One or more reporters may be applied in arrays (e.g., in strips or patches, as shown in relation to sensing surface 2720 of FIG. 32). When implemented with multiple types of reporters, different reporters may react to different analytes carried in the analyte transport fluid. The array may be a single array having a total area of approximately 25 mm$^2$ or 10 mm$^2$ to approximately 1 mm$^2$ or smaller. As used herein, reporter "patches" may be implemented as rectangles, squares, disks, dots, and/or any other shape or combination of shapes of reporter material applied to sensing surface 2720. In general, the size of each individual reporter patch may vary from 0.1 mm to 1 mm or 2 mm, for example, and may preferably be approximately 1 mm in diameter. The size of each individual reporter strip may vary in width similarly to the range of diameters for reporter patches, and may be 10 or 20 mm in length or longer, up to the effective field of view of hyperspectral detection module 2711 and/or optics 2758, for example.

In one or more embodiments, various different types of reporters may applied to and/or used with sensing surface 2720, including any of the reporters described herein, (e.g., fluorescing, turn-on, quenching, AFP and/or CWIC). For example, various chemiluminescent, colorimetric (e.g., absorptive), and/or other fluorescing, non-fluorescing, light emitting, and/or light absorbing materials and/or combinations of materials may be used to form reporters 2706, such as various polyarylenes, polyquinolines (PQ), peroxide reactive materials (e.g., various oxamides and/or other materials, which may or may not be used in conjunction with various light emitting/amplification materials such as various iptycenes), pH sensitive materials (e.g., for detecting oxidizing salts), redox indicator dyes, diphenyl anthacene (DAP), perylene, and/or mixtures thereof. More generally, sensing surface 2720 may be implemented with any reporter or selection of reporters configured to react with one or more analytes or types of analytes and produce an electromagnetic response that can be detected by hyperspectral detection module 2711, as described herein.

Optics 2758 of device 2700 may include one or more of a lens, a lens assembly, a reflector, a fiber optic taper and/or assembly, a dispersive component, a grating, a grid, an excitation assembly configured to provide excitation of reporters on sensing surface 2720 (e.g., excitation assembly 2708 in FIG. 28A including an LED light source that is configured to illuminate sensing surface 2720 and reporters 2706), a spectral filter, a spatial filter, and/or other elements of an optical segment and/or imaging optics, as described herein. In some embodiments, optics 2758 may be partially and/or fully integrated with hyperspectral detection module 2711. In various embodiments, one or more elements of optics 2758 may be in optical communication with sensing surface 2720 and/or an emission detection sensor (e.g., of hyperspectral detection module 2711), such as a photodetector, a CCD array, a focal plane array (FPA), and/or other type of detector.

Controller 2750 may be implemented as any appropriate processing device or devices (e.g., a logic device, microcontroller, processor, application specific integrated circuit (ASIC), data acquisition device, or other computing device) that may be configured to execute appropriate instructions, such as software instructions to implement any of the methods described herein. For example, controller 2750 may be configured to receive image data from a detector of hyperspectral detection module 2711 and process the image data to determine a temporal spectral signature of an air sample provided by sampling system 2718. In various embodiments, one or more elements of controller 2750 may be integrated with hyperspectral detection module 2711 and/or other elements of device 2700, may be disposed within device 2700, and/or be disposed external to device 2700 and configured to communicate with elements of device 2700 through a wired and/or wireless interface (e.g., other components 2756).

Display 2754 may be implemented with a color or monochrome LCD, LED, OLED, and/or other type of pixel based display configured to display acquired and/or processed spectral images (e.g., intensity-time sensorgrams, static spectral signatures, temporal spectral signatures, temporal quench signatures) and/or other images, data, and/or information associated with operation of device 2700. For example, display 2754 may be implemented with a relatively compact and/or thin display to facilitate mobile and/or low power embodiments of device 2700. In some embodiments, display 2754 may be implemented as a touch screen display and form at least a portion of user interface 2752. In various embodiments, user interface 2752 may be additionally and/or alternatively implemented as one or more buttons, switches, rotary knobs, joysticks, sliders, touchpads, and/or other user interface elements. In other embodiments, display 2754 may be external and/or remote to device 2700 and configured to communication with one or more elements of device 2700 over a wired or wireless interface (e.g., other components 2756).

Other components 2756 may be implemented with one or more devices configured to facilitate operation of device 2700 as may be desired for various applications. For example, other components 2756 may include one or more power sources or batteries, wired or wireless data and/or signal interfaces, external memory interfaces (e.g., universal serial bus interfaces, card readers), infrared and/or visible light cameras, audible or visible alarms, charging and/or power regulation circuitry, a mechanism to adjust a position of and/or replace sensing surface 2720, a temperature sensor (e.g., configured to measure a temperature of an analyte transport fluid, a temperature of sensing surface 2720, a temperature associated with other elements of device 2700, and/or an ambient temperature associated with device 2700), one or more heaters (e.g., to form temperature gradients and/or provide temperature stability), and/or other devices configured to facilitate operation of device 2700 for one or more applications. In some embodiments, other components 2756 may include a machine readable medium configured to store non-transitory instructions for loading and/or execution by controller 2750.

Hyperspectral detection module 2711 may be implemented as one or more optical elements, assemblies, systems, and/or other devices configured to acquire spectral and/or spatial information from reporters disposed on sensing surface 2720 and to provide the spectral and/or spatial information to controller 2750 and/or display 2754. For example, in one embodiment, sensing surface 2720 of device 2700 may be implemented with an SPCE slide or a portion of an SPCE slide, as disclosed herein, and optics 2758 and/or hyperspectral detection module 2711 may be implemented with various emission assemblies, optical elements, filters, and/or detectors (e.g., photodetectors, a camera implemented with a charge coupled device (CCD), a focal plane array (FPA) image capture device, and/or other detectors) configured to acquire emission spectrums from reporters on the SPCE slide, as described in relation to FIGS. 1A-25. In other embodiments, sensing surface 2720 may be implemented simply with one or more substantially optically transparent substrates. FIGS. 28A-33 illustrate various embodiments of device 2700 implemented with different types of hyperspectral detection modules, including hyperspectral detection modules implemented using a dielectric wedge interferometer structure, a coded aperture structure, and/or a one dimensional (1D) stepped Fabry-Perot interferometer structure.

Figure 28A:
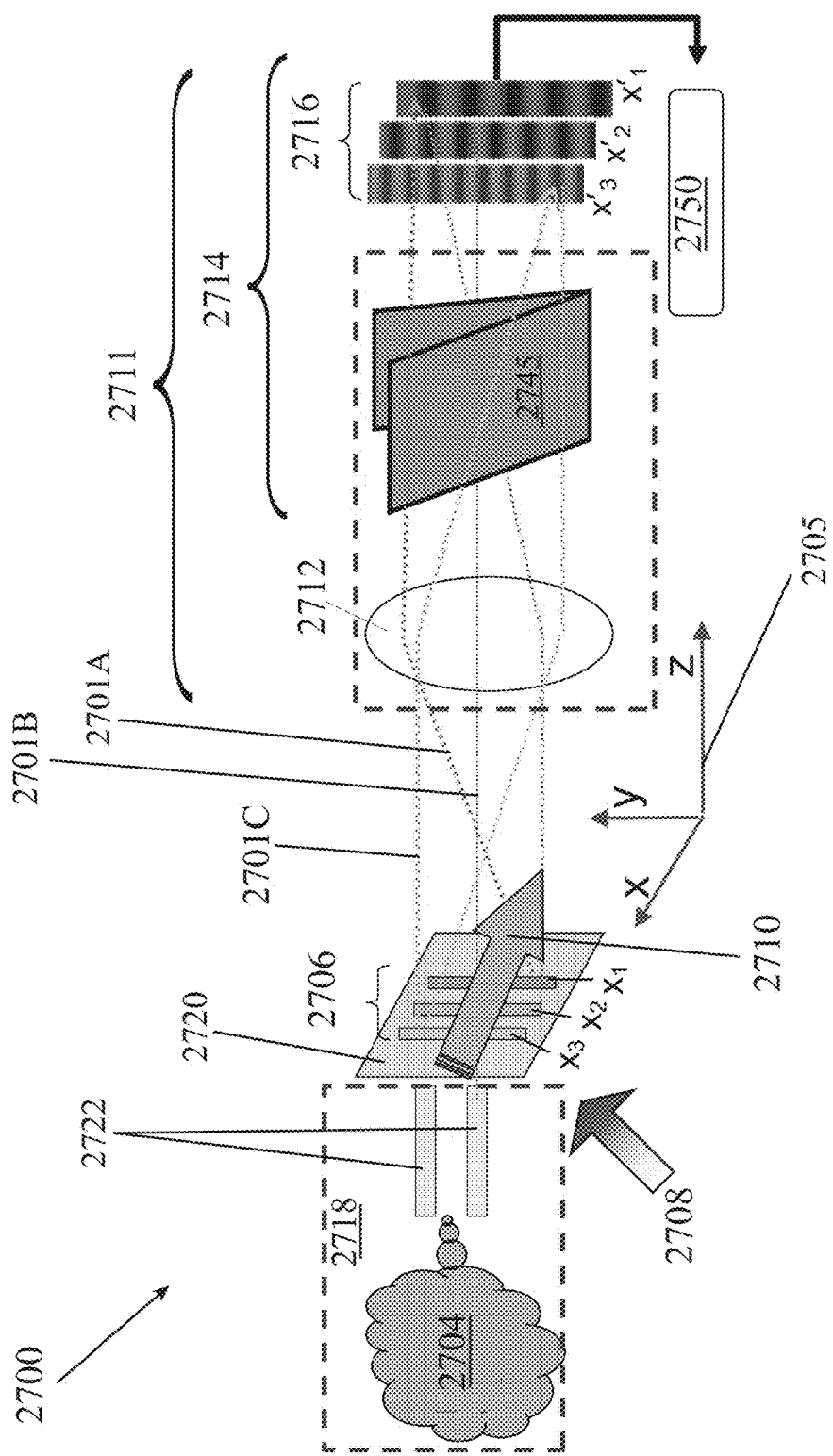
FIG. 28A illustrates an optical collection and detection device implemented with a hyperspectral detection module based on a dielectric wedge interferometer structure, in accordance with an embodiment of the disclosure.
Figure 32:
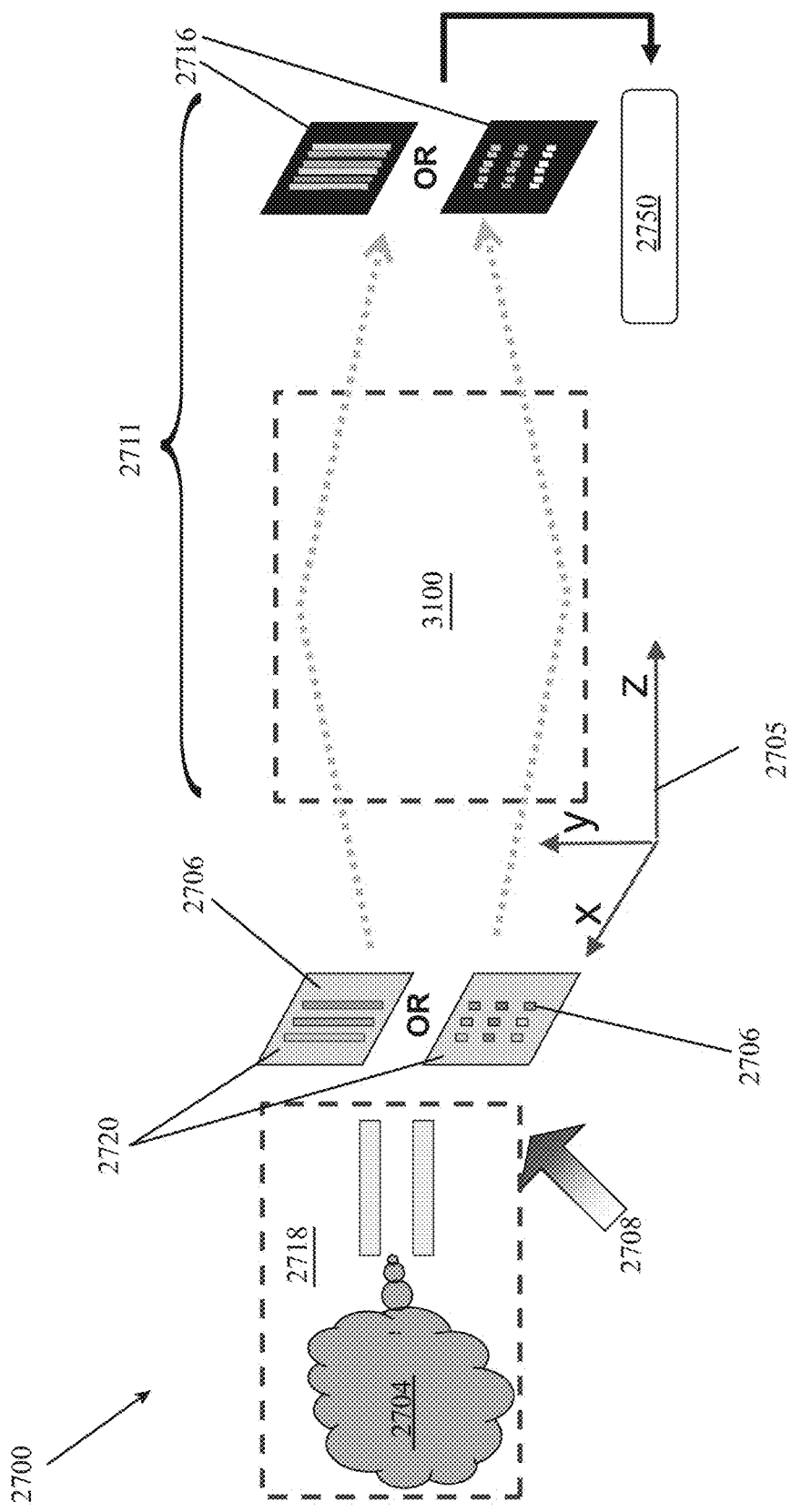
FIG. 32 illustrates an optical collection and detection device implemented with a hyperspectral detection module based on a coded aperture spectrometer structure, in accordance with an embodiment of the disclosure.

FIG. 28A illustrates optical detection device 2700 implemented with a hyperspectral detection module based on a dielectric wedge interferometer structure, in accordance with an embodiment of the disclosure. In FIG. 28A, flow channel(s) 2722 (e.g., heated flow channel(s)) provide analytes 2704 (e.g., explosive, chemical, or biological warfare substances) in the form of an air sample as analyte flow 2710 to reporters 2706 (e.g., emission sources such as AFP, CWIC, Wurster's Blue, other fluorescing or chemiluminescent emission sources, and/or other types of emission sources) on sensing surface 2720. In some embodiments, a temperature gradient may be provided in flow channel 2722 to encourage analytes 2704 in analyte flow 2710 to interact with reporters 2706. In various embodiments, depending on a spatial resolution and/or other characteristics of the hyperspectral detector module 2711, reporters 2706 may be provided in the form of reporter strips at locations x1, x2, x3, to form a reporter strip array as shown in FIG. 28A, for example, or in the form of one or more reporter patches to form reporter patch array 3102, as shown in FIG. 32, on sensing surface 2720. Analytes 2704 may correspond to an environment associated with an area of interest, such as an airport screening location, a shipping container receiving point, or other locations where reliable detection of analytes is desired.

As shown in FIG. 28A, device 2700 may include an excitation assembly 2708 positioned to illuminate reporters 2706 with a light wave having a first wavelength from the light source, which may also be referred to herein as an "input light". Additionally, "wavelength" is understood to refer to both the light wave and the associated wavelength of the light wave. In embodiments of device 2700 including excitation assembly 2708, the first wavelength may cause one or more of reporters 2706 to fluoresce and generate a second wavelength different from the first wavelength. When appropriate fluorescing ones of reporters 2706 react with analytes 2704, those reporters 2706 may generate a third wavelength (e.g., a reacting fluorescence, propagating along ray paths 2701A, 2701B, and/or 2701C through lens assembly 2712 and/or dielectric wedge interferometer structure 2745), which can be acquired by detector 2716 and used to detect presence of analyte 2704. As understood by one skilled in the art, more than one wavelength (e.g., a spectrum) may be emitted by the reporter in response to the first wavelength and before (e.g., second wavelength) and when reacting with the analyte (e.g., third wavelength). In some embodiments, one or more of reporters 2706 may each be configured to generate emission and/or absorption spectrums (e.g., spectral responses) in response to reacting with analytes 2704 without requiring excitation by excitation assembly 2708 and/or the first wavelength (e.g., one or more of reporters 2706 may be non-fluorescing, such as reporters formed from various chemiluminescent or colorimetric materials).

In the embodiment illustrated by FIG. 28A, device 2700 includes hyperspectral detector module 2711 including lens assembly 2712, dielectric wedge interferometer structure 2745, and detector 2716 configured to acquire spectral responses x1', x2', x3' of reporters 2706 and provide the spectral responses to controller 2750. Lens assembly 2712 may include one or more lenses, reflectors, and/or other optical elements configured to collect and concentrate the one or more spectral responses generated by reporters 2706 onto dielectric wedge interferometer structure 2745 and/or detector 2716. In some embodiments, some or all of lens assembly 2712 and/or dielectric wedge interferometer structure 2745 may be integrated with detector 2716 (e.g., coupled directly to a front face of detector 2716) in order to reduce an overall size of hyperspectral detector module 2711. In embodiments where dielectric wedge interferometer structure 2745 is integrated with detector 2716, the integrated structure 2714 may be smaller than the optical width of the spectral responses x1', x2', x3' of reporters 2706, and a scanning mechanism (e.g., other components 2756) may be included to scan integrated structure 2714 across spectral responses x1', x2', x3' in order to construct a hyperspectral image of all spectral responses x1', x2', x3'.

Figure 28B:
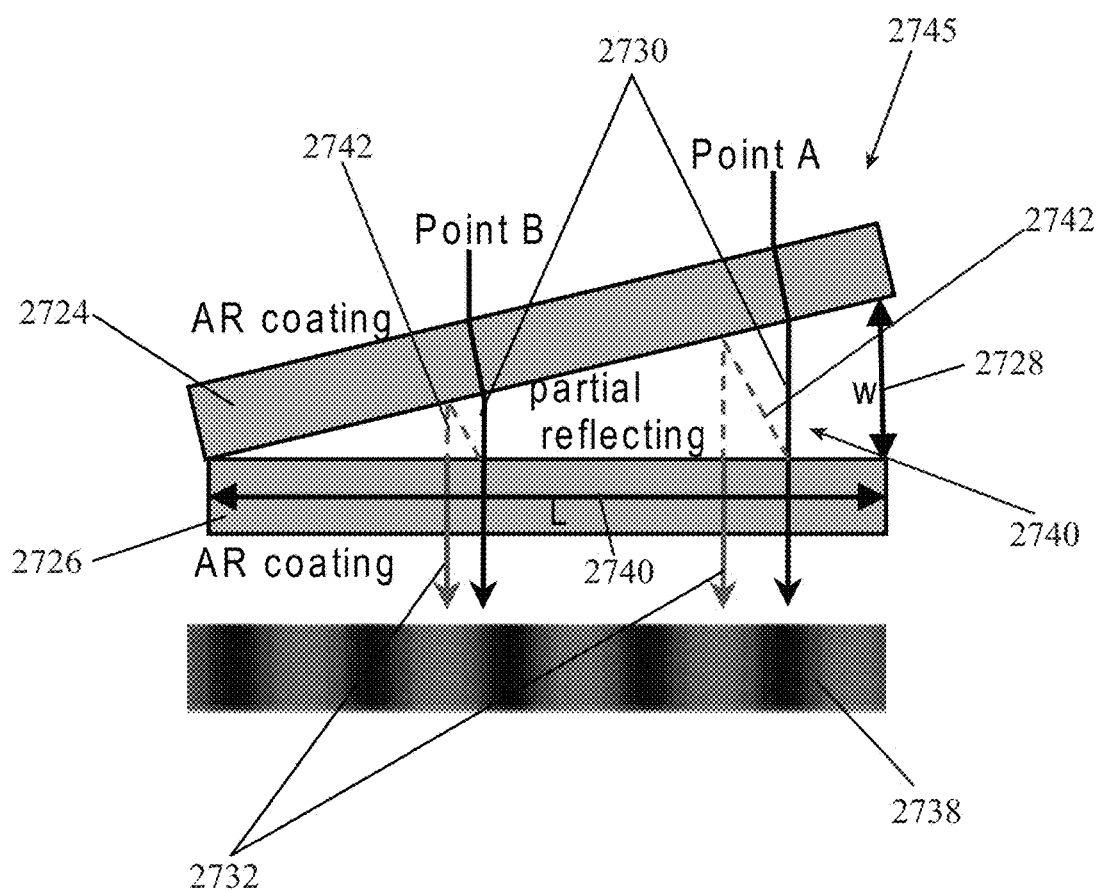
FIG. 28B illustrates a dielectric wedge interferometer structure and a corresponding interference pattern, in accordance with an embodiment of the disclosure.

FIG. 28B illustrates dielectric wedge interferometer structure 2745 and a corresponding interference pattern or interferogram, in accordance with an embodiment of the disclosure. Interference between two surfaces (e.g., of glass plates) such as those in a Fabry-Perot (FP) resonator may be used as a spectral analysis tool. For example, a low-finesse FP resonator with a variable cavity size may be used to generate an interferogram from incident light, and spectral information (e.g., emission and/or absorption spectrums) in the interferogram may be extracted by applying a Fourier Transform to the interferogram. Such FP resonators include dielectric wedge interferometer structures, such as dielectric wedge interferometer structure 2745 in FIGS. 28A-B.

As shown in detail in FIG. 28B, dielectric wedge interferometer structure 2745 includes a linearly varying gap 2740 (e.g., which may be filled with a dielectric material, such as air or index matching fluid or another substantially transparent dielectric material, or may be substantially a vacuum), which creates an interference pattern/interferogram 2738 with a fixed pitch for each wavelength or spectral component of light incident on the top of dielectric wedge interferometer structure 2745. In some embodiments, gap 2740 may at least partially separate plates 2724 and 2726, such that plates 2724 and 2726 may or may not be in direct contact along an edge (e.g., on the left side of dielectric wedge interferometer structure 2745 in FIG. 28B), as shown. As illustrated in FIG. 28A, in some embodiments, the length of gap 2740 of dielectric wedge interferometer structure 2745 may be oriented in the y-direction of coordinate system 2705 in order to align with the lengths of the reporter strips in reporters 2706 and generate spatially differentiated spectral responses x1', x2', x3' each similar to interferogram 2738. In some embodiments, width 2728 of gap 2740 may vary linearly (e.g., increase along the y-direction in FIG. 28A) in a direction orthogonal to the optical axes of the opposing surfaces (e.g., the internal surfaces of plates 2724 and 2726). Gap 2740 may be substantially vacuum, for example, or may be filled with a dielectric (e.g., air, or another substantially optically transparent dielectric). In embodiments where gap 2740 is filled with a solid, liquid, or gaseous dielectric, the solid or liquid dielectric may be configured to help provide structural support and/or thermal homogeneity for dielectric wedge interferometer structure 2745.

An anti-reflective coating may be applied on the front surface of plate 2724 and the back surface of plate 2726 (e.g., the external surfaces of plates 2724 and 2726), and a partial reflection coating may be applied to the internal surfaces of plates 2724 and 2726 to create a dominate interference within dielectric wedge interferometer structure 2745 that is dependent primarily upon the arrangement of the surfaces of plates 2724 and 2726 relative to each other. As such, the partial reflection coating may be used to suppress or filter non-dominate interference patterns in order to emphasize the dominate interference caused by the arrangement of plates 2724 and 2726, which increases the detectability of the spectrum within the resulting interferogram 2738. Direct path light rays 2730 and multipath reflection rays 2732 combine to form interferogram 2738, which may be projected onto a detector (e.g., detector 2716). Dashed lines 2742 indicate the optical pathlength difference (OPD). When the OPD is approximately equal to multiples of an incident wavelength, rays 2730 and 2732 constructively interfere and form a bright band. Since gap 2740 and, hence, the OPD are both linearly increasing, the resulting interference pattern projects as a periodic pattern of multiple bright bands. The relationship between the fringe pitch (P) between the positions of bright bands, the wavelength of the incident light, and the physical parametrization of the dielectric wedge interferometer structure may be idealized as:

$$P = \frac{S\lambda}{2n\cos\theta},$$

where S=L/W is the "slope" of the wedge, $\lambda$ is the wavelength, n is the refractive index of the material in the gap, and $\theta$ is the light incident angle inside the gap. Using this relationship, the spectrum of incident light may be extracted from interferogram 2738, such as by applying a Fast Fourier Transform (FFT) to image data corresponding to interferogram 2738 using controller 2750. If all the incident light rays, such as the rays at Point A and B in FIG. 28B (e.g., corresponding to rays from different portions of reporters 2706), have the same spectrum, the spectrum of those rays may be acquired with a single acquisition of interferogram 2738. Such a condition may be created by design so that the emission spectrum from a single reporter may be acquired without scanning dielectric wedge interferometer structure 2745/integrated structure 2714 across a certain field of view. Moreover, by aligning the increasing width 2728 of gap 2740 with lengths of reporter strips within reporters 2706, a sufficiently broad dielectric wedge interferometer structure 2745 may be able to form all spectral responses spectral responses x1', x2', x3' at once for acquisition by detector 2716.

For example, in one embodiment, AFP material may be deposited on sensing surface 2720 into a rectangular reporter strip with the length of the strip parallel to the length (e.g., the increasing width 2728) of gap 2740 and thus across a field of view (FOV) of dielectric wedge interferometer structure 2745. In such embodiment, the AFP emission spectrum may be determined from one image acquisition of interferogram 2738 because the corresponding spectral response of the reporter is substantially the same independent of where it was measured (Point A or B, corresponding to different positions along a length of the rectangular reporter strip). In one acquisition, an interference pattern from zero OPD to the maximum OPD allowed by the length of structure is acquired, and so the entire spectrum may be computed up to the Nyquist frequency, as limited by the resolution of detector 2750.

Because reporter emissions are acquired without the narrow slit required in traditional spectrometers, embodiments benefit from the Jacquinot or higher throughput advantage, which can provide increased sensitivity/signal-to-noise ratios over traditional slit-based spectrometers. Moreover, sensitivity/signal-to-noise ratios may also be increased because embodiments can detect multiple wavelengths present within in a single spectral response acquired at a single instance in time (e.g., the Fellgett or multiplexing advantage).

In addition, a dielectric wedge interferometer structure is relatively simple and easy to manufacture and maintain. For example, dielectric wedge interferometer structure 2745 may be formed by a pair of precision ground glass plates with the proper anti-reflective (AR) coating and partial reflective coating on each side. A precision spacer may be inserted between two plates to form the dielectric wedge. In some embodiments dielectric wedge interferometer structure 2745 may be ideally installed directly in front of a sensing surface of detector 2716 (e.g., a CCD array chip surface), to form integrated structure 2714. In such embodiments, the size of integrated structure 2714 may be roughly the same as detector 2716. For example, if a contemporary ½" CCD array is used, detector 2716 may be less than 5×7 mm$^2$, and the total thickness including dielectric wedge interferometer structure 2745 may be less than 0.5 mm. Therefore, dielectric wedge interferometer structure 2745 may be formed extremely compactly. Moreover, in embodiments where integrated structure 2714 is scanned across each of spectral responses x1', x2', x3', the widths of reporter strips or patches within reporters 2706 provide redundant information in each scan acquisition, which may be used for intensity averaging to improve the signal-to-noise ratio of the acquisition. However, the widths of the reporter strips/patches also limits the number of reporter channels that may be used. With a contemporary CCD array of 5~7 mm in width, typical resolution, and assuming unity magnification of lens assembly 2712, 5~7 reporter strips each approximately 1 mm in width may be easily accommodated by embodiments of the present disclosure, and each reporter strip width can be scanned to generate approximately 100~200 interferograms each for averaging, depending on the pixel size/resolution of detector 2716. The number of reporter strips on sensing surface 2720 may be doubled by reducing the number of interferograms to be averaged by half.

In various embodiments, it is important that the arrangement of reporters 2706 (e.g., reporter strips or patches), lens assembly 2712, and/or other elements of hyperspectral detector module is capable of capturing as much emitted light as possible to form the multiple interferograms and determine their spectral content. In FIG. 28, reporters 2706 include there are three reporter strips x1, x2, x3, located in the object plane and three corresponding interferograms/spectral responses x1', x2', x3' in the image plane of detector 2716. All the interferograms are spatially separated without overlapping so that the spectrum information from each reporter strip can be interrogated individually without any interference from another reporter strip. In some embodiments, detector 2716 may be wide enough so that each interferogram contains the spectrum of the emission from an entire strip and/or all strips within reporters 2706, and no scanning process is required to acquire each spectral response or, in some embodiments, all spectral responses generated by reporters 2706. In some embodiments, a reporter strip length may be approximately 5~7 mm, but more generally, the strip length may be increased or decreased and compensated for by adjusting the magnification of lens assembly 2712.

Figure 29:
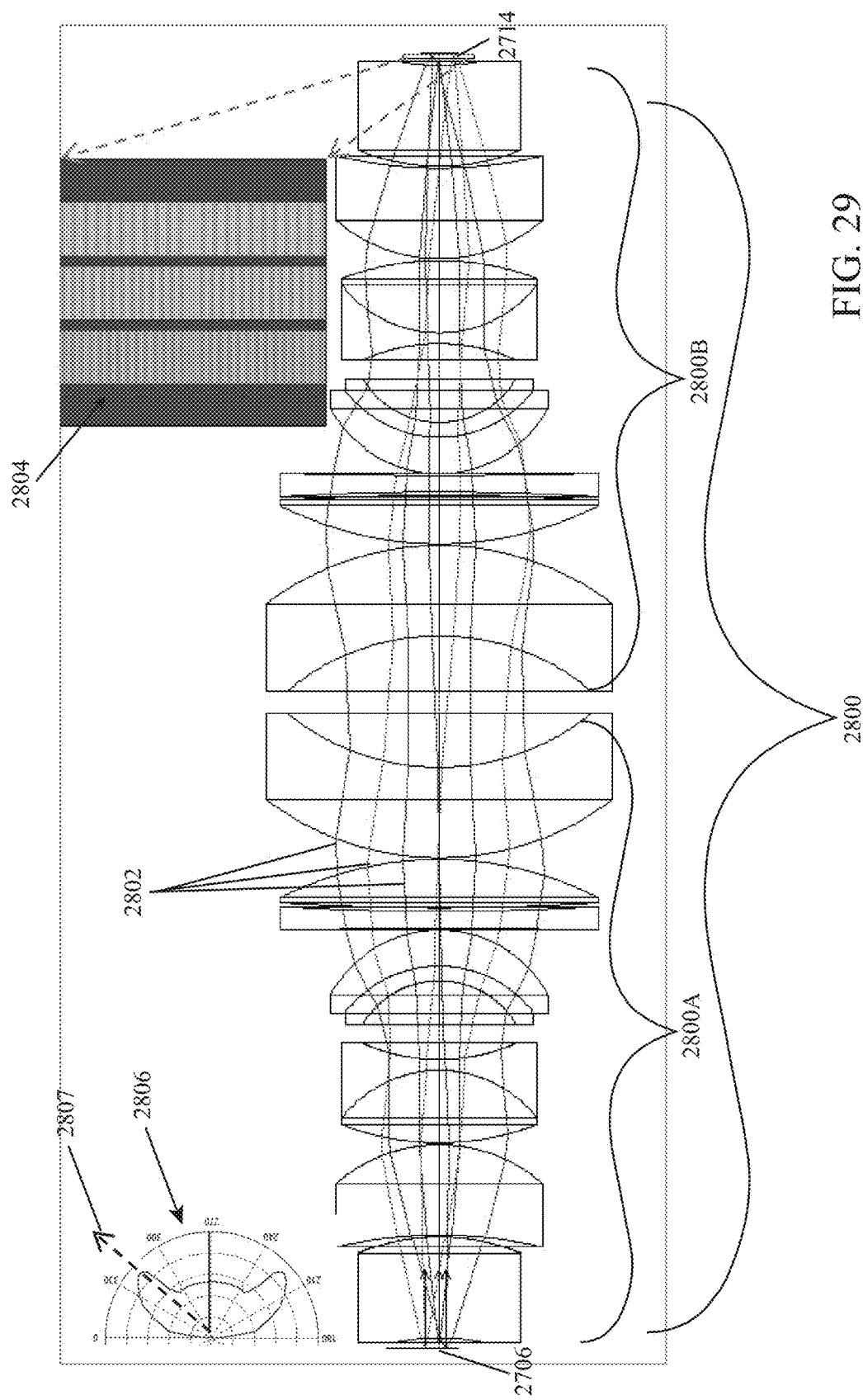
FIG. 29 illustrates a lens assembly for use in an optical collection and detection device, in accordance with an embodiment of the disclosure.

Emissions from reporter materials deposited on a flat transparent surface (e.g., reporters 2706 on sensing surface 2720) may have complex emission distributions. Constituent photons, instead of being isotropically or omnidirectionally emitted, may be emitted according to a preferential emission direction substantially along a surface of sensing surface 2720 and concentrating at a critical emission angle 2807 (e.g., approximately 45 degrees half angle on an air/glass interface coated with AFP and/or other reporter materials). An example emission pattern is provided in insert 2806 at the top-left corner of FIG. 29. FIG. 29 illustrates a lens assembly 2800 for use in optical collection and detection device 2700, in accordance with an embodiment of the disclosure. In some embodiments, optics 2758, and/or lens assembly 2712 of FIGS. 27 and 28A, and/or other lens assemblies discussed with reference to FIGS. 31A-33, may be implemented according to lens assembly 2800 and/or portions of lens assembly 2800.

In FIG. 29, lens assembly 2800 is implemented as a pair of nine-element double-Gauss lens arrangements 2800A and B. The complete collection of emissions, such as emissions along rays 2802 from reporters 2706, can be implemented with an index matching fluid and/or prism used in conjunction with relatively large numerical aperture optics. In a free space collection scheme, emissions close to and greater than critical angle 2807 are typically trapped inside sensing surface 2720 and cannot be converged towards detector 2716 and/or integrated structure 2714. As a result, lens assembly 2800 may be configured to converge emissions with emission angles up to approximately 35-45 degrees (e.g., half angle) without substantial loss of available emitted light from reporters 2706.

Lens arrangements with a relatively large numerical aperture (e.g., double-Gauss lens arrangements 2800A and/or B) may be used in pairs to converge a relatively large portion of the light emitted by reporters 2706. In some embodiments, lens assembly 2800 may be configured to maximize the range of emission angles converged by lens assembly 2800 while maintaining a suitable spectral and/or spatial resolution at detector 2716 and/or integrated structure 2714. For example, rays 2802 of FIG. 29 illustrate ray tracing modeling results of lens assembly 2800. The large F number (e.g., F/0.85) of lens arrangement 2800A is configured (e.g., shaped and/or arranged) to converge emissions with emission angles up to approximately 30 degrees (e.g., half-angle). After the emissions are converged, captured, and/or collimated by lens arrangement 2800A, lens arrangement 2800B is configured to focus the emissions on dielectric wedge interferometer structure 2745 and/or integrated structure 2714 to generate interferograms 2804. In some embodiments, lens assembly 2800 may be configured to provide a unity magnification. In the upper right corner of FIG. 29, interferograms 2804 shows three interferograms corresponding to three reporter strips of reporters 2706 (e.g., using false color to represent the intensity and the interference pattern clearly) as detected by detector 2716/integrated structure 2714. In interferograms 2804, the primary emission wavelengths are 460 nm, 500 nm, and 600 nm arranged from left to right. The increasing pitches from left to right correspond to the increasing wavelengths of the emissions.

In various embodiments, a nine-element double-Gauss lens arrangement (e.g., lens arrangements 2800A and B) may be configured to provide faster or slower optics (e.g., a capacity to converge larger or narrower emission angles towards detector 2716/integrated structure 2714), depending on an overall desired manufacturing cost related to lens complexity, physical size, and weight (e.g., approximately 530 grams of glass was used to form lens assembly 2800 with a convergence angle of approximately 30 degrees half angle). In addition to convergence angle and/or numerical aperture, other criteria such as optical phase dispersion, spot diagram, and chromatic aberration may be selected and/or adjusted to design for a desired and/or target spectral resolution. In general, lens assembly 2800 may be implemented as any multi-element lens arrangement configured to receive light with emission angles up to approximately 35-45 degrees, half angle, emitted by reporters 2706, and focus the received light onto detector 2716 and/or integrated structure 2714, for example.

Figure 30:
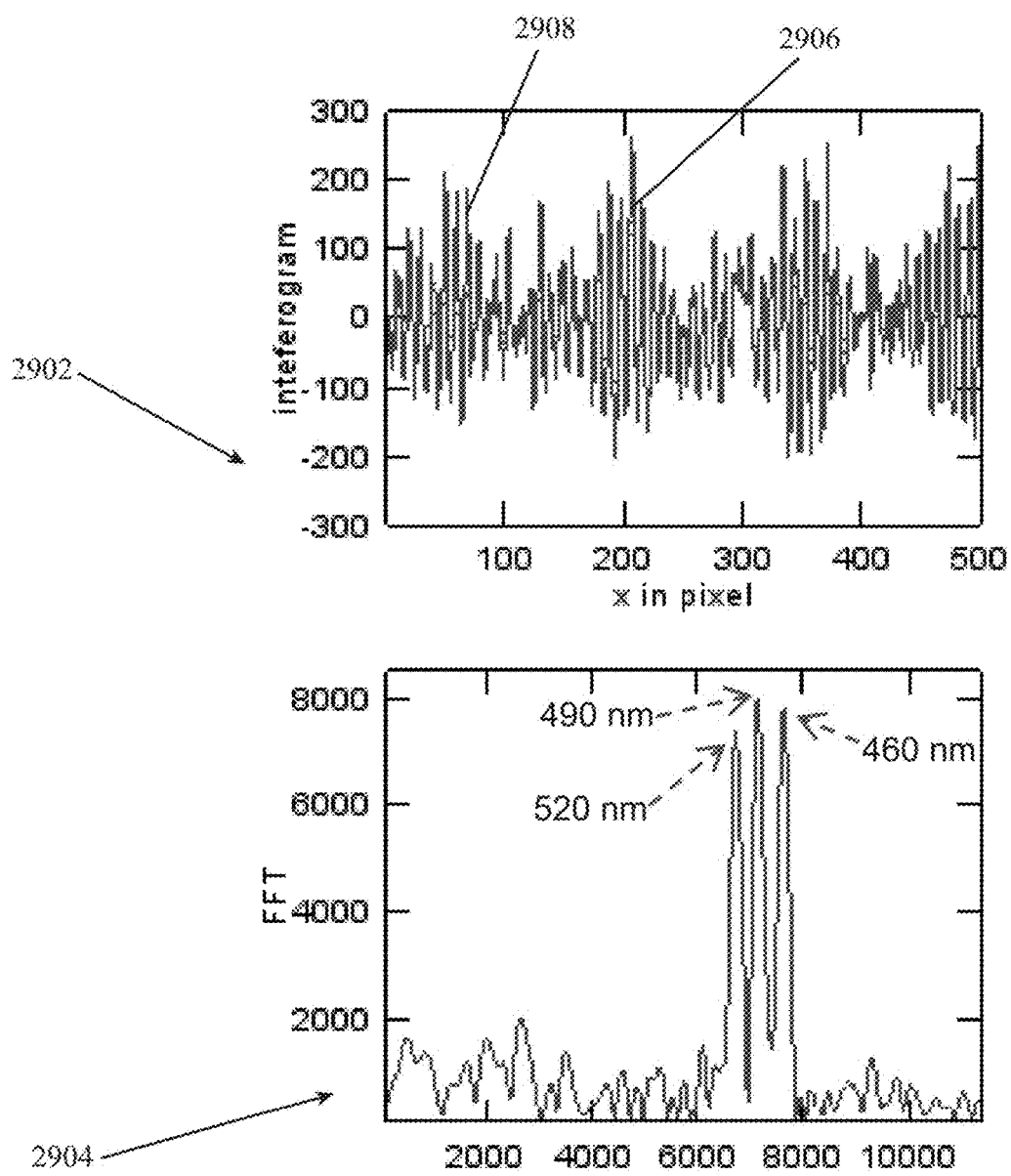
FIG. 30 illustrates data of an interferogram and a spectrum provided by an optical collection and detection device implemented with a hyperspectral detection module based on a dielectric wedge interferometer structure, in accordance with an embodiment of the disclosure.

FIG. 30 illustrates data of an interferogram and a spectrum provided by an optical collection and detection device implemented with a hyperspectral detection module based on a dielectric wedge interferometer structure, in accordance with an embodiment of the disclosure. In particular, FIG. 30 illustrates the spectral resolution of lens assembly 2800 in FIG. 29 coupled with a dielectric wedge interferometer structure implemented with BK7 glass and a slope S of 367. For example, a single reporter strip or patch of reporters 2706 may emit three different wavelengths: 460 nm, 490 nm, and 520 nm. Plot 2902 shows an intensity of an interferogram (e.g., corresponding to interferogram 2738 of FIG. 28B and/or interferograms 2804 of FIG. 29) acquired by detector 2716/integrated structure 2714 plotted against a pixel position along a length of the interferogram. Plot 2904 shows the spectrum of the interferogram computed via an FFT. A red or dark trace 2906 on top of a blue or light trace 2908 is an apodized version of the interferogram using a triangular window to smooth the discontinuities at the beginning and end of the sampled time record. In plot 2904, three emission peaks are visible in the spectrum (e.g., the leftmost peak is the 520-nm peak, the center peak is the 490-nm peak, and the rightmost peak is the 460 nm peak), which demonstrates that spectral resolutions sufficient to differentiate spectral components separated by 10-30 nm in wavelength may be achieved by device 2700 implemented with hyperspectral detector module 2711 including dielectric wedge interferometer structure 2745.

In normal usage, a sample vapor including analytes 2704 may be first into a nozzle of sampling system 2718 and then flowed across reporter strips of reporters 2706 in a low-profile flow channel. In some embodiments, analyte flow 2710 may be configured to allow analytes 2704 to interact with the reporter strips in a sequential order (e.g., from left to right in FIG. 28A). The total instantaneous intensity across one or more interferograms acquired by hyperspectral detector module 2711 may be summed up by controller 2750 and displayed on display 2754 for an operator as a rapid feedback of the sensing event. After data acquisition over a period of time, the entire footage (e.g., multiple images and/or video) may be processed by controller 2750 to determine the time history of the emission spectrum of each reporter strip individually either autonomously or manually by the operator via user interface 2752. By comparing instantaneous spectra to a baseline spectrum (derived from the time history), the spectral response induced by the incoming air sample for each reporter strip may be compiled into a temporal spectral signature, as described herein. Since the two dimensional temporal spectral signatures for different reporters are spatially differentiated, a three dimensional reporter temporal spectral signature including temporal spectral signatures from multiple different reporters may be used to accurately detect and robustly identify explosives and/or other analytes.

Figure 31A:
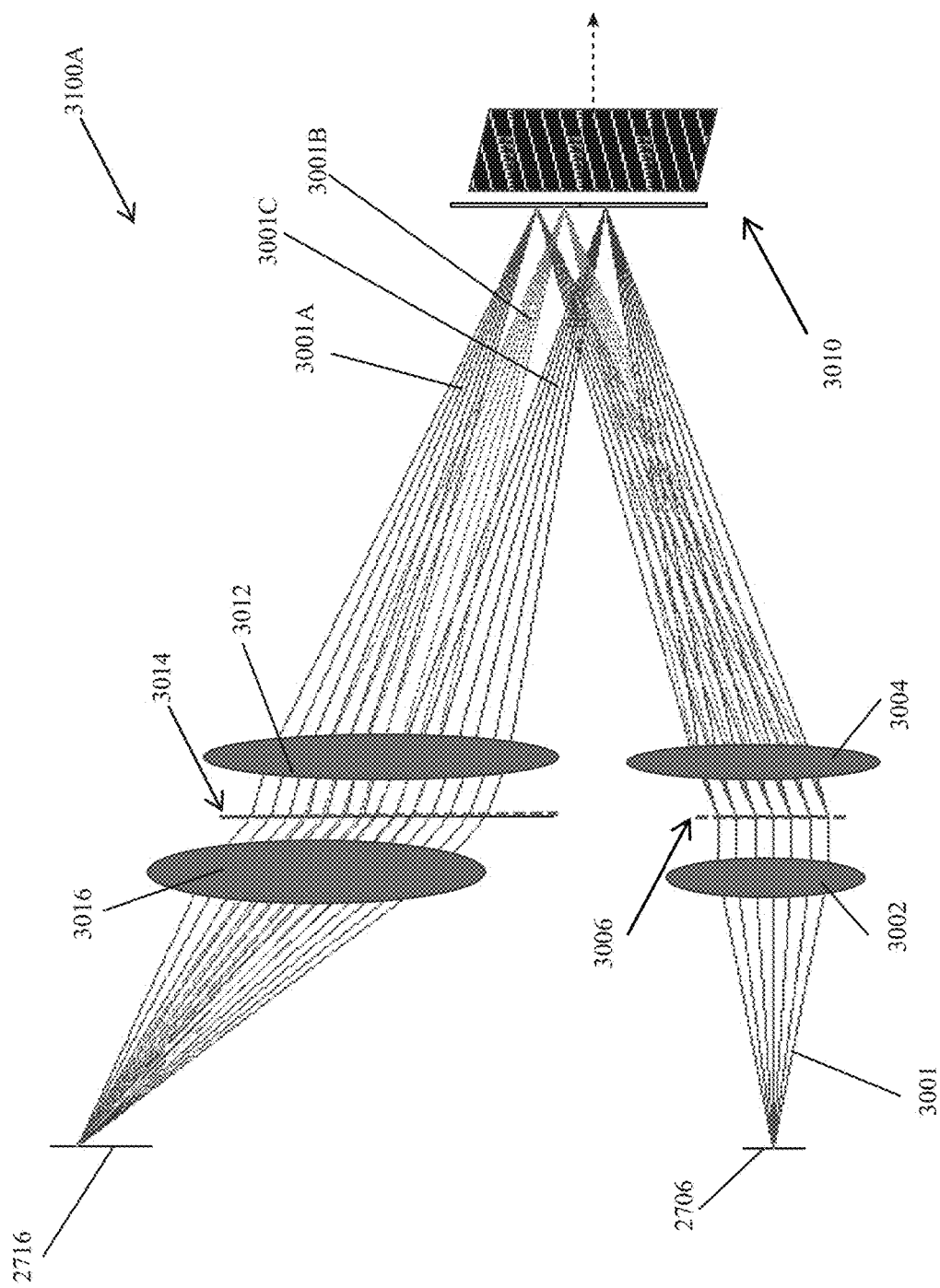
FIGS. 31A-B illustrate a hyperspectral detection module based on a coded aperture spectrometer structure, in accordance with an embodiment of the disclosure.
Figure 31B:
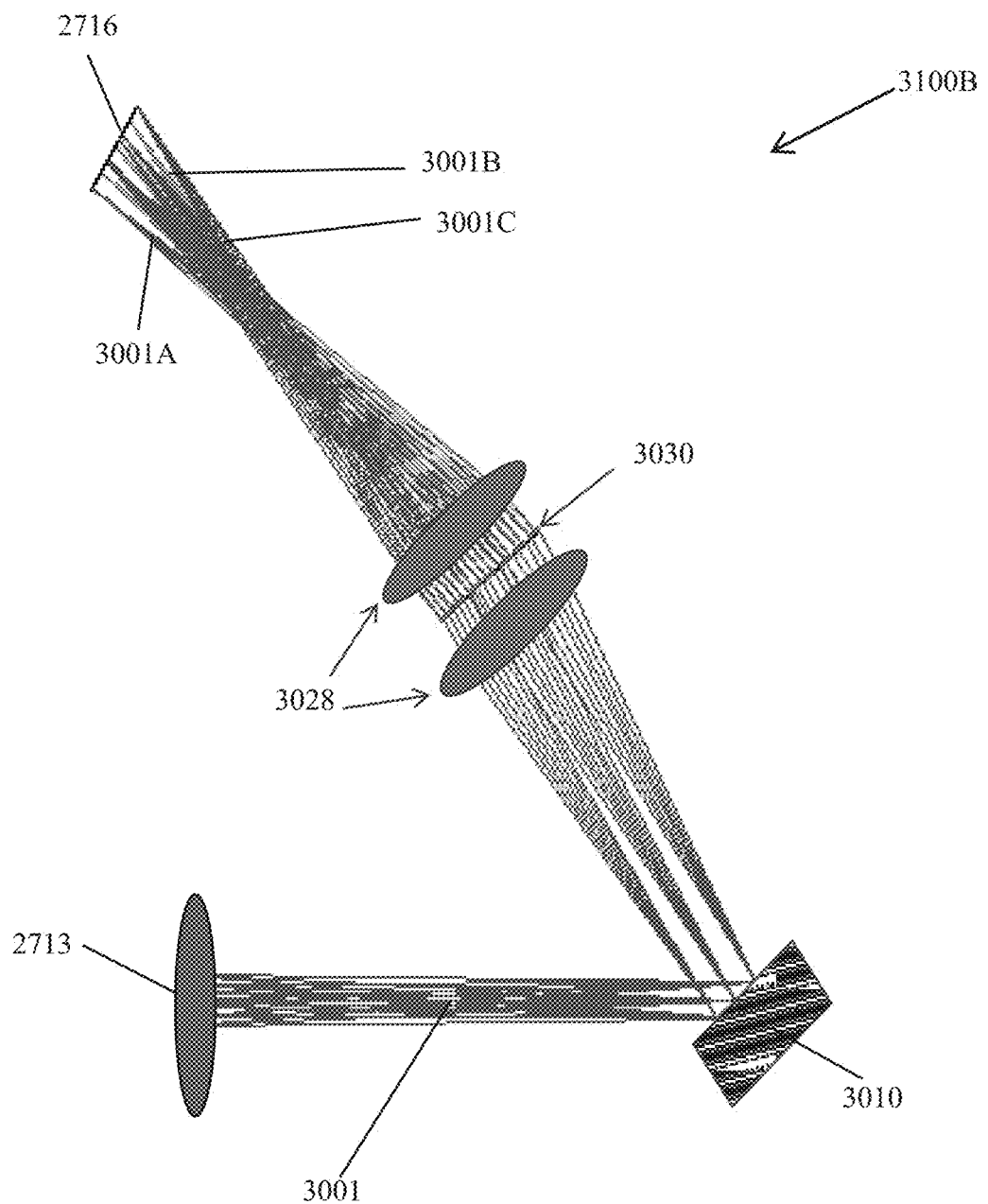

FIGS. 31A, 31B, and 32C each illustrate a hyperspectral detection module based on a coded aperture spectrometer structure, in accordance with an embodiment of the disclosure. For example, as shown in FIGS. 31A-32C, a coded aperture spectrometer (CAS) structure 3100 (e.g., CAS structures 3100A and/or 3100B) may be used to implement hyperspectral detection module 2711 of FIG. 27. In general, CAS structure 3100 includes at least one dispersive element (e.g., dispersive elements 3006 and 3014 of CAS structure 3100A and/or dispersive element 3030 of CAS structure 3100B) and a coded aperture 3010. The dispersive element (s) (e.g., a grating, a grid, a prism, and/or other types of dispersive elements) is configured to separate incident light into its constituent spectral components, and the coded aperture is configured to pass or block incident light according to a set of selectable passed light patterns each corresponding to a different spectral band (e.g., a different continuous set of wavelengths) for a particular spatial area or point on reporters 2706. In various embodiments, the set of selectable passed light patterns may be implemented according to a set of circularly cycled Hadamard matrices, and images of each Hadamard matrix-based passed light pattern may be aggregated into a spatial-spectrum data cube that, when processed according to a Hadamard Transform (HT) corresponding to the set of Hadamard matrices, results in a spatially differentiated spectrum of the light incident to CAS structure 3100 (e.g., CAS structures 3100A and/or 3100B), similar to that presented in plot 2904 of FIG. 30, such as a differentiated spectrum for each reporter strip or patch of reporters 2706.

As such, CAS structure 3100 may be configured to retain spatial information of light incident to CAS structure 3100, and so hyperspectral detection module 2711 implemented with CAS structure 3100 in FIG. 32 may be used to determine the spectrums of multiple different reporters (e.g., at different spatial positions) substantially simultaneously (e.g., limited by the frame rate of detector 2716, the number of differentiated spectral bands, and the number of reporter strips/patches). For example, CAS structure 3100 (e.g., CAS structure 3100A and/or 3100B) may be configured to produce a set of passed light patterns corresponding to an array of reporters 2706, where each reporter strip or patch is represented within a subset of passed light patterns in the set of patterns. Because full spectral data are acquired in each sub-frame acquisition, there is a multiplex advantage that results in relatively high photon collection efficiency, and the full spatial resolution of the detector may be retained. Some limitations on the overall performance of a hyperspectral detection module implemented with CAS structure 3100 include the maximum frame rate of detector 2716 and the number of spectral bands (e.g., particularly with respect to large numbers of bands (n)), where a relatively high spectral resolution may result in a relatively low temporal resolution, for example.

The spectral resolution and spectral interrogation range of CAS structure 3100 (shown in FIG. 32) are typically determined by the number of spectral bands (n) (e.g., which is also the number of Hadamard matrices in a complete circular cycle and the number of rows or columns for each Hadamard matrix), the amount of dispersion provided by included dispersion elements, and the size/resolution of CA 3010 (e.g., a digital micro-mirror device (DMD), a liquid crystal pixel array, and/or other coded aperture devices) and detector 2716. The resolution may be limited by the camera frame rate and an allowed integration/acquisition time; however, relatively high resolution may still be achieved. For example, a spectral resolution of approximately 6 nm may be achieved with a commonly available DMD chip with a resolution of 684×608 pixels configured (e.g., using a selected set of Hadamard matrices) to interrogate the spectrum between 400 nm and 650 nm with 43 spectral bins/bands (e.g., n=43). In general, such DMDs may include several hundred thousand microscopic mirrors each with surfaces several microns in size that may be tilted (e.g., approximately 12 degrees off the DMDs' optical axis) to turn "on" or "off" each individual mirror.

In FIG. 31A, light 3001 from reporters 2706 is dispersed by first dispersive element 3006 to separate light 3001 into spectral components 3001A-C (indicated in FIG. 31A after passed by CA 3010). The spectrally and spatially overlapped scene is projected onto CA 3010 (e.g., where aperture coding may be performed by switching "on" or "off" individual mirrors in a DMD, for example). The coded color-dispersed scene from CA 3010 may be recombined by second dispersion element 3014 and finally detected by detector 2716 (e.g., a monochrome camera, an infrared camera, an FPA, and/or other type of detector, as described herein). The full-spectrum light from all "on" pixels is detected at the same time; therefore, CAS structure 3100A benefits from the multiplex and large aperture (Fellgett's and Jacquinot) advantage. In some embodiments, CAS structure 3100 (e.g., CAS structures 3100A and/or 3100B) may be implemented with a second detector configured to capture light from mirrors in the "off" state to increase and/or double the photon efficiency of CAS structure 3100 to nearly 100 percent. In various embodiments, lens assemblies 3002, 3004, 3012, and/or 3016 may be integrated with CAS structure 3100A to collimate (e.g., lens assemblies 3002/3012) and/or focus/image (lens assemblies 3004/3016) light processed by CAS structure 3100A. For example, optics 2758 and/or lens assembly 2712 may include such lens assemblies.

In some embodiments, CA 3010 may be configured to modulate the intensity of the light provided to detector 2716 by passing light for an increased or a decreased period of time (e.g., modulate the duty cycle of the "turn on" state of CA 3010) while detector 2716 is actively acquiring a sub-frame/image of a spatial-spectrum data cube. Such intensity modulation capability allows CAS structure 3100 (e.g., CAS structures 3100A and/or 3100B) to perform "high dynamic range" (HDR) imaging that can accommodate extremely bright spots and reveal spatial and/or spectral details hidden in relatively low intensity portions of a scene. Such capability is highly desirable for FPA-based and/or other types of detection platforms with relatively limited intensity dynamic range.

FIG. 31B illustrates a hyperspectral detection module based on a coded aperture spectrometer structure with a single dispersion element, so as to reduce cost, weight, size, and/or complexity of a resulting hyperspectral detection module 2711. As shown in FIG. 31B, CAS structure 3100B includes CA 3100 configured to receive light 3001 from reporters 2706 (e.g., through aperture/optics 2713 of CAS structure 3100B) and to provide coded light to dispersion element 3030, which separates the coded light into coded spectrum dispersed light 3001A-C for detection by detector 2716. In some embodiments, the same Hadamard matrices used with respect to CAS structure 3100A may be used with CAS structure 3100B, and the resulting spatial-spectrum data cube may be processed, based on the known arrangement of elements of CAS structure 3100B, to map data within the spatial-spectrum data cube to locations corresponding to the spatial arrangement of reporters 2706 (e.g., such process is generally unnecessary in CAS structure embodiments with two dispersion elements, such as CAS structure 3100A, where the second dispersion element effectively maps the spectral content back to its relative spatial location in the image plane of detector 2716). Lens assemblies 3028 may be integrated with CAS structure 3100B to collimate and/or focus light from CA 3010 for dispersion element 3030 and/or detector 2716, as shown.

FIG. 32 illustrates device 2700 including hyperspectral detector module 2711 implemented with CAS structure 3100 (e.g., CAS structure 3100A or B). In general, hyperspectral detector module 2711 including CAS structure 3100 is less restrictive with respect to its orientation relative to reporters 2706 (e.g., strips and/or patches) than hyperspectral detector module 2711 including dielectric wedge interferometer structure 2745 in FIG. 28A, for example, and hyperspectral detector module 2711 including 1D stepped FP interferometer structure 3204, as described more fully below.

Figure 33:
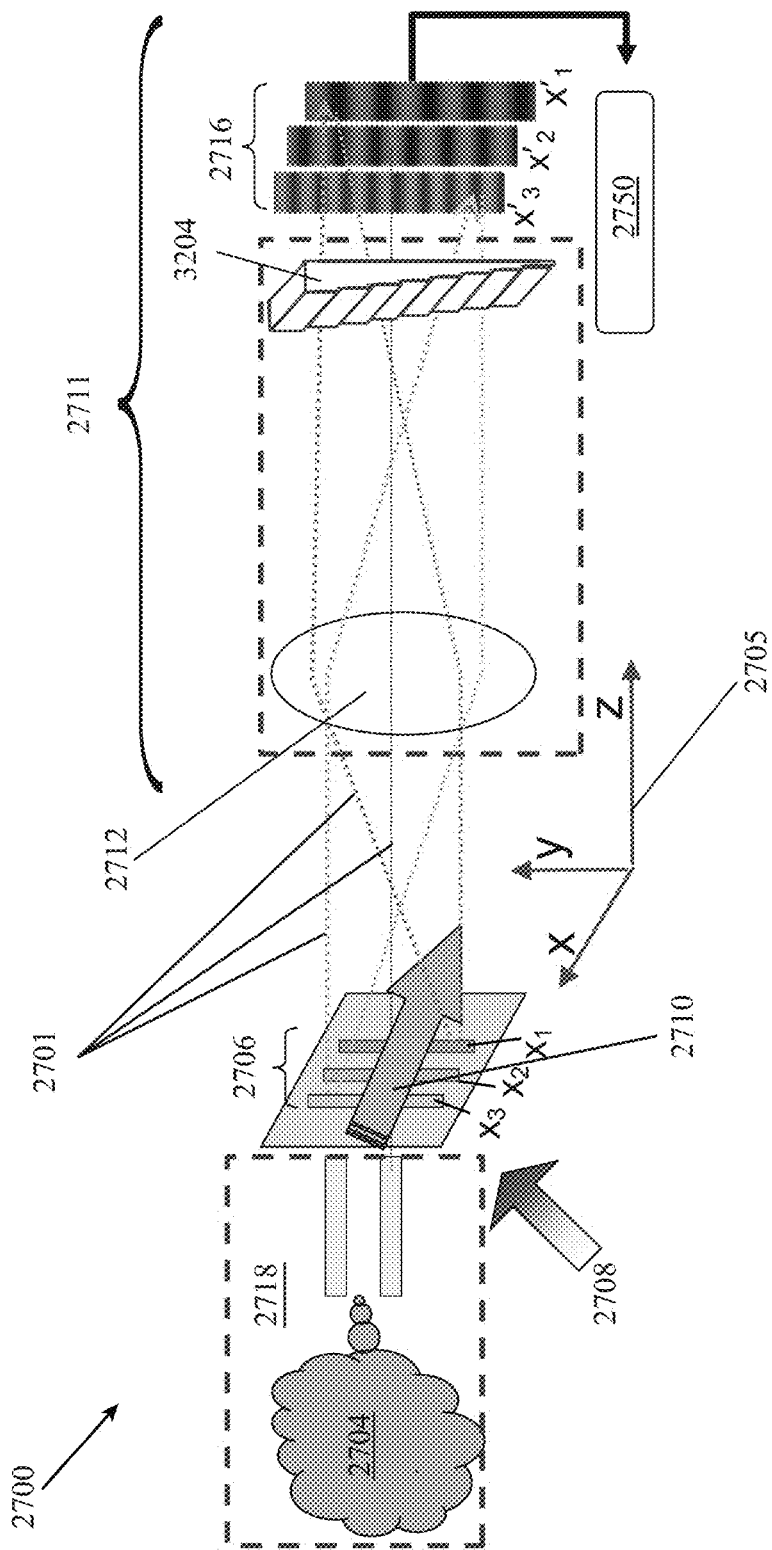
FIG. 33 illustrates an optical collection and detection device implemented with a hyperspectral detection module based on a one dimensional (1D) stepped Fabry-Perot interferometer structure, in accordance with an embodiment of the disclosure.

FIG. 33 illustrates optical collection and detection device 2700 implemented with hyperspectral detection module 2711 based on a 1D stepped Fabry-Perot (FP) interferometer structure 3204, in accordance with an embodiment of the disclosure. A 1D stepped FP interferometer structure may be equivalent to a discretized case of a dielectric wedge interferometer structure with a 1D slope. As such, 1D stepped FP interferometer structure 3204 may be arranged with its cavity spacing variation aligned along the direction of the length of reporter strips 2706 as shown in FIG. 32. Effectively, each reporter strip will be imaged through an array of interferometer structures with uniformly increasing cavity sizes. Hyperspectral detector module 2711 may also include a lens assembly 2712 (e.g., which may be implemented similar to optics 2758 of FIG. 27, lens assembly 2712 of FIG. 28A, and/or lens assembly 2800 of FIG. 29) to collect and concentrate emissions from reporters 2706. Each reporter strip x1, x2, x3 of reporters 2706 may form its own interferogram x1', x2', x3' on detector 2716 so that the spectral information of each reporter channel determined independently, similar to the general operation of hyperspectral detector module 2711 of FIG. 28A.

1D stepped FP interferometer structure 3204 may include a plurality of interferometer structures (e.g., the "steps" of the structure) arranged in a rectangular array, wherein each individual interferometer structure includes of two partially transmissive mirrors that are separated so that the distances between the two mirrors of the corresponding interferometers are uniformly distributed in a range from a relatively small distance to a relatively large distance so to disperse light emitted by reporters 2706 into corresponding spectral components to form interferograms x1', x2', x3'. Resulting interferograms x1', x2', x3' may be processed (e.g., application of an FFT, for example) by controller 2750 to determine the spectrum of each reporter within reporters 2706, similar to the processing described with respect to hyperspectral detector module 2711 of FIG. 28A. In some embodiments, 1D stepped FP interferometer structure 3204 may be integrated with detector 2716 to form a compact imaging module, as described herein.

Where applicable, various embodiments provided by the present disclosure can be implemented using hardware, software, or combinations of hardware and software. Also where applicable, the various hardware components and/or software components set forth herein can be combined into composite components comprising software, hardware, and/or both without departing from the spirit of the present disclosure. Where applicable, the various hardware components and/or software components set forth herein can be separated into sub-components comprising software, hardware, or both without departing from the spirit of the present disclosure. In addition, where applicable, it is contemplated that software components can be implemented as hardware components, and vice-versa.

Software in accordance with the present disclosure, such as non-transitory instructions, program code, and/or data, can be stored on one or more non-transitory machine readable mediums. It is also contemplated that software identified herein can be implemented using one or more general purpose or specific purpose computers and/or computer systems, networked and/or otherwise. Where applicable, the ordering of various steps described herein can be changed, combined into composite steps, and/or separated into sub-steps to provide features described herein.

Embodiments described above illustrate but do not limit the invention. It should also be understood that numerous modifications and variations are possible in accordance with the principles of the invention. Accordingly, the scope of the invention is defined only by the following claims.

What is claimed:

1. A device comprising:
   a plurality of reporters disposed on a sensing surface, wherein each one of the plurality of reporters is configured to react with a least one target analyte;
   a hyperspectral detection module configured to capture hyperspectral image data corresponding to the plurality of reporters, wherein the hyperspectral detection module comprises a dielectric wedge interferometer structure configured to produce a plurality of interferograms corresponding to the plurality of reporters without scanning the dielectric wedge interferometer structure across the plurality of reporters; and
   a controller configured to:
      receive the hyperspectral image data from the hyperspectral detection module; and
      generate a temporal spectral signature corresponding to each one of the plurality of reporters from the received hyperspectral image data.

2. The device of claim 1, wherein:
   the plurality of reporters comprises at least two different reporter materials; and
   the plurality of reporters comprises an array of reporter strips or an array of reporter patches.

3. The device of claim 1, further comprising:
   an excitation assembly configured to provide optical excitation of at least one of the plurality of reporters via a light source configured to emit an excitation wavelength, wherein the at least one of the plurality of reporters comprises a fluorescing reporter.

4. The device of claim 1, further comprising:
   an input segment configured to receive an analyte transport fluid, wherein the sensing surface is in fluid communication with the input segment.

5. The device of claim 1, wherein:
   the hyperspectral image data comprises the plurality of interferograms; and
   the controller is configured to generate the temporal spectral signature by processing each one of a time series of the plurality of interferograms, corresponding to one of the plurality of reporters, to extract a time series of spectrums of the one of the plurality of reporters.

6. The device of claim 1, wherein:
the dielectric wedge interferometer structure comprises two glass plates that are at least partially separated by a linearly varying gap; and
the air-wedge interferometer structure is integrated with a detector of the hyperspectral detector module.

7. The device of claim 5, wherein:
the plurality of reporters comprise an array of reporter strips;
a length of a gap of the dielectric wedge interferometer structure is aligned with lengths of the array of reporter strips; and
the controller is configured to apply a fast Fourier transform to the hyperspectral image data to generate each temporal spectral signature.

8. The device of claim 1, wherein:
the hyperspectral detector module comprises a lens assembly implemented as a multi-element lens arrangement configured to receive light comprising emission angles up to approximately 35-45 degrees, half angle, emitted by the plurality of reporters and to focus the received light onto a detector of the hyperspectral detector module.

9. A method comprising:
receiving hyperspectral image data from a hyperspectral detection module, wherein the hyperspectral detection module is configured to capture hyperspectral image data corresponding to a plurality of reporters disposed on a sensing surface, the hyperspectral detection module comprises a dielectric wedge interferometer structure configured to produce a plurality of interferograms corresponding to the plurality of reporters without scanning the dielectric wedge interferometer structure across the plurality of reporters, and each one of the plurality of reporters is configured to react with a least one target analyte; and
generating a temporal spectral signature corresponding to each one of the plurality of reporters from the received hyperspectral image data.

10. The method of claim 9, wherein:
the plurality of reporters comprises at least two different reporter materials;
the plurality of reporters comprises an array of reporter strips or an array of reporter patches; and
the method further comprises determining a presence and/or type of the at least one target analyte from the temporal spectral signatures.

11. The method of claim 9, further comprising:
providing optical excitation of at least one of the plurality of reporters via a light source configured to emit an excitation wavelength, wherein the at least one of the plurality of reporters comprises a fluorescing reporter.

12. The method of claim 9, wherein:
the hyperspectral image data comprises the plurality of interferograms; and
the generating the temporal spectral signature comprises processing each one of a time series of the plurality of interferograms, corresponding to one of the plurality of reporters, to extract a time series of spectrums of the one of the plurality of reporters.

13. The method of claim 9, wherein:
the dielectric wedge interferometer structure comprises two glass plates that are at least partially separated by a linearly varying gap; and
the air-wedge interferometer structure is integrated with a detector of the hyperspectral detector module.

14. The method of claim 12, wherein:
the plurality of reporters comprise an array of reporter strips;
a length of a gap of the dielectric wedge interferometer structure is aligned with lengths of the array of reporter strips; and
the generating the temporal spectral signature comprises applying a fast Fourier transform to the hyperspectral image data.

15. The method of claim 9, wherein:
the hyperspectral detector module comprises a lens assembly implemented as a multi-element lens arrangement configured to receive light comprising emission angles up to approximately 35-45 degrees, half angle, emitted by the plurality of reporters and to focus the received light onto a detector of the hyperspectral detector module.

\* \* \* \* \*

UNITED STATES PATENT AND TRADEMARK OFFICE
CERTIFICATE OF CORRECTION

PATENT NO. : 10,101,273 B2
APPLICATION NO. : 14/821553
DATED : October 16, 2018
INVENTOR(S) : Shiou-jyh Ja Page 1 of 1

It is certified that error appears in the above-identified patent and that said Letters Patent is hereby corrected as shown below:

In the Specification

In Column 32, Line 45, change "FUR" to --FLIR--.

Signed and Sealed this
Eleventh Day of December, 2018

Andrei Iancu
*Director of the United States Patent and Trademark Office*